United States Patent
Wilkes

(10) Patent No.: US 7,348,005 B2
(45) Date of Patent: Mar. 25, 2008

(54) ORAL TOLERANCE INDUCTION BY COLLAGEN TO PREVENT ALLOGRAFT REJECTION

(75) Inventor: David S. Wilkes, Indianapolis, IN (US)

(73) Assignee: Advanced Research and Technology Institute, Indianapolis, IN (US)

(*) Notice: Subject to any disclaimer, the term of this patent is extended or adjusted under 35 U.S.C. 154(b) by 610 days.

(21) Appl. No.: 10/243,797

(22) Filed: Sep. 13, 2002

(65) Prior Publication Data

US 2003/0078208 A1  Apr. 24, 2003

Related U.S. Application Data

(63) Continuation of application No. PCT/US01/08680, filed on Mar. 15, 2001.

(60) Provisional application No. 60/189,420, filed on Mar. 15, 2000.

(51) Int. Cl.
 *A61K 39/00* (2006.01)
 *A61K 39/38* (2006.01)
(52) U.S. Cl. .................... 424/184.1; 530/356
(58) Field of Classification Search ............ 424/184.1; 530/356
See application file for complete search history.

(56) References Cited

U.S. PATENT DOCUMENTS 5,593,698 A  1/1997  Weiner et al.
5,962,025 A  10/1999  Carbone et al.

OTHER PUBLICATIONS

Hausen, B., et al. Transplantation. Feb. 15, 1999;67(3):354-359.*
Mares, D.C., et al. Am J. Respir. Cell Mol. Biol. Jul. 2000;23:62-70.*
Chen et al., "Peripheral deletion of antigen-reactive T cells in oral tolerance," *Nature*, 376:177-180, 1995.
Chen et al., "Regulatory T-cell clones induced by oral tolerance: suppression of autoimmune encephalomyelitis," *Science*, 265:1237-1240, 1994.
Chiang et al., "Type V(A-B) collagen induces platelet aggregation," *J. Lab. Clin. Med.*, 95:99-107, 1980.
Cremer et al., "Type XI collagen-induced arthritis in the Lewis rat: characterization of cellular and humoral immune responses to native types XI, V, and II collagen and constituent α-chains," *J. Immunol.* 153:824-832, 1994.
Danzer et al., "Cytokine interactions in human mixed lymphocyte culture," *Transplantation*, 57(11):1638-1642, 1994.
DeMeester et al., "The bimodal expression of tumor necrosis factor-α in association with rat lung reimplantation and allograft rejection," *J. Immunol.*, 150(6):2494-2505, 1993.
Faria and Weiner, "Oral tolerance: mechanisms and therapeutic applications," *Adv. Immunol.*, 73:153-264, 1999.
Felts et al., "Immunologic tolerance to collagen and glycosaminoglycan components of scleral allografts in humans," *J. of Periodontology*, 52:603-608, 1981.

Garrovillo et al., "Indirect allorecognition in acquired thymic tolerance: induction of donor-specific tolerance to rat cardiac allografts by allopeptide-pulsed host dendritic cells," *Transplantation*, 68:1827-1834, 1999.
Hancock et al., "Oral, but not intravenous, alloantigen prevents accelerated allograft rejection by selective intragraft Th2 cell activation," *Transplantation*, 55:1112-1118, 1993.
Hanson et al., "The human α2(XI) collagen gene (COL11A2) maps to the centrometric of the major histocompatibility complex on chromosome 6," *Genomics*, 5:925-931, 1989.
Hirt et al., "Development of obliterative bronchiolitis after allogeneic rat lung transplantation: Implication of acute rejection and the time point of treatment," *J. Heart Lung Transplant.*, 18:542-548, 1999.
Huang et al., "Stable mixed chimerism and tolerance using a nonmyeloablative preparative regimen in a large-animal model," *J. Clin. Invest.*, 105:173-181, 2000.
Ishido et al., "Induction of donor-specific hyporesponsiveness and prolongation of cardiac allograft survival by jejunal administration of donor splenocytes," *Transplantation*, 68:1377-1382, 1999.
Iyer et al., "Characterization and biologic significance of immunosuppressive peptide D2702.75-84(E α V) binding protein," *J. Biol. Chem.*, 273(5):2692-2697, 1998.
Joo et al., "T-cell mediated responses in a murine model of orthotopic corneal transplantation," *Invest. Ophthalmol. Vis. Sci.*, 36:1530-1540, 1995.
Josien et al., "Fas ligand, tumor necrosis factor-alpha expression, and apoptosis during allograft rejection and tolerance," *Transplantation*, 66:887-893, 1998.
Kallio et al., "Role of nitric oxide in experimental obliterative bronchiolitis (chronic rejection) in the rat," *J. Clin Invest.*, 100:2984-2994, 1997.
Konomi et al., "Localization of type V collagen and type IV collagen in human cornea, lung, and skin," *Am. J. Pathol.*, 116:417-426, 1984
Krensky and Clayberger, "HLA-derived peptides as novel immunosuppressives," *Nephrol. Dial. Transplant.*, 12:865-878, 1997.
Lowry et al., "Immune mechanisms in organ allograft rejection. VI. Delayed-type hypersensitivity and lymphotoxin in experimental renal allograft rejection," *Transplantation.*, 40:183-188, 1985.
Madri and Furthmayr, "Collagen polymorphism in the lung," *Human Pathology*, 11:353-366, 1980. .

(Continued)

*Primary Examiner*—G. R. Ewoldt
(74) *Attorney, Agent, or Firm*—Fulbright & Jaworski L.L.P.

(57) ABSTRACT

The present invention relates to the use of collagen and MHC-like compounds to down regulate immune responses. Methods for administration of such compounds that induce immune tolerance are described. The invention is important in the context of allograft rejection, transplantation, graft rejection, pleural disease and immunotolerance.

15 Claims, 22 Drawing Sheets

OTHER PUBLICATIONS

Madri and Furthmayr, "Isolation and tissue localization of type AB2 collagen from normal lung parenchyma," *Am. J. Pathol.*, 94:323-332, 1979.

Marck et al., "Lung transplantation in the rat. III. Functional studies in iso- and allografts," *J. Surgical Res.*, 35:149-158, 1983.

Mares et al., "Type V collagen modulates alloantigen-induced pathology and immunology in the lung," *Am. J. of Respir. Cell and Mol. Biol.*, 23:62-70, 2000.

Matsumura et al., "Assessment of pathological changes associated with chronic allograft rejection and tolerance in two experimental models of rat lung transplantation," *Transplantation.*, 59:1509-1517, 1995.

Morris and Bachinger, "Type XI collagen is a heterotrimer with the composition $(1\alpha,2\alpha, 3\alpha)$ retaining non-triple helical domains," *J. Biological Chem.*, 262:11345-11350, 1987.

Murphy et al., "Inhibition of allorecognition by a human class II MHC-derived peptide through the induction of apoptosis," *J. Clin. Invest.*, 103:859-867, 1999.

Nösner et al., "HLA-derived peptides which inhibit T cell function bind to members of the heat-shock protein 70 family," *J. Exp. Med.*, 183:339-348, 1996.

Oluwole et al., "Induction of transplantation intolerance to rat cardiac allografts by intrathymic inoculation of allogeneic soluble peptides," *Transplantation*, 56(6):1523-1527, 1993.

Prop et al., "Lung allograft rejection in the rat. I. Accelerated rejection caused by graft lymphocytes," *Transplantation*, 40:25-30, 1985.

Prop et al., "Lung allograft rejection in the rat. II. Specific immunological properties of lung grafts," *Transplantation*, 40:126-131, 1985.

Regis et al., "Fas-ligand, tumor necrosis factor-alpha expression, and apoptosis during allograft rejection and tolerance," *Transplantation*, 66(7):887-893, 1993.

Sayegh et al., "Mechanisms of T cell recognition of alloantigen," *Transplantation*, 57:(9)1295-1302, 1994.

Sayegh and Krensky, "Novel immunotherapeutic strategies using MHC derived peptides," *Kidney Int. Suppl.* 53:S13-20, 1996.

Sayegh et al., "Down-regulation of the immune response to histocompatibility antigens and prevention of sensitization by skin allografts by orally administered alloantigen," *Transplantation*, 53:163-166, 1992.

Sayegh et al., "Induction of immunity and oral tolerance with polymorphic class II major histocompatibility complex allopeptides in the rat," *Proc. Natl. Acad. Sci.*, 89: 7762-7766, 1992.

Sekine et al., "Role of passenger leukocytes in allograft rejection—Effect of depletion donor alveolar Macrophages on the local production of TNF-alpha, T helper 1/Thelper 2 cytokines, IgG subclasses, and pathology in a rat model of lung transplantation," *J. Immunol.*, 159:4084-4093, 1997.

Seyer and Kang, Covalent structure of collagen: amino acid sequence of three cyanogen bromide-derived peptides from human alpha 1(V) collagen chain. *Arch. Biochem. Biophys.* 271(11): 120-129, 1989.

SivaSai et al., "Indirect recognition of donor HLA class I peptides in lung transplant recipients with bronchiolitis obliterans syndrome," *Transplantation.* 67(8):1094-1098, 1999.

Smith Jr, et al., "Interaction of proteoglycans with pericellular (1 $\alpha$, 2 $\alpha$, 3 $\alpha$) collagens of cartilage," *J. Biol. Chem.*, 260:10761-10767, 1985.

Strober and Coffman, "Tolerance and immunity in the mucosal immune system," *Res. Immunol.*, 148:489-498, 1997.

Trulock, "Lung transplantation," *Am. J. Respir. Crit. Care Med.*, 155:789-818, 1997.

VanBuskirk et al., "Patterns of allosensitization in allograft recipients: long-term allograft acceptance is associated with active alloantibody production in conjunction with active inhibition of alloreactive delayed-type hypersensitivity," *Transplantation.*, 65:1115-1123, 1998.

Westra et al., "A paradox in heart and lung rejection," *Transplantation*, 49:826-828, 1990.

Whitacre et al., "Oral tolerance in experimental autoimmune encephalomyelitis. III. Evidence for clonal anergy," *J. Immunol.*, 147:2155-2163, 1991.

Wilkes et al., "Allogeneic bronchoalveolar lavage cells induce the histology and immunology of lung allograft rejection in recipient murine lungs. Role of ICAM-1 on donor cells," *Transplantation*, 67(6):890-896, 1999.

Wilkes et al., "Allogeneic bronchoalveolar lavage cells induce the histology of acute lung allograft rejection, and deposition of IGg2a in recipient murine lungs," *J. Immunol.*, 155:2775-2783, 1995.

Wilkes et al., "Instillation of allogeneic lung macrophages and dendritic cells cause differential effects on local IFY-$\gamma$ production, lymphocytic bronchitis, and vasculitis in recipient murine lungs," *J. Leukoc. Biol.* 64:578-586, 1998.

Wilson et al., "Shared amino acid sequences between major histocompatibility complex class II glycoproteins, type XI collagen and *Proteus mirabilis* in rheumatoid arthritis," *Ann. Rheum. Dis.*, 54:216-220, 1995.

Woessner Jr., "The determination of hydroxyproline in tissue and protein samples containing small proportions of this immino acid," *Arch. Biochem. Biophys.* 93:440-447, 1961.

Yagyu et al., "Comparison of mononuclear cell populations in brochoalveolar lavage fluid in acute rejection after lung transplantation and *Mycoplasma* infection in rats," *J. Heart Transplant.*, 9:516-525, 1990.

Yamagami et al., "Suppression of allograft rejection with anti-alpha beta T cell receptor antibody in rat corneal transplantation," *Transplantation*, 67:600-604, 1999.

Yoshino et al., "Suppression of antigen-induced arthritis in Lewis rats by oral administration of type II collagen," *Arthritis Rheum.* 38:1092-1096, 1995.

Yousem et al., "Revision of the 1990 working formulation for the classification of pulmonary allograft rejection: Lung rejection study group," *J. Heart Lung Transplant*, 15:1-15, 1996.

Zheng et al., "CTLA4 signals are required to optimally induce allograft tolerance with combined donor-specific transfusion and anti-CD154 monoclonal antibody treatment," *J. Immunol.*, 162:4983-4990, 1999.

* cited by examiner

ORAL TOLERANCE INDUCTION BY COLLAGEN TO PREVENT ALLOGRAFT REJECTION

This application is a continuation of PCT Application No. PCT/US01/08680 filed Mar. 15, 2001, which claims priority to U.S. Provisional Patent Application Ser. No. 60/189,420 filed Mar. 15, 2000, the entire disclosures of which are incorporated herein by reference without disclaimer.

This invention made with goverment support under HL03885, AR20582-18, T35M HL07802and HL60797 awarded by the National Institutes of Health. The government has certain rights of the invention.

BACKGROUND OF THE INVENTION

1. Field of the Invention

The present invention relates generally to the fields of immunology, transplantation, graft rejection, and immunotolerance. More particularly, it concerns the use of collagen compounds to down regulate immune responses to such as those that result in allograft rejection.

2. Description of Related Art

Transplantation protocols are well-accepted in the medical community. For example, lung transplantation is a therapeutic modality for the treatment of many end stage pulmonary diseases. However, transplant rejection occurs more often in the lung as compared to other solid organ allografts. The leading cause of death in lung allograft recipients is chronic rejection, known as bronchiolitis obliterans (BO) (Trulock, 1997; Westra et al., 1990). The pathogenesis of chronic rejection is poorly understood; however the risk of developing chronic rejection is believed to be related with repeated acute rejection episodes.

Rejection of allografts is presently understood to be initiated by the recognition of allogeneic (i.e. donor) major histocompatibility complex (MHC) molecules by recipient/host T-lymphocytes leading to upregulated cellular and humoral immunity (Sayagh et al., 1994). The MHC antigens are typically presented to the recipient T-lymphocytes by antigen presenting cells (APC's), such as macrophages and dendritic cells. (Trulock, 1997; Heidler et al. 2000). Although immunosuppressive compounds may be used in an attempt to modulate rejection, immunosuppressive agents often fail to prevent continued rejection episodes. Thus, other methods for inducing indefinite acceptance of the allograft, also known as induction of immunological tolerance, are sought.

Allogeneic MHC molecules are the stimulus and target of the immune response during rejection. Therefore, MHC-derived peptides or synthetic peptides that may be homologous to MHC antigens have been the focus of investigations attempting to induce immunological tolerance to allografts (Krensky and Clayberger, 1997; Oluwole et al., 1993). In addition, a very recent study reports the induction of tolerance to multiple allogeneic MHC molecules in vitro by a non-polymorphic synthetic peptide derived from MHC molecules (Murphy et al., 1999). However, none of these reports appear to have resolved the issues of allograft rejection, and, in particular lung allograft rejection.

Since recognition of polymorphic regions of donor MHC molecules is usually the stimulus for allo-immune responses, immunological tolerance induced by peptides derived from the donor MHC is often specific to the allele of the donor MHC molecules. Therefore, identification of proteins/peptides that are highly conserved amongst individuals and induce immunologic tolerance across multiple MHC alleles may be of great benefit for the allograft recipient. However, the use of such proteins/peptides for induction of immunological tolerance to lung allografts has not been evaluated. Further, no proteins/peptides that are useful for such tolerance have yet been identified.

Further, despite the existence of different techniques to induce tolerance to solid organ allografts, such as donor specific blood transfusion, thymic injection with donor-derived APC's, or systemic immunization with peptides derived from donor MHC molecules prior to transplantation (Krensky and Clayberger, 1997), for any of these techniques to be effective the specific donor MHC molecules must be known several weeks prior to transplantation to allow sufficient time, i.e., weeks to months, for tolerance induction to occur. However, in the typical scenario only a few hours exist between the identification of a potential donor and the transplantation surgery, and therefore, time is not available for tolerance induction by these techniques.

Thus, there is acute need for developing methods that can induce tolerance to any possible donor tissue, irrespective of the MHC-type, prior to the identification of a suitable transplant donor.

SUMMARY OF THE INVENTION

In the present invention the inventors overcome deficiencies in the art by demonstrating the ability of collagen proteins in general, and type V collagen (also described herein as col(V)) to induce tolerance and prevent rejection of allografts. Col(V) is a molecule that is highly conserved amongst individuals and that may be homologous to MHC molecules. The inventors contemplate that prior treatment of prospective transplant recipients with the collagens, and in specific cases col(V), that are not derived specifically from the MHC molecule of the organ donor will provide preventive-therapy to prevent rejection in lung allograft recipients despite incompatibilities between the MHC molecules of the donor and recipient.

Thus, in one embodiment the present invention describes methods for inducing tolerance to an allograft comprising administering to a transplant recipient a molecule that suppresses alloimmune responses. In one aspect of the method, the molecule is administered prior to receipt of the allograft. In a specific embodiment, the allograft is a lung allograft. In one aspect of this embodiment, the administering is by intrapulmonary instillation into the recipient. In a preferred aspect of this embodiment, the administering is by oral feeding. The oral administration of the molecule can be repeated at a frequency of every alternate day for four days; or every alternate day for eight days, or, depending on the subject, feeding may be necessary for other periods of time. In preferred aspects, the subject will receive the molecule at least three times per month while on the transplant list. In other aspects, the subject will receive the molecule at least three times per month for at least two months following the transplant.

In one embodiment, the molecule can further comprise MHC-like domains. In another embodiment, the molecule is a collagen molecule. In a preferred aspect, the collagen is a collagen type V. In other aspects the collagen is a collagen type II; a collagen type XI; a collagen type IV; a collagen type III; and/or a collagen type I.

In another embodiment, the invention describes methods for preventing the induction of immune rejection response against a transplanted allograft comprising administering collagen to a transplant recipient. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

In yet another embodiment, the invention describes methods downregulating proliferative responses of lung T-lymphocytes to donor alloantigens in a transplant recipient following transplantation of allograft comprising administering collagen to the recipient. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

In further embodiments, the invention describes methods for inhibiting apoptosis in a transplant recipient following transplantation of an allograft comprising administering collagen to the recipient. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

In yet other embodiments, the invention describes methods for increasing the TNF-α production in a transplant recipient following transplantation of an allograft comprising administering collagen to the recipient. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

In still other embodiments, the invention describes methods of preventing the rejection of a transplanted allograft in a human patient comprising administering collagen to the patient. In one aspect, the rejection is an acute rejection episode, while in other aspects, the rejection is chronic rejection of the transplanted allograft. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

In yet another embodiments, the invention describes methods of preventing pleural disease in a human subject having received, or needing to receive, a transplanted allograft, comprising administering collagen to the patient. In a specific aspect of the method, the transplanted allograft is a lung allograft. In one aspect, the collagen is administered prior to receipt of the allograft. In another aspect the administering is by intrapulmonary instillation into the recipient. In a preferred aspect, the administering is by oral feeding. In specific aspects the collagen is a collagen type V. Alternatively the collagen may be a collagen type II; a collagen type XI; a collagen type IV; a collagen type III; and/or a collagen type I.

Thus, the methods described herein demonstrate that prior treatment of prospective transplant recipients with the collagens, and in specific cases col(V), that are not derived specifically from the MHC molecule of the organ donor will provide preventive-therapy for lung allograft rejection in recipients despite incompatibilities between the MHC molecules of the donor and recipient. In preferred aspects the prior treatment is by oral feeding and therefore by the induction of oral tolerance in the recipients. It is envisioned that these methods will provide effective preventive-therapy to human patients that require transplantation, particularly lung transplantation, by preventing post-transplant graft rejections that are generally fatal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows peribronchiolar and perivascular mononuclear cell infiltrates in lungs of BALB/c mice that received instillations of BAL cells from C57BL/6 mice. Similar pathologic lesions were observed in lungs of BALB/c mice that received weekly instillations of col(II) (FIG. 1B) or col(XI) (FIG. 1C) prior to instillations of C57BL/6 cells. Histology representative of 5-8 mice in each group (200× magnification).

FIG. 2A shows the presence of perivascular edema, but absence of perivascular or peribronchiolar mononuclear cell infiltrates in mice that received instillations of α1(V) prior to C57BL/6 BAL cells. FIG. 2B. shows similar histology in lungs of BALB/c mice that received instillations of α2(V) prior to instillations of C57BL/6 BAL cells. Histology representative of 5-8 mice in each group (200× magnification).

FIG. 7A shows normal histology in lungs of mice that received allogeneic cells alone for the first four weeks. FIG. 7B shows normal histology in lungs of mice that received allogeneic BAL cells, followed by instillations of col(II)-pulsed autologous BAL cells and similar findings in lungs of mice that received allogeneic BAL cells followed by instillations of col(XI)-pulsed autologous BAL cells (FIG. 7C). FIG. 7D shows that instillations of allogeneic BAL cells followed by instillations of col(V)-pulsed autologous BAL cells induced perivascular and peribronchiolar mononuclear cell infiltrates in recipient lungs. Tissue sections representative of 5 mice in each group (200× magnification).

DESCRIPTION OF ILLUSTRATIVE EMBODIMENTS

A. The Present Invention

Figure 1B:
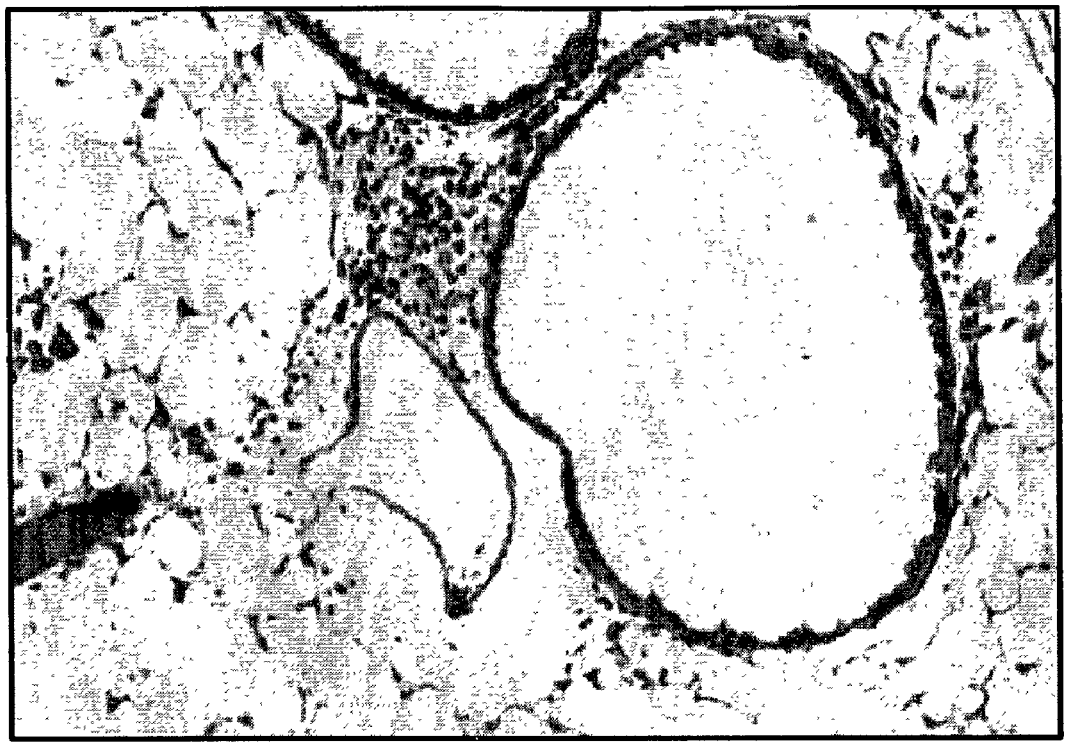
FIG. 1A, FIG. 1B, and FIG. 1C. Lung histology in BALB/c mice after four weekly instillations of $1.5 \times 10^5$ allogeneic (C57BL/6) BAL cells alone, col(II), or col(XI) (50 µg each) weekly for four weeks followed by four weekly instillations of C57BL/6 BAL cells.

The present invention describes methods for the induction of oral tolerance to MHC-"like" molecules. Examples of such molecules include the collagens, in particular, type V collagen [col(V)], which has been shown to reduce the incidence of lung allograft transplant rejection following lung transplantation. These methods allow the induction of tolerance towards MHC molecules in general and thereby allows successful transplantation of tissue in a recipient irrespective of the MHC-type of the donor.

The present invention overcomes this deficiency as one can induce tolerance in a recipient by oral feeding of col(V) while awaiting the identification of a donor for lung transplantation. The inventors also contemplate the use of other MHC-"like" peptides in addition to col(V), that are not derived specifically from the MHC molecule of the organ donor as potential therapy to prevent rejection in lung and other organ allograft recipients. One of skill in the art will recognize that these methods will induce tolerance despite the incompatibilities between MHC molecules of the donor and recipient.

B. Collagen Type V

Collagen type V [col(V)] is a minor collagen present in the lung (Madri and Furthmayr, 1980) and is located in the peribronchiolar connective tissues (Madri and Furthmayr, 1979), alveolar interstitium (Konomi et al., 1984), and capillary basement membranes (Madri and Furthmayr, 1979). The α-1 chain of α1(V) is nearly 76% homologous to the α2-chain of type XI collagen [α2(XI)] (Cremer et al., 1994), and the gene for α2(XI) is located in the MHC class II loci of mice and humans (Hanson et al., 1989), and shares amino acid sequences with MHC class II (Wilson et al., 1995). MHC-derived peptides have been utilized to induce tolerance in allografts other than the lung. The present inventors selected col(V) to modulate immune responses in lung allografts due to the possible presence of MHC-"like" sequences in col(V).

C. Tolerance

The ability to induce tolerance to donor alloantigens (Krensky and Clayberger, 1997; Oluwole et al, 1993), or stimulation of "suppressor cells" (Strober and Coffman, 1997) is crucial to the prevention of allograft rejection. Tolerance may result from induction of anergy in T-lymphocytes to alloantigens, or clonal deletion of alloantigen-specific T-lymphocytes (Krensky and Clayberger, 1997; Oluwole et al., 1993). Since col(V) has MHC "like" sequences, instillations or oral feeding of col(V) prevents proliferative responses to alloantigens and prevents the development of acute rejection pathology in recipient lungs. Thus, col(V) may induce anergy to donor alloantigens; or alternatively, the lack of proliferative responses to donor antigens may be due to clonal deletion of alloantigen-specific lung lymphocytes; or yet alternatively may result from suppressor cell activity.

The induction of anergy or clonal deletion may vary relative to the use of peptides derived from MHC class I or class II molecules (Krensky and Clayberger, 1997; Oluwole et al., 1993). For example, proposed mechanisms for tolerance induced by MHC class I-derived peptides includes binding to heat shock proteins (Nosner et al., 1996), modulation of heme oxygenase activity (Iyer et al., 1998), or possible inhibition of natural killer cell activity (Krensky and Clayberger, 1997). MHC class II-derived peptides have been reported to induce tolerance by competition for target antigens during indirect allorecognition, blockade of cell cycle progression, and inhibition of CD4 receptor function (Krensky and Clayberger, 1997). More recently, (Murphy et al., 1999), reported that peptides from non-polymorphic regions of HLA-DQA1 inhibited allo-immune responses by possible blockade of MHC class II molecules which induced apoptosis in responding lymphocytes.

Oral administration of antigens is an effective method of inducing peripheral T-cell tolerance. This phenomenon, often referred to as oral tolerance, has been well studied in various models of autoimmune diseases in animals including encephalomyelitis, uveitis, diabetes, myasthenia gravis, and arthritis. However, the mechanisms for inducing tolerance are not completely understood. All of the known mechanisms for tolerance induction, including clonal anergy, clonal deletion, and regulation by IL-4, IL-10, or TGF-beta-mediated active suppression may have a role in oral tolerance (Faria and Weiner, 1999). Generally, higher doses of antigen are reported to induce anergy or clonal deletion (Chen et al., 1995; Whitacre et al., 1991), whereas low doses induce cytokine regulation and active suppression (Faria and Weiner, 1999; Chen et al., 1994). In the animal model of cardiac transplantation, oral administration of allogeneic splenocytes has been shown to be effective in tolerance induction by bypassing Th1 activation and selectively stimulating induction of Th-2 derived inhibitory cytokines such as IL-4 (Hancock et al., 1993; Ishido et al., 1999).

Immunological tolerance to the allograft may be induced by immunizing the recipient orally with donor-derived MHC proteins/peptides or MHC-"like" proteins prior to transplantation (Sayegh et al., 1996; Hancock et al. 1993; Ishido et al. 1999; Sayegh et al. 1992a; Sayegh et al. 1992b). This phenomenon, known as oral tolerance (Faria and Weiner 1999; Mayer 2000; Garside and Mowat 1997), abrogates the rejection response. Although donor MHC-antigens are the stimulus and target of the rejection response (Trulock 1997; Heidler et al. 2000), we have recently reported that type V collagen [col(V)], which may be MHC-"like", is also recognized as an antigen during lung allograft rejection in humans (Wilkes et al. Submitted), and the local immune response to lung alloantigens in mice (Heidler et al. 2000). Significantly, immunization with col(V) induces tolerance to lung alloantigens in mice (Heidler et al. 2000).

Studies of tolerance have focused primarily on the effect of the tolerizing antigen on T-lymphocyte function, and the role of T-lymphocytes in suppressing immune activation (Faria and Weiner 1999; Mayer 2000; Garside and Mowat 1997). However, immune responses to any antigen require interactions between APC's and T-lymphocytes, and the T-lymphocyte may affect APC function (Liu et al. 1999; Li et al. 1999; Lederman and Siciu-Foca 1999). Therefore, down-regulated antigen presentation by APC's from tolerized hosts could contribute to tolerance induction either indirectly as a result of interactions with suppressor T-lymphocytes, or possibly as a result of direct effects of the tolerizing antigen on the APC.

The present inventor is one of the few that has developed the rat model of lung allograft rejection (Yasufuku et al. Submitted, Sekine et al. 1997) in which F344 rat lungs ($RT1^{1v1}$) are transplanted orthotopically into WKY ($RT1^1$) recipients. Similar to human lung allograft rejection (Wilkes et al. Submitted), and the local immune response to lung alloantigens in mice (Mares et al. In Press), WKY rats develop an immune response to col(V) during rejection of F344 lung allografts (Yasufuku et al. Submitted). However, the ability of col(V) to induce oral tolerance and prevent the immunology and pathology of acute and chronic rejection is unknown, and the role of T lymphocytes and antigen presenting cells in this process have not been previously investigated. Utilizing the rat lung transplant model developed by the present inventor, it has been shown that oral tolerance induction by col(V) prevents the immunology and pathology of lung allograft rejection.

The present inventor has shown that type V collagen [col(V)], which may be MHC-"like", is also recognized as an antigen during lung allograft rejection in humans (Wilkes et al. Submitted), and the local immune response to lung alloantigens in mice (Mares et al. In Press). Also, immunizing mice with col(V) induces immunological tolerance to lung alloantigens (Mares et al. In Press). The ability of col(V) to induce oral tolerance and prevent the immunology and pathology of acute and chronic lung allograft rejection has been previously unknown.

D. Immune Response

The present inventor has developed a murine model in which repeated instillations of allogeneic lung APC's (macrophages and dendritic cells) induces the histology and immunology similar to acute lung allograft in recipient lungs (Heidler et al. 2000; Mares et al. 2000; Wilkes et al. 1998; Wilkes et al. 1995; Wilkes et al. 1999). Data from these studies have confirmed that MHC antigens expressed on the donor cells are the stimulus for the rejection-"like" response in recipient lungs (Heidler et al. 2000). Immunizing mice with col(V) prior to challenge with lung alloantigen abrogates local alloimmune responses (Mares et al. In Press). Data showing that human lung allograft recipients develop an immune response to col(V) (Wilkes et al. Submitted) also provide direct evidence that the local immune response to allogeneic MHC's also involves an immune response to col(V). These data and the fact that donor MHC antigens are the stimulus of the rejection response suggests that col(V) may be MHC-"like". Regions of col(V) are nearly 80% homologous to regions of collagen type XI [col(XI)] (Cremer et al. 1994). One of the genes for col(XI) maps within the MHC class II gene of mice and humans (Trowsdale et al. 1994; Liu et al. 1996), and has homologous amino acid sequences to MHC class II (Wilson et al. 1995). Interestingly, a recent report showed that immune responses to col(XI) had key roles in the rejection of nasal cartilage grafts (Bujia et al. 1994). These data demonstrate that immune responses to proteins or peptides that are homologous to MHC molecules or are MHC-"like" may contribute to alloreactivity. In the lung col(V), is located in the perivascular and peribronchiolar tissues which are the targets of the rejection response. The present inventor is the first to show that feeding col(V) down regulates lung allograft rejection in rats (Yasufuku et al. Submitted).

Immunological tolerance is defined as immune unresponsiveness to an antigen implicated in causing disease. Although tolerance may be induced by administering antigens by different routes, oral tolerance refers to the oral administration of the antigen, which has resulted in suppression of disease activity in several animal models including experimental autoimmune encephalomyelitis-a rodent model of multiple sclerosis, myasthenia gravis, uveitis, insulin dependent diabetes, and collagen-induced arthritis (Faria and Weiner 1999). Early results from clinical trials in humans suggest that oral tolerance is effective in autoimmune uveitis, diabetes, nickel allergy, and possibly multiple sclerosis (Faria and Weiner 1999; Duda et al. 2000). There are few studies reporting oral tolerance induction in organ transplantation (Sayegh et al. 1996; Hancock et al. 1993; Ishido et al. 1999; Sayegh et al. 1992a; Sayegh et al. 1992b). In each report, tolerance was induced by feeding donor MHC-derived peptides or feeding allogeneic cells prior to transplantation (Sayegh et al. 1996; Hancock et al. 1993; Ishido et al. 1999; Sayegh et al. 1992a; Sayegh et al. 1992b). These techniques were effective in preventing rejection of cardiac and corneal allografts (Sayegh et al. 1996; Hancock et al. 1993; Ishido et al. 1999; Sayegh et al. 1992a; Sayegh et al. 1992b; Faria and Weiner 1999). In addition to diminished disease activity, immune suppression induced by oral tolerance in these studies was also quantitated by down regulation of delayed type hypersensitivity (DTH) responses to target antigens, as well as diminished cellular and humoral immunity (Faria and Weiner 1999; Mayer 2000; Garside and Mowat 1997).

There are three mechanisms by which oral tolerance down regulates antigen-specific immune responses: 1. active suppression of antigen specific cells, 2. clonal anergy of antigen specific cells, and 3. clonal deletion of antigen specific cells (Faria and Weiner 1999, Miller et al. 1991; Chen et al. 1994; Chen et al. 1995). Although all three mechanisms can be operative simultaneously in response to oral tolerance, active suppression and clonal anergy are the key mechanisms of immune suppression induced by oral tolerance (Faria and Weiner 1999).

Active suppression describes the regulation of one lymphocyte subset by another in an antigen-specific manner. Depending on the antigen and disease state, the suppressor cells may be CD4+ and/or CD8+ T-lymphocytes which migrate from peripheral lymphoid tissues, such as spleen and peripheral lymph nodes, to sites of disease activity.

Adoptive transfer of these cells to naïve recipients has confirmed the role of these cells in active suppression in rodent models of ovalbumin-induced hypersensitivity, and multiple sclerosis. In vitro evidence of active suppression is demonstrated by data showing that tolerized lymphocytes from animals can suppress proliferation of other antigen-specific T-lymphocytes across a transwell cell culture system (Faria and Weiner 1999; Miller et al. 1991).

Clonal anergy refers to unresponsiveness of antigen-specific T-lymphocytes, which is characterized by diminished proliferation after exposure to an antigen, and is involved in oral tolerance in several animal models. Anergy could be the result of production of soluble suppressive factors by CD4+ or CD8+ T-lymphocytes themselves, other T-lymphocytes or cells in the local environment, or as result of decreased expression of appropriate costimulatory molecules (Faria and Weiner 1999). Clonal deletion refers to the elimination of antigen-specific T-lymphocytes, but has been reported rarely as a mechanism of oral tolerance to an antigen (Chen et al. 1995).

The soluble mediators that suppress the immune response during oral tolerance are derived mainly from regulatory or suppressor T-lymphocytes (Faria and Weiner 1999). There are four types of T-lymphocytes described by the cytokines they produce: Th1-type that produce interleukin-2 (IL-2) and gamma interferon (γIFN); Th2-type that produce IL-4 and IL-10; Th3-type that produce high levels or transforming growth factor beta (TGF-β), alone, or in conjunction with very low levels of IL-4, IL-10, or γIFN; and Tr1 cells that produce high levels of IL-10 in conjunction with low levels of TGF-β (Faria and Weiner et al. 1999; Mayer 2000; Garside and Mowat 1997; Groux et al. 1997). Since Th3, Th2, and Tr1-T-lymphocytes have been shown to be the major mediators of active suppression induced by oral tolerance, then TGF-β, IL-4 and IL-10 are believed to be key cytokines in this process (Teng et al. 1998; Shi et al. 1999b). A report from Barone et al., and others showing that oral tolerance induction occurred in the absence of these cytokines suggests that other mediators or cells could suppress the immune response (Barone et al. 1998; Shi et al. 1999a). However, cytokines produced by regulatory T-lymphocytes that down regulate lung allograft rejection in response to col(V)-induced tolerance are unknown.

Although studies of oral tolerance have focused on T-lymphocyte-derived cytokines that suppress immune responses, nitric oxide, which is not produced by T-lymphocytes, is known to be a potent suppressor of alloimmmune responses (Garside and Mowat 1997). These data and others showing that nitric oxide modulates apoptosis, which is involved in the rejection response (Meyer et al. 1998; Kallio et al. 1997; Shiraishi et al. 1997; Shiraishi et al. 1995; Medot-Pirenne et al. 1999), suggests that nitric oxide could be a mediator of oral tolerance and prevent the rejection response. TGF-β, is a potent inducer of nitric oxide synthesis, and is a key mediator of active suppression in oral tolerance (Faria and Weiner 1999; Meyer et al. 1998; Vodovotz et al. 1998; Vodovitz et al. 1999). Therefore, immunosuppression induced by TGF-β in the tolerized host could be mediated, in part, by nitric oxide. However, production of nitric oxide in response to oral tolerance is unknown.

Another possible mediator of active suppression, which is not produced by T-lymphocytes, is connective tissue growth factor (CTGF). Produced by fibroblasts and endothelium in response to TGF-β, CTGF has been shown to be the key effector molecule of TGF-β-induced proliferation of connective tissues and endothelium (Mori et al 1999; Grotendorst 1997). There are no data regarding effects of CTGF on cellular and humoral immunity. However, very recent studies show that CTGF may suppress proliferation in malignant cells and myocytes (Kishikawa et al. 1999a; Kishikawa et al. 1999b; Kishikawa et al. 2000). Since suppression of cellular proliferation is important in preventing allograft rejection, then TGF-β-induced production of CTGF could contribute to suppression of alloimmmune responses during oral tolerance.

Antigen-specific T-lymphocyte activation induced by APC's requires bi-directional interaction between the T-lymphocyte and APC. Initially, APC's present MHC molecules that bind to the T-cell-receptor which stimulates upregulated expression of CD40-ligand (CD40L) on T-lymphocytes. CD40L, in turn, binds to its receptor, CD40, on the APC. Signaling through CD40 induces the expression of CD80 and CD86 on the APC which, upon binding to their receptor, CD28, on the T-lymphocyte, results in co-stimulation and subsequent T-lymphocyte activation (Liu et al. 1999; Li et al. 1999; Lederman and Siciu-Foca 1999). Although studies of oral tolerance induction have focused on T-lymphocyte function, a recent study from Taams et al (1998), reported that tolerance induction may affect function of APC's, with similar data from other investigators (Wu et al. 1998; Finkelman et al. 1996; Viney et al. 1998). For example, a report from Wu. et al (1998), showing that expression of CD80 is decreased on APC's from the lymph nodes and spleens of orally tolerized mice suggests that ineffective APC's could contribute to impaired T-lymphocyte activation in tolerized recipients. Furthermore, studies in vitro showing that suppressor T-lymphocytes inhibit expression of CD86 in APC's highlights another mechanism of how tolerance induces impaired APC function (Liu et al. 1999; Li et al. 1999; Lederman and Siciu-Foca 1999). Therefore, oral tolerance induced by col(V) could prevent rejection episodes by down-regulating APC function, directly, or through interactions with tolerized T-lymphocytes. Alternatively, macrophages and dendritic cells could suppress alloimmune responses in tolerized lung allograft recipients by producing soluble mediators, such as TGF-β, nitric oxide, or IL-10. However, the effect of oral tolerance induction on antigen presentation by host APC's, i.e., macrophages and dendritic cells, to T-lymphocytes in lung allograft rejection has not been reported.

The basis for the preliminary data and proposed studies is the result of multiple experiments performed in a murine model that reproduces the immunology and histology of lung allograft rejection. In brief, repeated instillation of allogeneic (C57BL6, H-$2^b$, I-$a^b$) lung macrophages and dendritic cells into the lungs of recipient BALB/c mice (H-$2^d$, I-$a^d$) induces perivascular and peribronchiolar mononuclear cell infiltrates analogous to grade 2 acute rejection in recipient lungs. In addition, production of IL-2, γIFN, TNF-α and alloantibodies are upregulated locally, vascular endothelium and bronchiolar epithelium undergo apoptosis, and these mice develop immune responses to col(V) similar to human lung allografts during rejection (Mares et al. In Press). Furthermore, the immunologic and pathologic "rejection" response is dependent on expression of either MHC class I or II on the donor cells (Heidler et al. 2000). Instillation of col(V), but not col(II) or col(XI), into the lung prior to instillations of allogeneic cells abrogates development of rejection pathology, down regulates production of γIFN and TNF-α, induces anergy in recipient T-lymphocytes, and prevents apoptosis in vascular endothelium and bronchiolar epithelium. Col(II) and col(XI) were controls for col(V) for these studies (Mares et al. In Press). Col(II) is found in articular cartilage, is not present in the lung, and is not homologous to col(V). In contrast col(XI) has homology to col(V), but similar to col(II), it is found in articular cartilage and is not present in the lung (Cremer et al. 1994).

Systemic immune responses to antigens in rodents may be quantitated by delayed-type hypersensitivity (DTH) responses to the antigens (Christou et al. 1984; Henningsen et al. 1984). It is known that in organ transplantation, allograft recipients develop DTH responses to donor alloantigens during acute rejection (Henningsen et al. 1984). To determine the specificity of the DTH response to alloantigens and col(V), the present inventor also determined DTH responses to col(II), col(XI), and third party antigens, i.e., Brown Norway (BN) rat antigens (RT1″) (Example 3). Utilizing a modification of procedures described by Sayegh et al. (1992b), Yoshino et al. (1995), and Yamagami et al. (1999), DTH responses to donor (F344) antigens, col(V), BN antigens, col(II), and col(XI) were determined two weeks after transplantation of F344 lung allografts into WKY recipients, the time at which severe rejection acute rejection begins to develop (Matsumura et al 1995; Zuo et al. 1995). In brief, naïve (non-transplanted) or allograft recipient WKY rats received $10^7$ irradiated (3000 rad) donor-derived F344, or third party (BN) splenocytes in 30 µl of PBS into the right pinnae by s.c. injection using a 26 gauge needle. Separate groups of naïve or allograft recipient WKY rats were injected into the right pinnae with either 15 µg of col(V), col(II), or col(XI) diluted in 30 µl of PBS. 30 µl of PBS (control for the test antigens) were injected into the left pinnae of each rat in each group. The ear thickness was measured with a micrometer caliper (Mitutoyo, Field Tool Supply, Chicago, Ill.) in a blinded fashion immediately before and 24 hr after injection. Antigen-specific DTH responses were calculated according to the following formula: Specific ear swelling=(right ear thickness @ 24 hr–right ear thickness @ 0 hr)–(left ear thickness @ 24 hr–left ear thickness @ 0 hr)$\times 10^{-3}$ mm (Yamagami et al. 1999). All data is reported as the mean of triplicate measurements in 4 rats in each group. Utilizing this technique, specific ear swelling$>20 \times 10^{-3}$ mm is considered significant (Sayegh et al. 1992b; Yoshino et al. 1995; Yamagami et al. 1999).

Figure 13:
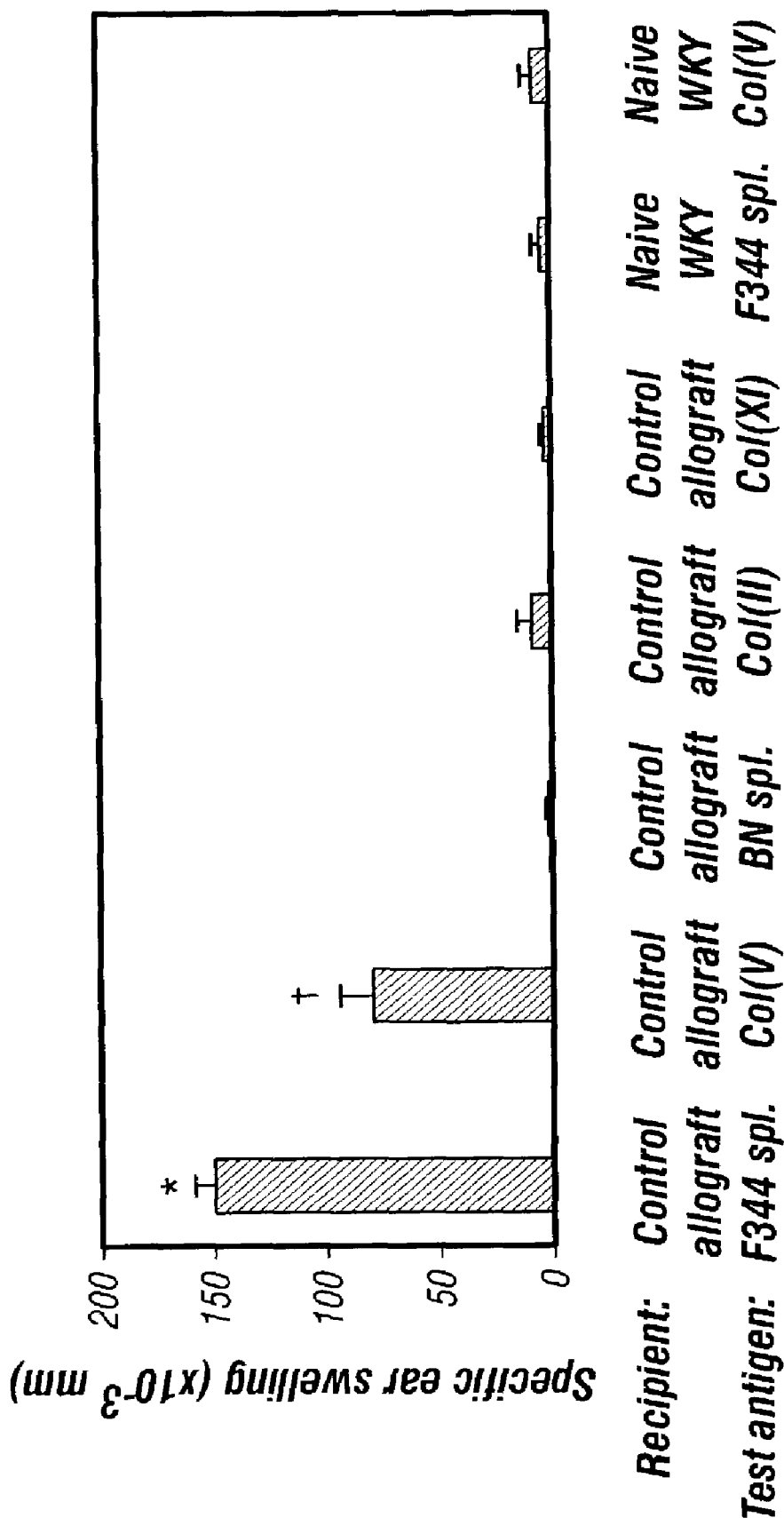
FIG. 13. DTH responses to donor alloantigens, col(II), col(V), col(XI), and third party alloantigens in control allograft recipients two weeks post-transplantation. Animals received $10^7$ irradiated (3000 rad) donor-derived F344 splenocytes, third party (BN) splenocytes, or 15 μg of col(II), col(V), or col(XI) into the right pinnae and diluent into the left pinnae. The ear thickness was measured with a micrometer in a blinded fashion immediately before and 24 hr after injection and the Specific Ear Swelling calculated as described in preliminary data. Data represent the mean±SEM of Specific Ear Swelling of four rats in each group. [*p<0.0001 compared to naïve WKY rats challenged with F344 splenocytes or col(V) and †p<0.0001 compared to naïve WKY rats challenged with col(V) or F344 splenocytes].

FIG. 13 shows that control allograft rats, i.e., WKY rats that received F344 lung allografts, develop strong DTH responses to F344 (donor) antigens and col(V) two weeks after transplantation [$^{*,\dagger}$p<0.0001 compared to naïve WKY rats tested with either F344 splenocytes or col(V)]. In contrast, WKY rats that received F344 allografts did not develop DTH responses to third party (BN) antigens, or collagens II or XI (FIG. 13). Naïve rats, i.e., those that did not receive lung allografts, did not have DTH responses to col(II), or col(XI). These data confirm prior other studies showing that DTH responses are indicative of immune activation during allograft rejection, which is specific to donor, but not third party, alloantigens (VanBuskirk et al. 1998). In addition, these studies confirm our reports in mice (Mares et al. In Press) and humans (Wilkes et al. Submitted) that col(V), but not col(II) or col(XI), is a target of the immune response during lung allograft rejection.

E. Prevention of Acute Rejection

To determine if immune cells from tolerized animals could transfer tolerance to naïve animals and prevent lung allograft rejection, splenic lymphocytes ($10 \times 10^8$ T-lymphocytes, >95% CD3+) from col(V)-fed WKY rats that received F344 lung allografts were adoptively transferred by tail vein injection to naïve WKY rats 24 hours prior to transplantation of F344 lung allografts. Two weeks post-transplant, the lungs were harvested, and rejection pathology assessed.

Figure 14B:
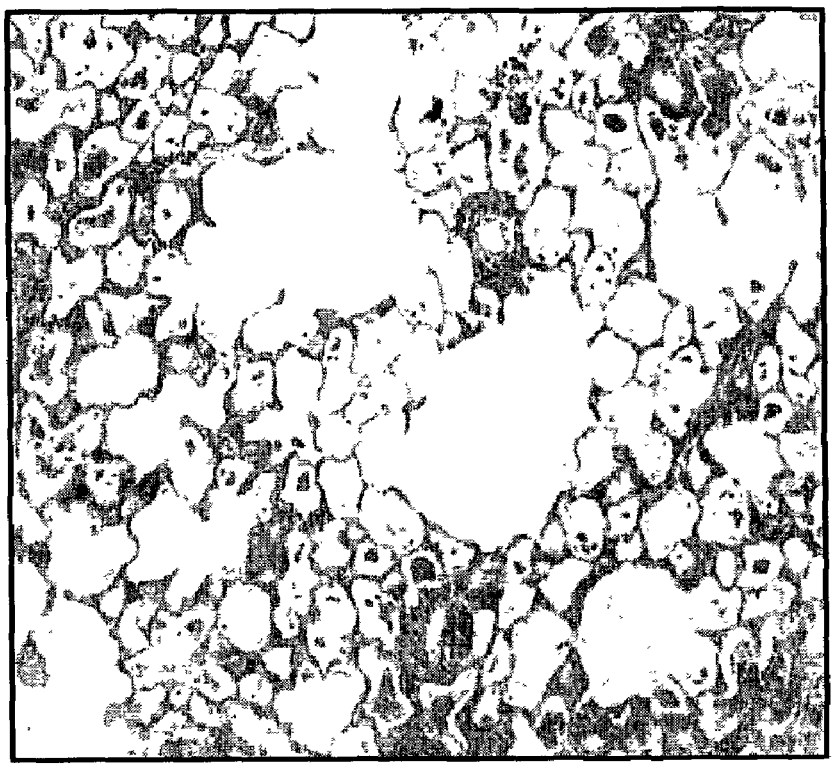
FIG. 14 Histology of control allografts (A) and recipients that received T-lymphocytes from tolerant WKY rats (B). Control allografts show extensive perivascular, peribronchial, and alveolar mononuclear cell infiltrates consistent with severe rejection (A). In contrast, adoptive transfer of tolerant T-lymphocytes resulted in moderate perivascular and peribronchial mononuclear cell infiltrates consistent with moderate rejection (B). Photomicrographs representative of five rats in each group (100× magnification). Tissues harvested two-weeks post-transplantation.
Figure 14A:

FIG. 14 shows that compared to untreated allograft recipients (FIG. 14A), adoptive transfer of splenic T-lymphocytes from tolerant rats down-regulated rejection pathology in naïve WKY rats (FIG. 14B). Adoptive transfer of naïve splenic T-lymphocytes to naïve rats prior to transplantation had no effect on rejection pathology. Collectively, these data show that oral tolerance induced by col(V) results in the development of regulatory cells, and that these cells are capable of suppressing lung allograft rejection when adoptively transferred to naïve recipients.

Figure 15:
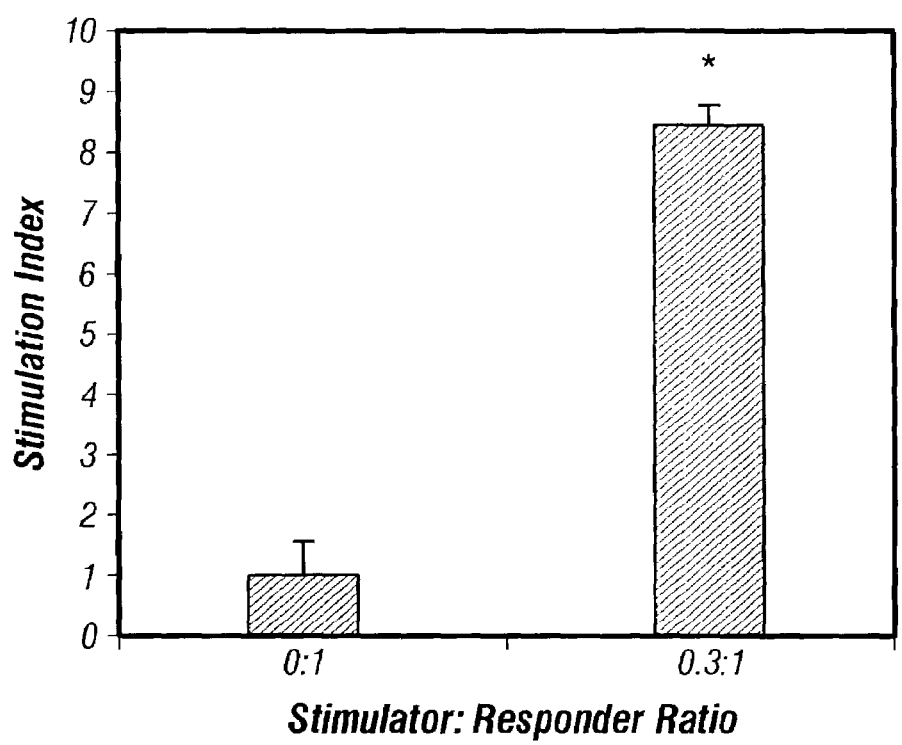
FIG. 15. Mixed leukocyte reaction. $0.9 \times 10^5$ mitomycin-C-treated F344 rat splenocytes (stimulators) were incubated with $3 \times 10^5$ T-lymphocytes (responders) isolated from lymph nodes of normal WKY rat (0.3:1 ratio). Eighteen hours prior to the completion of a 5-day incubation, the cells were pulsed with $^3$H-thymidine and proliferation determined by counts/minute (cpm) of thymidine incorporation. Stimulation index equals the multiples of proliferation in lymph node lymphocytes at stimulator:responder ratio or 0.3:1 relative to proliferation of lymph node lymphocytes alone (0:1) (cpm of lymphocytes alone=504±225). Data represent mean±SEM of three experiments (*p<0.05 compared to 0:1).

Many soluble factors that suppress immune activation may be produced systemically in response to oral tolerance (Faria and Weiner 1999; Mayer 2000; Garside and Mowat 1997). Utilizing mixed leukocyte reactions (MLR's), which measure allo-immune immune responses in vitro, it was determined whether serum from tolerized lung allograft recipients suppress immune responses to donor alloantigens. In brief, $3 \times 10^5$ lymph node T-lymphocytes (>95% CD3%) from normal WKY rats (responders) were cultured, alone, or with $0.9 \times 10^5$ mitomycin-C treated (Sigma, St. Louis, Mo.) adherent splenocytes (enriched for APC's) from normal F344 rats (stimulators) in 200 µl of complete media in 96 well flat bottom plates (Costar, Cambridge, Mass.) (Stimulator: responder ratio 0:1, and 0.3:1). Eighteen hours prior to the completion of a 5-day incubation, 1 µCi of $^3$H-thymidine was added to each well, proliferation determined by counts per minute of thymidine incorporation in triplicate cultures and reported as a Stimulation Index. FIG. 15 shows that F344 APC's induced brisk proliferative responses in WKY lymphocytes (*p<0.05).

Figure 16:
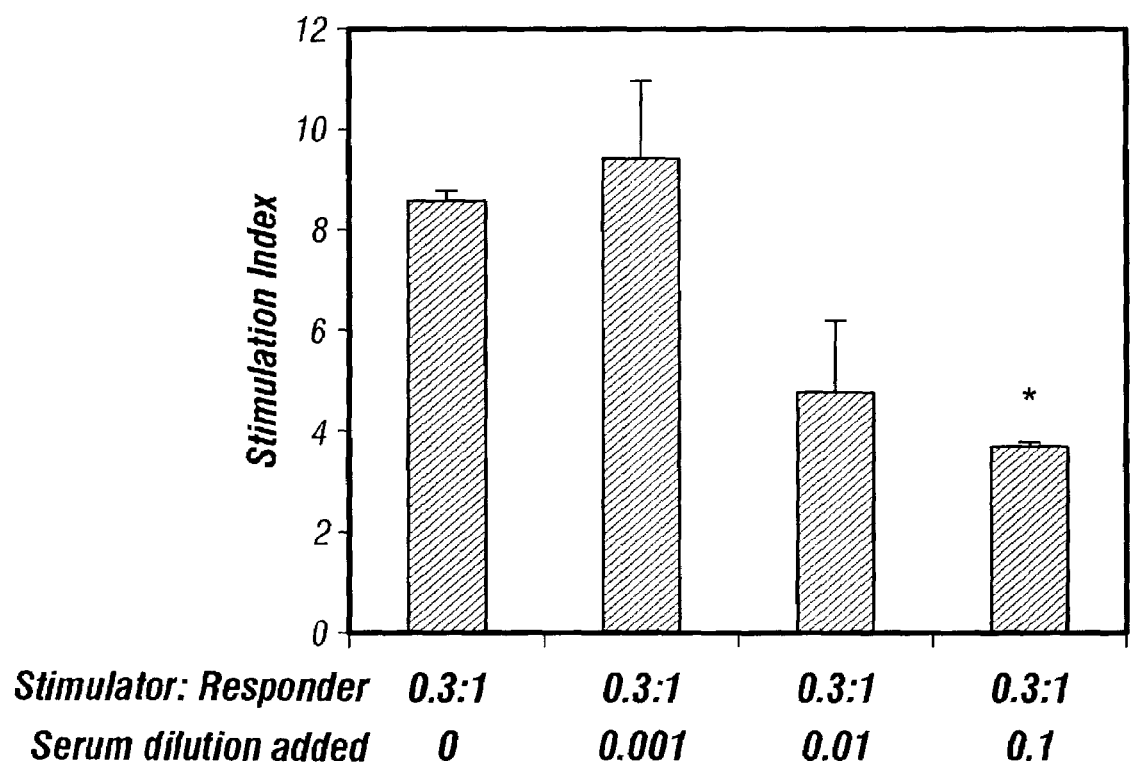
FIG. 16. Suppression of mixed leukocyte reaction with serum from col(V)-fed allograft rats. $0.9 \times 10^5$ mitomycin-C-treated F344 rat splenocytes (stimulators) were incubated with $3 \times 10^5$ normal WKY rat lymph node T-lymphocytes (responders) (0.3:1 ratio) along with different dilutions of serum from col(V)-fed allograft rats. Stimulator and responder cells were same as shown in FIG. 15. Eighteen hours prior to the completion of a 5-day incubation, the cells were pulsed with $^3$H-thymidine and proliferation determined by counts/minute (cpm) of thymidine incorporation. Stimulation index equals the multiples of proliferation in lymph node lymphocytes at stimulator:responder ratio of 0.3:1 relative to proliferation of lymph node lymphocytes alone. Data represent mean±SEM of three experiments (*p<0.05 compared to control).

To determine whether serum from tolerized lung allograft recipients suppressed alloimmune responses, the MLR studies were repeated with addition of varying dilutions of serum from normal WKY rats, allograft control-WKY rats, or col(V)-fed-allograft WKY rats to each well, followed by an assessment of the Stimulation Index. Serum was obtained from allograft control recipients or col(V)-fed allograft recipients two weeks post-transplantation. Serum was added in varying dilutions to each well—final total volume 200 µl/well. FIG. 16 shows serum from col(V)-fed allograft recipients abrogated lymphocyte proliferation in a dose dependent manner (*p<0.05). Addition of serum from normal rats or allograft control rats did not suppress lymphocyte proliferation.

Figure 17:
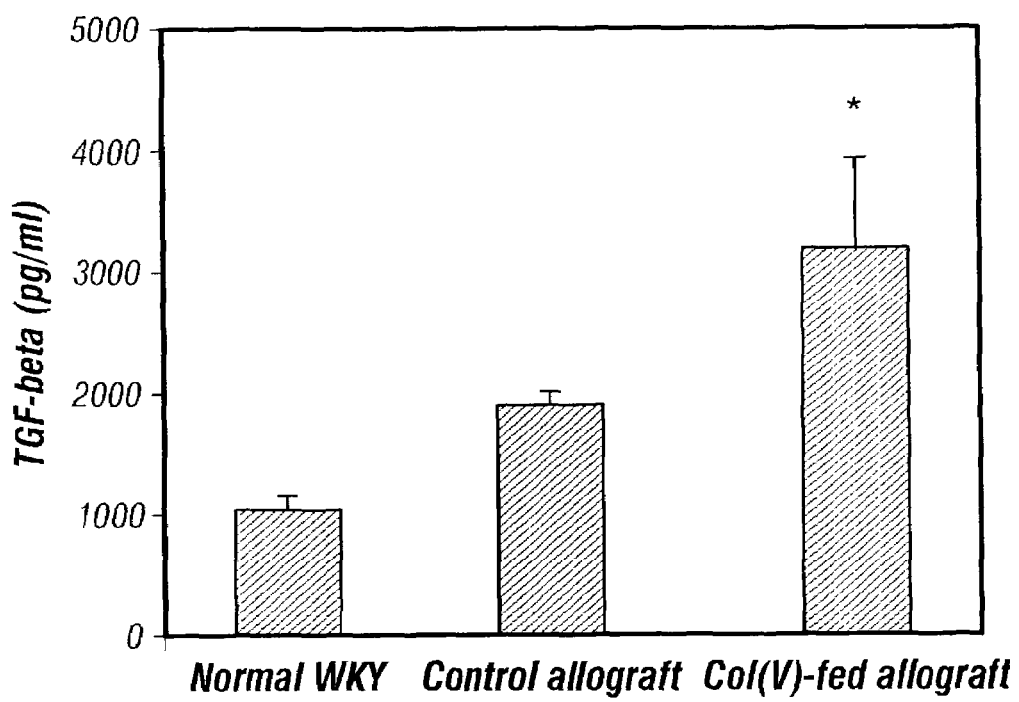
FIG. 17. TGF-β levels in serum of normal WKY rats, control allograft recipients, and col(V)-fed allograft recipients. Levels of TFG-β in serum were determined by ELISA. Data represent mean±SEM of four rats in each group. (*p<0.05 compared to control allografts).

Data in the prior section showed that serum from tolerant allograft recipients suppresses alloimmmune responses. TGF-β is cited most frequently as the cytokine responsible for suppressing immune responses in oral tolerance (Faria and Weiner 1999). Therefore, it was determined whether oral tolerance induced by col(V) is associated with upregulated production of TGF-β during lung allograft rejection. Utilizing commercial ELISA (R&D Systems, Minneapolis, Minn.), TGF-β was measured in serum of col(V)-fed WKY rats that received F344 lung allografts, compared to untreated WKY that received F344 lung allografts two weeks post-transplantation, and normal WKY rats. As expected, FIG. 17 shows that TGF-β is present in the serum of normal rats. Lung allograft rejection is associated with a slight increase in TGF-β. In contrast, TGF-β levels were upregulated markedly in serum of tolerant lung allograft recipients [col(V)-fed allografts] during rejection (FIG. 17) (*p<0.05 compared to control allografts).

Collectively, these data show that serum from tolerant rats suppress alloimmune responses in vitro. Oral tolerance has been shown to up regulate production of TGF-β systemically, and TGF-β has had a key role in suppressing activity during oral tolerance (Faria and Weiner 1999). Therefore, it is interesting to speculate that TGF-β is involved in col(V)-induced oral tolerance to lung allografts. However, the direct role of TGF-β or other cytokines or mediators in tolerance induction during lung allograft rejection is unknown.

Figure 18:
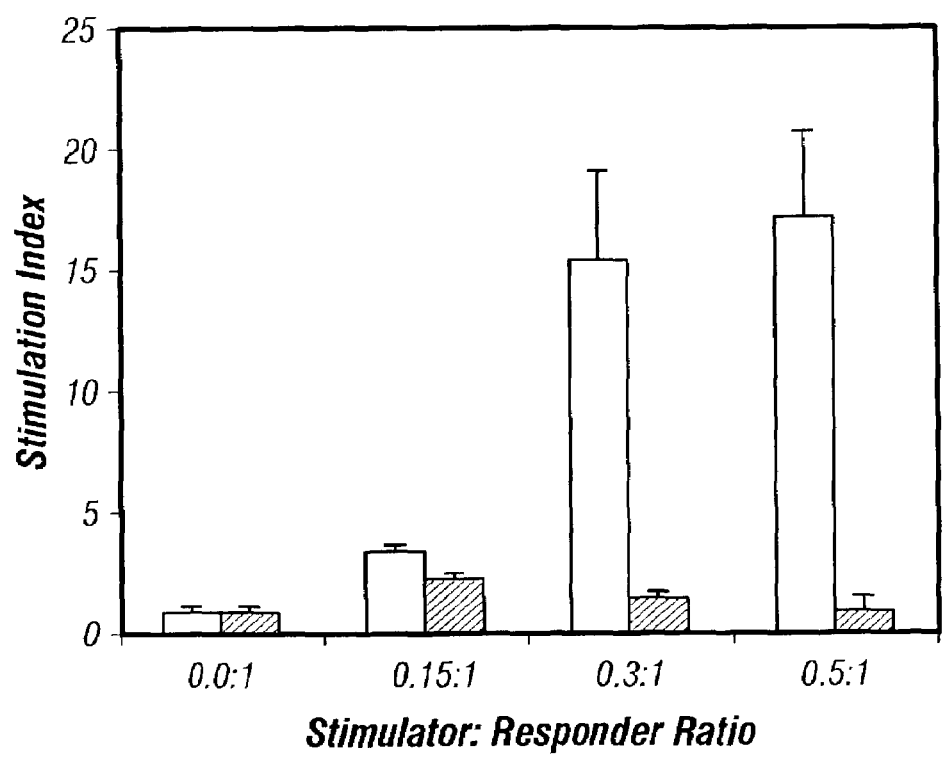
FIG. 18. Mixed leukocyte reaction. Mitomycin-C-treated normal WKY rat splenocytes or col(V)-fed allograft recipient splenocytes (stimulators) were incubated with $3 \times 10^5$ normal F344 lymph node T-lymphocytes (responders) at a ratio of 0.3:1. Eighteen hours prior to the completion of a 5-day incubation, the cells were pulsed with $^3$H-thymidine and proliferation determined by counts/minute (cpm) of thymidine incorporation in triplicate cultures. Stimulation index equals the multiples of proliferation in lymph node lymphocytes induced by varying quantity of stimulator cells relative to proliferation of lymph node lymphocytes alone. Data represent mean±SEM of three experiments.

Studies of oral tolerance have clearly demonstrated a tolerizing effect on T-lymphocytes. However, antigen presentation is an interactive process, and therefore, down-regulation of T-lymphocyte activation in tolerant hosts could be due to effects of oral tolerance on the APC as well as the T-lymphocyte. Studies were performed to determine if tolerance induction by col(V) affects APC function. WKY rats were fed col(V) (10 μg) by gastric gavage, followed by transplantation of F344 lung allografts as reported above. Two weeks after transplantation, recipient rats were euthanized, spleens harvested, individual splenocytes isolated by mechanical digestion, and the adherent fraction of splenocytes (contains APC's—stimulators) treated with mitomycin-C, and co-cultured in various ratios with $3\times10^5$ T-lymphocytes (responders) (>95% CD3+) isolated from lymph nodes of normal F344 rats. Controls for these studies were adherent splenocytes from normal WKY rats co-cultured with lymph node T-lymphocytes from normal F344 rats. After a 5-day incubation, proliferation was determined by $^3$H-thymidine incorporation as described above. FIG. 18 shows that adherent splenocytes from normal WKY rats produced dose dependent stimulation in F344 T-lymphocytes. In contrast, adherent splenocytes from col(V)-fed WKY allograft recipients did not induce proliferation in allogeneic T-lymphocytes. These data suggest that oral tolerance down regulates immune responses to antigens by affecting APC's.

The present inventor has shown that feeding a specific amount (10 μg) of col(V), but not col(II) or col(XI), over a given time period induces tolerance to donor alloantigens and prevents acute lung allograft rejection (Yasufuku et al. Submitted). However, induction of oral tolerance may be affected by the dose of antigen and duration of feeding. Also, since col(V) is not derived from MHC proteins but prevents rejection of F344 lung allografts transplanted into WKY recipients (Yasufuku et al. Submitted), col(V) may induce tolerance to allografts irrespective of the MHC alleles. Classically, oral tolerance prevents the onset of new disease (Faria and Weiner 1999; Mayer 2000; Garside and Mowat 1997). However, a very recent study in a experimental system unrelated to transplantation showing that oral tolerance can suppress immune responses after onset of disease (Baggi et al. 1999) suggests that oral tolerance may abrogate established rejection episodes. It is contemplated that oral tolerance induced by col(V), administered according to the methods of the present invention, reverses established acute rejection, and prevents development of chronic rejection (bronchiolitis obliterans).

Depending on the disease state, the induction of oral tolerance has been shown to be dependent on the presence of CD4+ and/or CD8+ T-lymphocytes in the recipient, and tolerance can be adoptively transferred to naïve animals by these cells (Faria and Weiner 1999; Mayer 2000; Garside and Mowat 1997). Activation of CD4+ and/or CD8+ T-lymphocytes depends on bi-directional interactions with APC's, namely macrophages and dendritic cells, and APC function may be up-regulated or suppressed by this interaction (Liu et al. 1999; Li et al. 1999; Lederman and Siciu-Foca 1999). However, ineffective antigen presentation by APC's from tolerant hosts could also be due to a direct effect of the tolerogen on the APC. The requirement for CD4+ and CD8+ T-lymphocytes in the induction of oral tolerance to lung allografts is unknown, and the specific role of these cells and APC's in the suppression of the immune response to lung allografts has not been evaluated.

Antigens utilized for induction of oral tolerance have been reported to contain pathogenic as well as tolerogenic peptides. In addition, the beneficial effect of tolerogenic peptides may be masked by simultaneous administration of pathogenic peptides (Faria and Weiner 1999; Mayer 2000; Garside and Mowat 1997). In addition, some peptides of the antigen are neither tolerogenic nor pathogenic. Therefore, isolation of specific tolerogenic peptides of col(V) may be more effective than intact col(V) in oral tolerance induction to prevent lung allograft rejection. Collagen molecules are composed of three alpha-helices, and col(V) is composed of one alpha-1 chain [(α1(V)] and two alpha-2 chains [α2(V)] (Smith et al. 1991, Smith et al. 1985). In human studies, the alpha-1 chain of col(V) [α1(V)] was recognized as an antigen during lung allograft rejection (Wilkes et al. Submitted). However, in a murine model developed by the present inventor that mimics the immunology and pathology of lung allograft rejection, individual alpha-chains of col(V), and intact col(V) were equally efficacious in down-regulating the immune response to lung alloantigens (Mares et al. In Press). These data suggest that there may be multiple epitopes of col(V) on different col(V) peptides that are tolerogenic.

F. Prevention of Chronic Rejection

The present inventor has shown, as discussed above, that ingestion of col(V) prevents or diminishes the onset of acute rejection in lung allograft recipients. It has been shown that the introduction of potent immunosuppressive agents has improved the early graft survival albeit not as well as the compunds and methods of the present invention. Nevertheless, repeated acute rejection results in chronic rejection, which is the leading cause of death in lung allograft recipients. The present inventor has now discovered that prolonged ingestion of col(V), either before or after transplantation, or both, diminishes or prevents the onset of chronic rejection as well.

Utilizing the same rat lung transplant model, the present inventor was the first to report of utilizing col(V) for oral tolerance induction during lung transplantation. The present inventor contemplated that feeding col(V) would also be effective for prevention of chronic rejection. In fact, the present inventor shows herein that feeding col(V) results in prolonged oral tolerance in lung allograft recipients which down regulates rejection responses and prevents the development of BO. In addition, col(V)-induced oral tolerance down regulates cellular immune responses to donor antigens by stimulating the production of TGF-β, systemically, without affecting the ability of antigen presenting cells to present alloantigen.

BO is the leading cause of death in lung allograft recipients and is believed to be the result of repeated acute rejection episodes. However, most studies of lesions similar to BO have been reported in hetertopic rodent tracheal explants, a model that is not analogous to orthotopic lung allografts. Therefore, the lack of appropriate animal model that develops BO in a lung allograft has limited investigation of the immunopathogenesis of this disorder. However, the current study confirms a report by Hirt, et al (1999), that showed the development of BO in F344 lung allografts 50-70 days after transplantation into WKY rat recipients. Accordingly, the F344- >WKY rat lung transplant model affords the opportunity to study the pathogenesis of acute rejection and BO (chronic rejection) in an animal model that is similar to human lung transplantation.

As discussed herein, col(V) is a target of the local immune response to alloantigens in mice, and during acute lung allograft rejection in rats. Furthermore, col(V) is recognized as an antigen during lung allograft rejection in humans (Wilkes and Burlingham, manuscript in preparation). Oral tolerance induced by col(V), which is a minor collagen in the lung, was effective in down regulating acute rejection episodes, i.e., two weeks post-transplantation. Data in the Examples, below, showed that the same regimen of feeding col(V) that resulted in two weeks of tolerance resulted in at least 10 weeks of immune suppression to donor alloantigens. Significantly, prior studies using donor-derived antigens for oral tolerance-induction to solid organ allografts resulted in delayed onset of acute rejection, typically extending survival of the graft up to three weeks post-transplantation. However, the current study is the first to report oral tolerance induction for the prevention of chronic rejection in general, and the lung in particular, and demonstrates the longest reported duration of oral tolerance induced in a transplant model.

Lung allograft rejection is believed to be initiated and perpetuated by antigen presenting cells presenting alloantigens either directly or indirectly to host T-lymphocytes. Accordingly, interventions that prevent antigen presentation or inhibit T-lymphocyte responses may be effective strategies to limit rejection episodes. Although most studies of oral tolerance have reported that T-lymphocytes are effected primarily by the tolerizing process, recent studies have shown that antigen presenting cells in tolerant hosts may be ineffective in antigen presentation. However, data herein show that col(V)-induced oral tolerance does not affect the ability of antigen presenting cells to present alloantigen during lung allograft rejection. In addition, the data show that col(V)-induced oral tolerance down regulates T-lymphocyte proliferation in response to donor antigens.

Oral tolerance may effect antigen-specific T-lymphocyte responses by induction of clonal anergy, clonal deletion, or active suppression. Although clonal deletion has been reported infrequently in oral tolerance, data presented herein shows that neutralizing antibodies to TGF-β recovered DTH responses to donor antigen is evidence against this as a mechanism of col(V)-induced oral tolerance.

Regulatory or suppressor T-lymphocytes are the main source of soluble mediators that suppress immune responses during oral tolerance. These cells include Th2 lymphocytes that produce IL-4 or IL-10, Th3 lymphocytes that produce TGFβ, and Tr1 lymphocytes that produce IL-10. Neither IL-4 or IL-10 were detected in tolerant rats. However, col(V) oral tolerance induced vigorous production of TGF-β during BO. Antibodies to TGF-β recovered the DTH responses to donor alloantigens in orally tolerized animals, which suggests that Th3 cell-induced active suppression may be responsible for oral tolerance in response to col(V). Further evidence that active suppression by TGF-β is crucial to col(V)-induced tolerance is data showing that adoptive transfer of T-lymphocytes from tolerant lung allograft recipients to naïve allograft recipients induces upregulated production of TGF-β, and TGF-β-dependent suppression of cellular immune responses to donor antigens (Yasufuku and Wilkes, manuscript in preparation).

BO is the leading cause of death in lung allograft recipients and is the result of repeat rejection episodes. Therefore, data showing that col(V)-induced oral tolerance prevents acute rejection and BO in rodents suggest that similar techniques may be utilized to prevent BO in human lung allograft recipients. Furthermore, col(V) is highly conserved (non-polymorphic) amongst individuals. Accordingly, data showing that col(V) is an antigen involved in the rejection response demonstrates that lung allograft rejection involves autoimmune as well as alloimmune responses.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Development of the Murine Model that Reproduces the Immunology and Histology of Lung Allograft and Rejection The inventor has previously developed a murine model that reproduces the histology and immunology of acute lung allograft rejection wherein the perivascular and peribronchiolar connective tissues are the sites of antibody deposition (Wilkes et al., 1995; Wilkes et al., 1999). These same tissues are the sites of rejection activity in human lung allograft recipients (Trulock, 1997).

For the model the inventors use the allogenic mice strains C57BL/6 ($I-a^b$, $H-2^b$) and BALB/c ($I-a^d$, $H-2^d$). Anesthetized BALB/c mice received either C57BL/6 ($1.5\times10^5$) (allogeneic) or BALB/c (autologous) BAL cells in 100 μl of PBS by nasal insufflation weekly for four weeks (Wilkes et al., 1995; Wilkes et al., 1999; Wilkes et al., 1998). Nasal insufflation of 100 μl of PBS or autologous ($1.5\times10^5$) BAL cells weekly for four weeks had no effect on histology, BAL differential cell counts, or cytokine levels in lungs of recipient mice.

In other experiments, BALB/c mice received col(II), col(XI), col(V), or purified α1(V) or α2(V) chains by intratracheal instillation weekly for four weeks followed by four weekly instillations of allogeneic (C57BL/6) BAL cells by nasal insufflation weekly for four weeks. The intratracheal instillations insured introduction of the collagens into the lower respiratory tract. Repeated instillations of collagen (50 μg) did not induce pathologic lesions or alterations in differential cell counts in recipient lungs. At the completion of the four weekly instillations of collagen, BALB/c mice received $1.5\times10^5$ C57BL/6 BAL cells in 100 μl of PBS by nasal insufflation weekly for four weeks.

In yet other experiments, BALB/c mice received four weekly instillations of allogeneic (C57BL/6) BAL cells weekly for four weeks followed by a four week recovery period. At the end of this eight week period, BALB/c mice received $1.5\times10^5$ autologous BAL cells (BALB/c) that had been pulsed with col(II), col(V), or col(XI) into the lung by nasal insufflation weekly for four weeks. Viability exceeded 90% for all donor cells.

At the end of the study period for each group, the mice were sacrificed and serum was collected from the specimens. The trachea was dissected and transected and a 18 gauge catheter was inserted into the trachea and the lungs lavaged with a total of 2.5 ml of sterile PBS. Cell free BAL supernatants were obtained by centrifugation of BAL fluids and differential cell counts were performed on cytospin preparations of BAL cells.

The lung histology was examined. The greatest deposition of donor cells occur in the mid-lung zones (peri-hilar distribution), hence, cryostat sections were obtained from the peri-hilar regions of recipient lungs, stained with hematoxylin and eosin, examined under light microscopy, and graded according to the histologic criteria established by the Lung Rejection Study Group (Yousem et al., 1996), and as previously reported (Wilkes et al., 1995; Wilkes et al., 1999; Wilkes et al., 1998). Mononuclear cell infiltrates in the peribronchiolar and perivascular tissues analogous to grade 1-2 acute rejection in the lungs of mice that received instillations of allogeneic cells alone, or col(II) or col(XI) prior to instillations of allogeneic cells. In contrast, intrapulmonary instillations of purified α1(V) or α2(V) or intact col(V) chains prior to allogeneic BAL cells only induced perivascular edema without perivascular or peribronchiolar mononuclear cell infiltrates. Thus, limited mononuclear cell infiltrates were observed in lungs of mice that received col(V) prior to allogeneic cells.

Further, TUNEL assays performed to detect apoptosis in lung tissue sections showed that apoptotic cells were not present in the lungs of mice that received instillations of col(V) prior to instillations of allogeneic cells.

Additionally, lung lymphocytes were isolated from the lung parenchyma of normal or recipient BALB/c mice (Wilkes et al., 1998) and T-lymphocytes were obtained to perform a mixed leukocyte reaction to determine the ability of mitomycin C-treated C57BL/6 splenocytes to induce proliferation in T-lymphocytes isolated from the lungs of BALB/c mice that received weekly instillations col(V) followed by instillations of C57BL/6 BAL cells or T-lymphocytes from normal BALB/c mice (Wilkes et al., 1998). T-lymphocyte proliferation was determined by the uptake of $^3$H thymidine in triplicate and this demonstrated that donor (C57BL/6) splenocytes induced dose dependent proliferation in T-lymphocytes isolated from lungs of normal BALB/c mice. In contrast, T-lymphocytes isolated from lungs of BALB/c mice pre-treated with col(V) prior to instillation of allogeneic BAL cells did not proliferate in response to donor alloantigen.

Cytokine ELISA were also performed to measure TNF-α levels in unconcentrated BAL fluid from recipient mice (Wilkes et al., 1998). Among several cytokines, the blockade of TNF-α has been shown to down-regulate lung allograft rejection (DeMeester et al., 1993). It was seen that instillations of col(V) into the lung prior to instillations of allogeneic BAL cells down regulates local production of TNF-α and induced the local production of TNF-α in only one of five recipient mice in contrast to the instillation of allogeneic BAL cells alone which induces a vigorous production of TNF-α locally in recipient lungs.

Thus, utilizing the murine model that reproduces the histology and immunology of acute lung allograft rejection, the inventors demonstrated previously that prior instillation of col(V), but not col(II) or col(XI), prevents development of rejection pathology in response to allogeneic BAL cells, down regulates proliferative responses of lung T-lymphocytes to donor alloantigens, inhibits development of apoptosis in the recipient lung, and abrogates TNF-α production locally. Furthermore, instillation of autologous BAL cells pulsed with col(V), but not col(II) or col(XI) perpetuates the rejection pathology induced by prior instillations of allogeneic BAL cells.

Humoral responses during allograft rejection are directed against donor MHC antigens. However, since col(V) may have MHC-"like" sequences, the inventors contemplate that molecular mimicry between MHC molecules and non-MHC proteins, such as col(V), play a role in the pathogenesis of lung allograft rejection.

Example 2

Intrapulmonary Col(V) Abrogates Local Alloimmune Responses a. Mice

Six to 8 week old female C57BL/6 (I-a$^b$, H-2$^d$) and BALB/c (I-a$^d$, H-2$^d$) mice were obtained from Harlan Sprague Dawley Inc. (Indianapolis, Ind.), and housed in micro isolator cages in the Laboratory Animal Resource Center at the Indiana University School of Medicine in accordance with institutional guidelines as previously reported (Wilkes et al., 1995; Wilkes et al., 1999; Wilkes et al., 1998).

b. Collection and Phenotype of Donor Mice BAL cells

Donor BAL cells were obtained by the methods described in Wilkes et al., 1995; Wilkes et al., 1999; and Wilkes et al., 1998. In brief, anesthesia was induced in C57BL/6 and BALB/c mice by an intramuscular injection of a mixture of ketamine (80-100 mg/kg), acepromazine (8-10 mg/kg), and atropine (0.5 mg/kg). After isolation of the trachea by dissection and opening the thoracic cavity by midline incision, an 18 gauge Teflon catheter was inserted into the trachea and secured by suture. The lungs were lavaged with a total of 20 ml of phosphate buffered saline (PBS) at 37° C., and cells isolated from lavaged specimens by centrifugation. BAL cells were resuspended in PBS at a concentration of 1×10$^6$/ml. Immunocytochemical examination of cytospin preparations showed that macrophages and dendritic cells comprise 96% and 2% of BAL cells, respectively (Wilkes et al., 1995; Wilkes et al., 1999; Wilkes et al., 1998).

C. Distribution of Instilled BAL Cells in Lungs of Recipient Mice

Two different methods were utilized to determine if the cells that were instilled by nasal insulation reached the alveolar space (Wilkes et al., 1995; Wilkes et al, 1999; Wilkes et al, 1998). In brief, colloidal carbon (100 μl of a 5% saline solution, Pelikan, Hanover, Germany) was instilled by nasal insulation into the lower respiratory tract of C57BL/6 mice. After a two hour incubation, the recipient mice underwent BAL and the number of carbon loaded BAL cells was detected by examination of cytospin preparations using light microscopy. These carbon loaded BAL cells (1.5×10$^5$/mouse) were then instilled into the airway of anesthetized BALB/c mice by nasal insufflation. After two hours, the recipient mice were sacrificed, the thoracic organs harvested en bloc, fixed by inflation and immersion in 6% glutaraldehyde, sectioned, stained with eosin, and examined using light microscopy for the presence of carbon-loaded BAL cells in the alveolar spaces.

Alternatively, donor DC (C57BL/6, I-a$^b$) were identified in the alveoli of BALB/c mice by immunohistochemistry. In brief, 4 hours after nasal insufflation of C57BL/6 lung cells, the recipient lungs (BALB/c) were prepared for immunohistochemistry by intratracheal instillation of OCT compound (Tissue-Tek, Elkhart, Ind.) diluted 1:1 with PBS. After freezing in liquid nitrogen, the lungs were stored at −80° C. Localization of donor cells (I-a$^{b+}$) was performed on cryostat lung sections utilizing biotinylated mouse anti-mouse I-a$^b$ antibodies (Pharmingen). Antibody detection was performed utilizing streptavidin alkaline phosphatase and ABTS substrate following the manufacturer's directions (Kirkegaard and Perry). These studies also confirmed that donor cells (C57BL/6) reached the alveoli of recipient mice (BALB/c).

d. Preparation of Collagens

Collagen type II [col(II)] was isolated from canine cartilage as previously reported (Smith et al., 1985), or purchased from Collaborative Biomedical Products, Bedford, Mass. Both preparations were solubilized in 0.5M acetic acid, then dialyzed to yield a final concentration of 0.5 mg/ml in PBS. Bovine collagen type XI [col(XI)] from fetal calf cartilage (Morris and Bachinger, 1987) was obtained from Nicolas P. Morris, Ph.D. (Shriners Hospital for Crippled Children, Portland, Oreg.) or was purchased from Biogenesis, Sandown, N.H. Both col (XI) preparations were solubilized in 50 mM TRIS, 0.2M NaCl, pH 7.5.

Human type V collagen, [col(V)], was extracted from human placenta and purified by differential NaCl precipitation (Seyer and Kang, 1989). In brief, placental tissues were minced, washed, and suspended in 0.5 M acetic acid containing 0.2 M NaCl, and digested by pepsin at 4° C. Supernatants were aspirated from centrifuged specimens, the pellet collected and the extraction procedure repeated. The supernatants were combined from the two digests, and col(V) was purified from the supernatants by differential NaCl precipitation from 0.5 M acetic acid (Smith et al., 1985; Seyer and Kang, 1989). The type V collagen was soluble in 0.7 M NaCl and precipitated in 1.2 M NaCl. In separate experiments requiring purified $\alpha$(V) chains, the cycle of solubilization in acetic acid and NaCl precipitation was repeated until a type V preparation with an $\alpha$-chain ratio $\alpha 1(V)/\alpha 2(V)$ of approximately 2 was obtained as determined by SDS-polyacrylamide gel electrophoresis (Smith et al., 1985). Separation of $\alpha 1(V)$ from $\alpha 2(V)$ was achieved by chromatography on DEAE-cellulose (Seyer and Kang, 1989). The $\alpha 1(V)$ and $\alpha 2(V)$ chains were eluted from the column, and purity confirmed by SDS-polyacrylamide gel electrophoresis as previously reported (Smith, Jr. et al, 1985). Intact col(V), or $\alpha 1(V)$ and $\alpha 2(V)$ chains were diluted in PBS (0.5 mg/ml) until use. Col(V) was also purchased from Collaborative Biomedical Products.

The quantity of collagen types II, XI, V, $\alpha 1(V)$ and $\alpha 2(V)$ were assessed by determination of the hydroxyproline content in the samples as previously reported (Woessner, 1961; Chiang et al, 1980). Experimental outcomes were not affected by the source of col(II), col(XI), or col(V).

e. Murine Treatment Groups

Anesthetized BALB/c mice received either $1.5 \times 10^5$ C57BL/6 (allogeneic) or BALB/c (autologous) BAL cells in 100 µl of PBS by nasal insufflation weekly for four weeks (Wilkes et al., 1995; Wilkes et al., 1999; Wilkes et al., 1998). The experiments performed demonstrated that nasal insufflation of 100 µl of PBS or autologous $(1.5 \times 10^5)$ BAL cells weekly for four weeks had no effect on histology, BAL differential cell counts, or cytokine levels in lungs of recipient mice.

In other experiments, BALB/c mice received col(II), col(XI), col(V), or purified $\alpha 1(V)$ or $\alpha 2(V)$ chains by intratracheal instillation weekly for four weeks followed by four weekly instillations of allogeneic (C57BL/6) BAL cells by nasal insufflation weekly for four weeks. In brief, BALB/c mice were anesthetized, the ventral surface of the neck shaved, the trachea isolated by blunt dissection, and cannulated with a 22 g Teflon catheter. Each mouse received 50 µg of col(II), col(V), or purified $\alpha 1(V)$ or $\alpha 2(V)$ chains in 100 µl of PBS; or 50 µg of col(XI) in 100 µl of diluent (0.01M acetic acid, 0.2M NaCl, pH 7.5) intratracheally, weekly for four weeks. Intratracheal instillations were performed to insure introduction of the collagens into the lower respiratory tract. Preliminary studies confirmed that repeated instillations of collagen (50 µg) did not induce pathologic lesions or alterations in differential cells counts in recipient lungs. At the completion of the four weekly instillations of collagen, BALB/c mice received $1.5 \times 10^5$ C57BL/6 BAL cells in 100 µl of PBS by nasal insufflation weekly for four weeks.

In separate experiments, BALB/c mice received four weekly instillations of allogeneic (C57BL/6) BAL cells weekly for four weeks followed by a four week recovery period. At the end of this eight week period, BALB/c mice received $1.5 \times 10^5$ autologous BAL cells (BALB/c) that had been pulsed with col(II), col(V), or col(XI) into the lung by nasal insufflation weekly for four weeks. In brief, BALB/c BAL cells ($1.5 \times 10^5$ /ml) were incubated with collagen types II, V, or XI (100 µg/ml) in complete media [RPMI 1640 supplemented with 10% heat inactivated fetal calf serum in RPMI 1640 with 25 mM Hepes, 2 mM glutamine, 100 U/ml penicillin, 100 mg/ml streptomycin (all from Gibco, Grand Island, N.Y.)] for 24 h at 37° C., 5%. After washing, cells were resuspended in PBS, and $1.5 \times 10^5$ cells instilled into the lung by nasal insufflation. Viability exceeded 90% for all donor cells.

f. Collection of Serum and BAL at Completion of Experimental Period

At the end of the study period for each group, mice were anesthetized with ketamine, acepromazine, atropine. The thoracic and abdominal cavities were opened and mice exsanguinated by cardiac and inferior vena cava puncture. Serum was collected from centrifuged specimens. After the trachea was dissected and transected, a 18 gauge catheter was inserted into the trachea and the lungs lavaged with a total of 2.5 ml of sterile PBS. In brief, a 0.5 to 1.0 ml aliquot of PBS was instilled into the trachea and aspirated five times before placement into a specimen container. Cell free BAL supernatants were obtained by centrifugation of BAL fluids. All serum and BAL supernatants were stored at –80° C. until use. Differential cell counts were performed on cytospin preparations of BAL cells.

g. Lung Histology

The thoracic organs of recipient mice were removed en bloc after BAL and were fixed by an intratracheal instillation of 6% glutaraldehyde. Preliminary studies demonstrated that the greatest deposition of donor cells occurred in the midlung zones (peri-hilar distribution). Therefore, four to six cryostat sections were obtained from the peri-hilar regions of recipient lungs, stained with hematoxylin and eosin, examined under light microscopy, and graded according to the histologic criteria established by the Lung Rejection Study Group (Yousem et al., 1996), and as previously reported (Wilkes et al., 1995; Wilkes et al., 1999; Wilkes et al., 1998). In addition, all grading of histologic sections were done in blinded fashion without prior knowledge of the treatment group (Wilkes et al., 1995; Wilkes et al., 1999; Wilkes et al., 1998).

h. Detection of Apoptosis

TdT-mediated dUTP Nick End Labeling (TUNEL) assay kits (In Situ Cell Death Detection Kit, Boehringer Mannheim, Indianapolis, Ind.) were utilized to detect apoptosis in lung tissue sections. In brief, xylene was utilized to remove wax from paraffin embedded tissues, and serial incubations with decreasing ethanol solutions were utilized to rehydrate tissue sections. After placement in Sequenza chambers (Shandon Lipshaw, Pittsburgh, Pa.), and immersion in Tris buffered saline (TBS–0.05M Tris/HCl pH 7.5-8.0 in 0.15M saline), slides were treated with Proteinase K solution (20 μg/ml in 10 mM Tris/HCl, pH 7.4-8.0) for 30 minutes at 37° C. Tissues sections treated with deoxyribonuclease I (1 mg/ml) (Boehringer) for 30 minutes at room temperature were utilized for positive controls for the TUNEL assay. The labeling and alkaline phosphatase conversion steps were performed per protocol supplied by the manufacturer. Substrate solution (BrdU Labeling and Detection Kit, Boehringer) was utilized to develop reaction products per manufacturer's directions. Slides were coverslipped and examined by light microscopy.

i. Isolation of Lung Lymphocytes

Since very few BAL T-lymphocytes were available for these studies, lymphocytes were isolated from the lung parenchyma of normal or recipient BALB/c mice (Wilkes et al., 1998). In brief, mice were injected with 150 μl of heparin (1000 U/ml) (Upjohn, Kalamazoo, Mich.), and anesthetized using intramuscular injection of a mixture of ketamine (80-100 mg/kg), acepromazine (8-10 mg/kg), and atropine (0.5 mg/kg). After opening the chest and abdominal cavity by midline incision, and exsanguination by transection of the inferior vena cava, the trachea was isolated and BAL performed utilizing five 1 ml aliquots of sterile PBS (37° C.). Once the pulmonary vasculature was perfused with 10 ml of PBS (37° C.) to remove peripheral blood, lungs were removed avoiding all lymph node tissue, placed in a petri dish, and minced into 1 mm cubes. The lung tissue was further digested by stirring in a flask containing collagenase/DNAase solution for 90 min at 37° C. Collagenase/DNAase solution: 52.5 mg collagenase (Boehringer Mannheim) was added to media: 10 ml RPMI (Gibco Laboratories, Long Island, N.Y.) and 10% heat inactivated fetal calf serum (Hyclone, Logan, Utah). 1 ml of DNAase (Boehringer Mannheim) stock solution (3 mg/ml) was added to each 5 ml of collagenase solution. To remove particulate matter from the collagenase preparation and to obtain individual lung T-lymphocytes, the cells were centrifuged over a Percoll (Pharmacia, Piscataway, N.J.) gradient, incubated on a nylon wool column for 1 h at 37° C. and eluted from the column utilizing complete media. Any remaining red blood cells were removed by lysis utilizing ammonium chloride. Immunocytochemical analysis of cytospin preparations confirmed that the cells obtained were T-lymphocytes (>90% Thy-1+).

j. Mixed Leukocyte Reaction

The ability of mitomycin C-treated C57BL/6 splenocytes to induce proliferation in T-lymphocytes isolated from the lungs of BALB/c mice that received weekly installations col(V) followed by instillations of C57BL/6 BAL cells or T-lymphocytes from normal BALB/c mice was determined by a mixed leukocyte reaction (MLR) (Wilkes et al., 1998). In brief, C57BL/6 splenocytes, which were utilized as source of antigen presenting cells (APC's ), were treated with mitomycin-C (Sigma) and co-cultured in varying ratios with lung T-lymphocytes ($3 \times 10^5$/well) in 200 μl of media [RPMI, 2 mM L-glutamine, $5 \times 10^{-5}$ M 2-mercaptoethanol, 100 U/ml penicillin, 100 μl/ml streptomycin, 10% heat inactivated fetal calf serum] in flat bottom 96 well microtiter plates (Costar, Cambridge, Mass.). Eighteen hours prior to the completion of a 3 day incubation at 37° C. (5% $CO_2$), 0.5 μCi/ml of $^3H$ (Amersham Corp, Arlington Heights, Ill.) was added to each well. Cultures were harvested with an automated cell harvester (Brandel, Gaithersburg, Md.) and analyzed in a liquid scintillation counter (Beckman, Arlington Height, Ill.). Cellular proliferation was determined as the mean of counts per minute of $^3H$ thymidine incorporation in triplicate cultures and reported as a Stimulation Index as described below in the section named Results.

k. Cytokines ELISA

TNF-α was measured in unconcentrated BAL fluid from recipient mice utilizing commercial ELISA kits (R&D Systems, Minneapolis, Minn.) per manufacturer's protocol. The sensitivity of this assay was 23.4 pg/ml. IL-4 and IL-10 were measured by ELISA in unconcentrated BAL fluid of recipient mice as previously reported (Wilkes et al., 1998).

l. Statistics

The data were initially assessed to confirm normality using a Shapiro-Wilk statistic. Comparisons between groups were analyzed for each of the dependent variables using a one-way analysis of variance (ANOVA) with four interventions. For those comparisons demonstrating significance, a post-hoc Student-Newman-Keuls was performed to determine differences between interventions. Where multiple comparisons were performed, a Bonferonni correction was applied and the significance level was 0.02. For other comparisons, the level of significance was 0.05.

Differences in TNF-α levels between groups was determined utilizing Mann-Whitney "U" test for unpaired data. p values<0.05 were considered to be significant.

Data regarding the presence or absence of pathologic lesions in the lungs of mice that received allogeneic cells alone or collagen-pulsed autologous BAL cells was determined by utilizing a log-likelihood G-statistic. p values<0.05 were considered significant.

m. Results

Figure 1A:
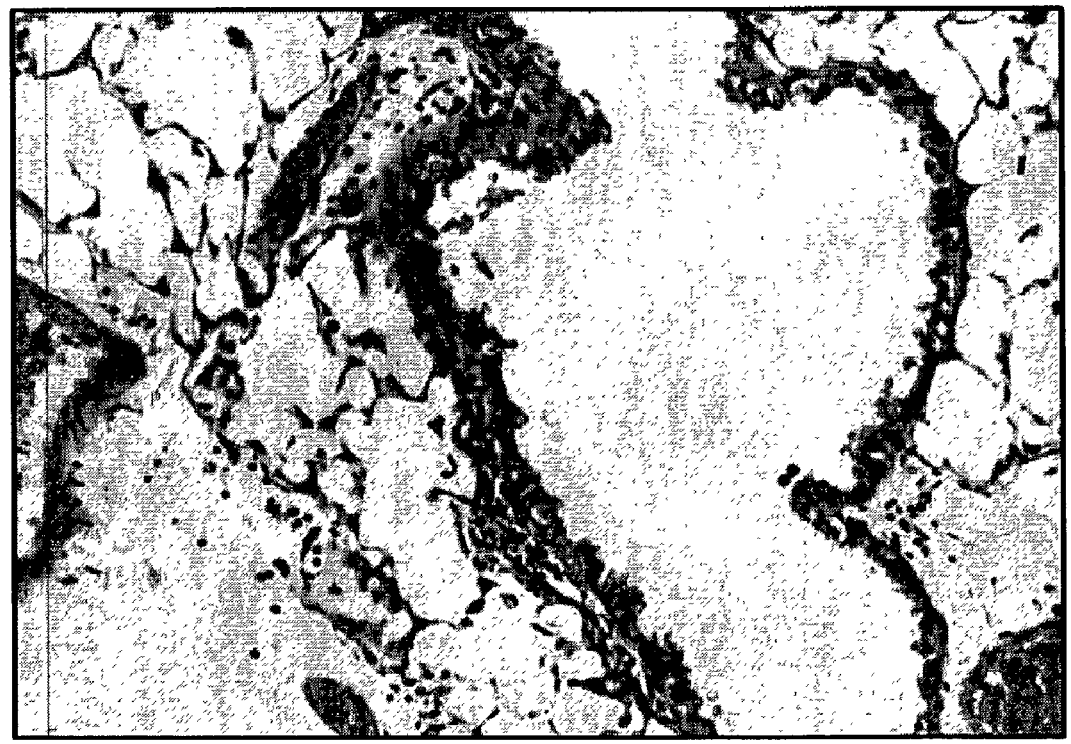
Figure 2A:
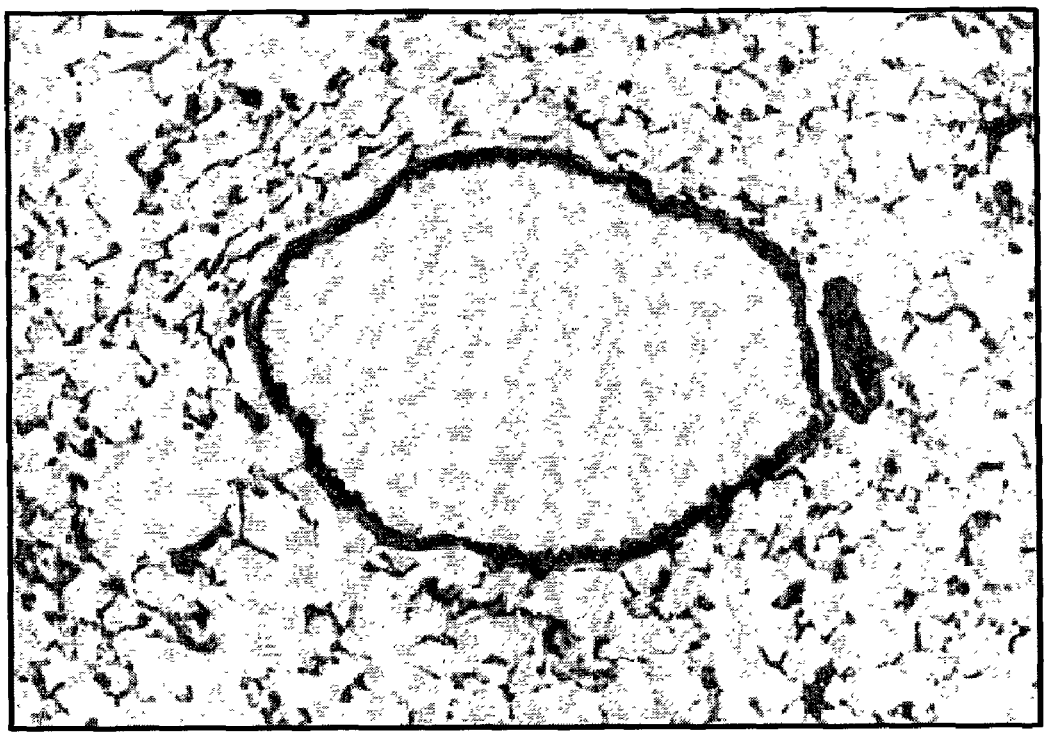
FIG. 2A and FIG. 2B. Lung histology in BALB/c mice after four weekly instillations of purified α1(V) chains or α2(V) chains (50 µg each) followed by four weekly instillations of $1.5 \times 10^5$ allogeneic (C57BL/6) BAL cells alone.
Figure 1C:
Figure 2B:
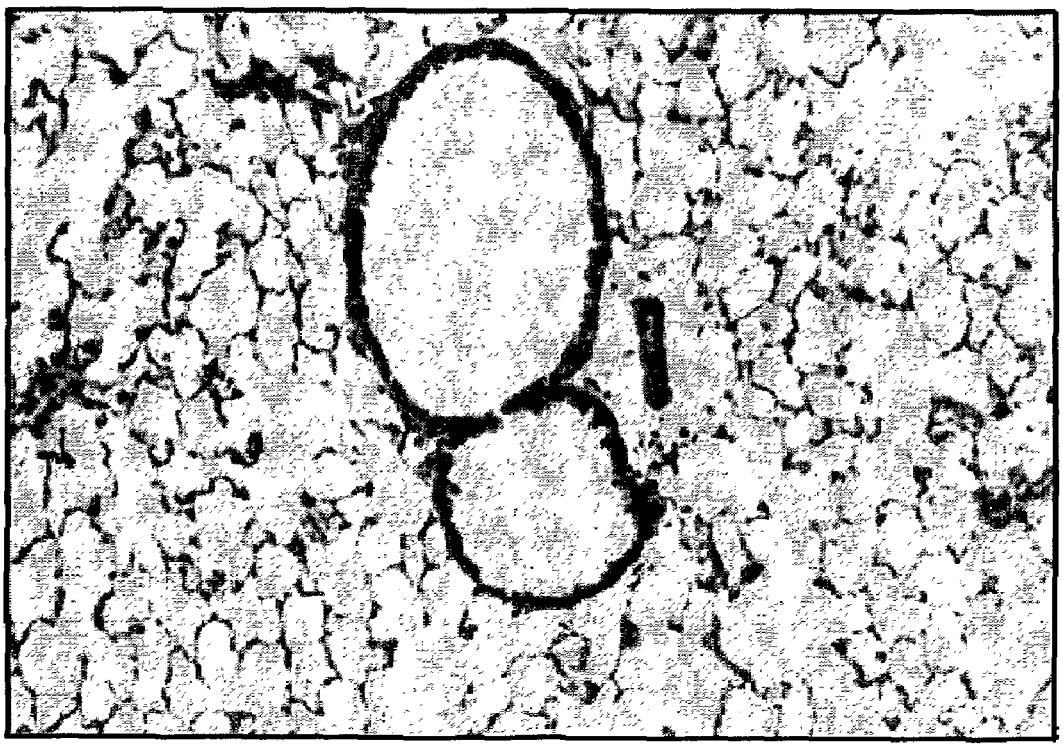
Figure 3:
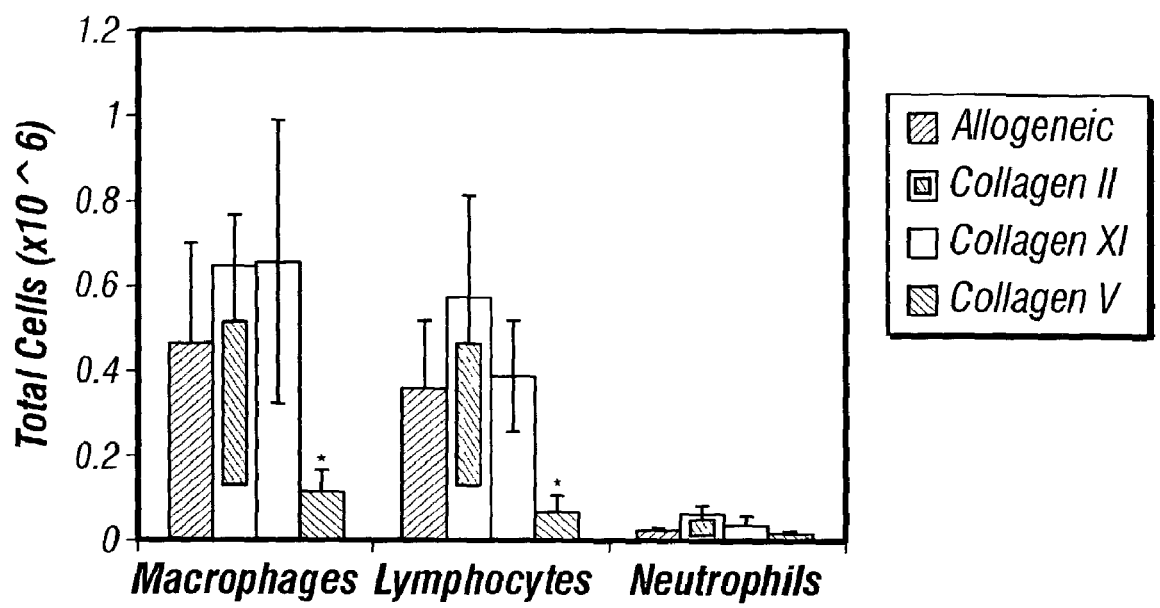
FIG. 3. Differential cell counts in bronchoalveolar lavage fluid of recipient mice. BALB/c mice received $1.5 \times 10^5$ allogeneic (C57BL/6) BAL cells alone, or col(II), col(XI), or col(V) (50 µg each) weekly for four weeks followed by four weekly instillations of C57BL/6 BAL cells. At the completion of the experimental period recipient mice under BAL and differential cell counts were performed by counting 300 cells per high powered field on cytospin preparations. Data represent the mean±S.D. of four to six recipient mice in each group (*p<0.002 for macrophages, and<0.0005 for lymphocytes).

Initial experiments determined if intrapulmonary instillation of col(V) prior to instillation of allogeneic cells would prevent the development of histology analogous to the rejection response in recipient lungs. BALB/c mice received 100 μl of PBS, 50 μg purified α1(V) chains or α2(V) chains, or intact col(II), col(V), or col(XI) in 100 μl of diluent (as described above) by intratracheal instillation weekly for four weeks. This was followed by four weekly instillations of $1.5 \times 10^5$ C57BL/6 BAL cells in 100 μl of PBS into the lungs by nasal insufflation. Col(II), a major component of articular cartilage (Smith, Jr. et al., 1985), is not present in the lung and, therefore, served as a control for these studies. Col(XI), a minor component within cartilage (Morris and Bachinger, 1987), has not been demonstrated within lung parenchyma. At the completion of the experimental period, BAL was performed, and lungs of recipient mice were harvested, fixed, and examined for rejection pathology. FIG. 1 shows mononuclear cell infiltrates in the peribronchiolar and perivascular tissues analogous to grade 1-2 acute rejection in the lungs of mice that received instillations of allogeneic cells alone (FIG. 1A), or col(II) or col(XI) prior to instillations of allogeneic cells (FIGS. 1B, and 1C, respectively). In contrast, FIG. 2 shows that intrapulmonary instillations of purified α1(V) or α2(V) chains prior to allogeneic BAL cells only induced perivascular edema without perivascular or peribronchiolar mononuclear cell infiltrates (FIGS. 2A, and 2B, respectively). Similar data was observed in experiments utilizing intact col(V). Preliminary experiments showed that four weekly instillations of collagens, diluent for collagens, or PBS alone did not induce any alterations in the histology or differential cell counts in recipient lungs. Consistent with limited mononuclear cell infiltrates in lungs of mice that received col(V) prior to allogeneic cells, FIG. 3 shows significantly fewer macrophages and lymphocytes in BAL fluid of these same mice compared to mice that received allogeneic cells alone, or col(II) or col(XI) prior to allogeneic cells (*p<0.002 and<0.0005, for macrophages and lymphocytes, respectively). Instillation of purified α1(V) or α2(V) chains prior to allogeneic cells resulted in differential cell counts similar to that observed utilizing intact col(V).

BAL differential cell counts for macrophages and lymphocytes were comparable in mice that received allogeneic cells alone, or col(II) or col(XI) prior to allogeneic cells (FIG. 3).

Figure 4:
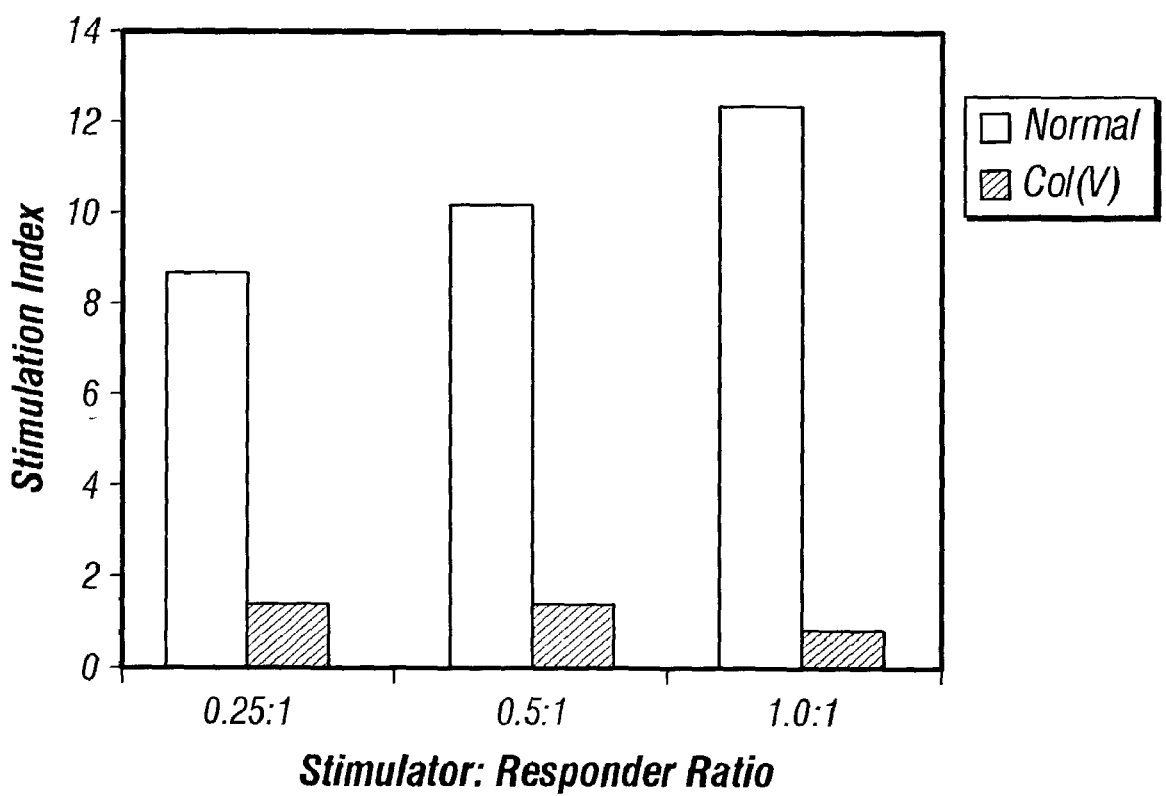
FIG. 4. Mixed leukocyte reaction. Variable quantities of mitomycin-C-treated C57BL/6 splenocytes (stimulators) were incubated with $3 \times 10^5$ T-lymphocytes (responders) isolated from lungs of normal BALB/c mice (Normal), or BALB/c mice that received four weekly instillations of type V collagen- "col(V)" (50 μg) followed by four weekly instillations of C57BL/6 BAL cells. Eighteen hours prior to the completion of a 72 h incubation, the cells were pulsed with $^3$H and proliferation determined by counts/minute (cpm) of thymidine incorporation. Stimulation index equals the multiples of proliferation in lung lymphocytes induced by varying quantity of stimulator cells relative to proliferation of lung lymphocytes alone. Data representative of three experiments.
Figure 7A:
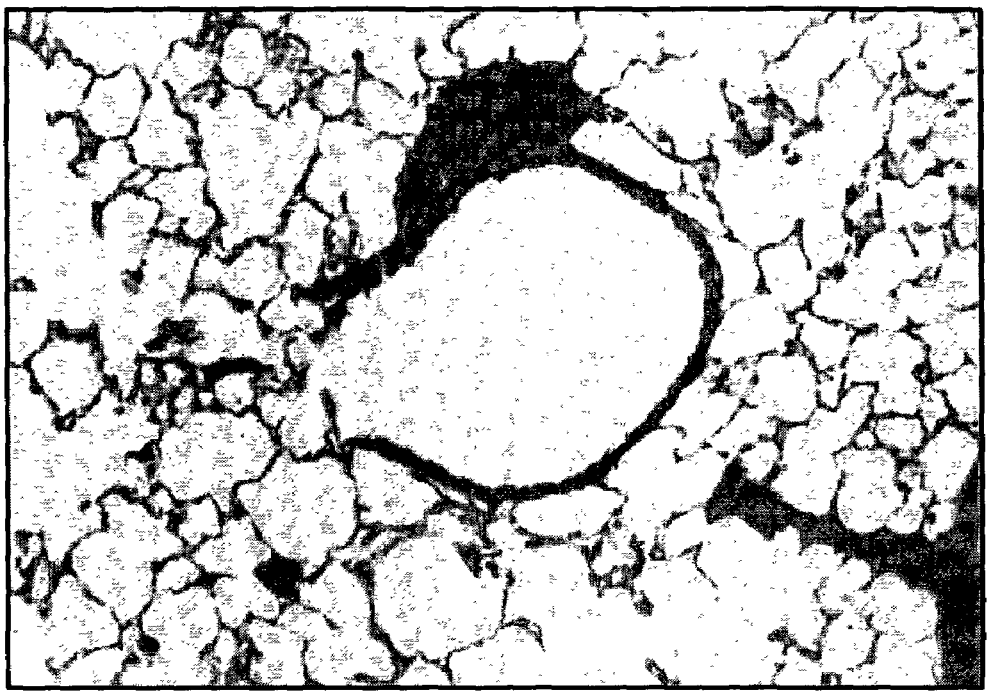
FIG. 7A, FIG. 7B, FIG. 7C, and FIG. 7D. Effect of instillation of collagen-pulsed autologous BAL cells into lungs of mice primed with allogeneic BAL cells. BALB/c mice received four weekly instillations of $1.5 \times 10^5$ allogeneic (C57BL/6) BAL cells into the lung weekly for four weeks followed by a four week recovery period. At the completion of this eight week period, mice received no further instillations, or instillations of $1.5 \times 10^5$ autologous (BALB/c) BAL cells that had been pulsed with either col(II), col(XI), or col(V) into the lung weekly for four weeks. Histology is shown for the different treatment groups at the completion of the 12 week experimental period.

Prior reports have shown that prevention of allograft rejection by pre-transplant immunization with peptides that may be similar to donor MHC molecules is in part due to impaired proliferative responses of host T-lymphocytes to donor alloantigens (Krensky and Clayberger, 1997; Oluwole et al., 1993). Therefore, the present inventors next determined if instillation of col(V) into the lung prior to instillation of allogeneic BAL cells prevented T-lymphocyte proliferation in response to donor alloantigen. Since instillation of α1(V), α2(V), or intact col(V) prior to instillations of allogeneic cells all induced comparable pathology and BAL differential cell counts in the lung, all subsequent studies involving col(V) utilized intact col(V) proteins and not individual α-chains. BALB/c mice received intrapulmonary instillations of col(V) (50 μg) for four weeks followed by four weekly instillations of C57BL/6 BAL cells. At the completion of the study period, the ability of C57BL/6 splenocytes to induce proliferation in lung T-lymphocytes isolated from recipient or normal BALB/c mice was determined by $^3$H thymidine incorporation. FIG. 4 shows that donor (C57BL/6) splenocytes induced dose dependent proliferation in T-lymphocytes isolated from lungs of normal BALB/c mice. In contrast, T-lymphocytes isolated from lungs of BALB/c mice pre-treated with col(V) prior to instillation of allogeneic BAL cells did not proliferate in response to donor alloantigen, and at stimulator:responder ratios of 1:1 proliferation was inhibited (FIG. 4).

Upregulated TNF-α production has been shown to have a key role in the pathogenesis of lung allograft rejection in vivo and alloimmune responses in vitro (Danzer et al., 1994; DeMeester et al., 1993). Therefore, the present inventors further determined if instillations of col(V) into the lung prior to instillations of allogeneic BAL cells down regulates local production of TNF-α. Table 1 shows that instillation of allogeneic BAL cells induces the vigorous production of TNF-α locally in recipient lungs. In contrast to instillations of allogeneic BAL cells alone, instillations of col(V) prior to allogeneic BAL cells induced the local production of TNF-α in only one of five recipient mice (*p<0.016). TNF-α was not detected in BAL fluid of normal mice or mice that received instillates of autologous cells.

TABLE 1

TNF-α Levels (pg/ml) in Bronchoalveolar Lavage Fluid

| Mouse | Allogeneic Instillate | *Col(V) + Allogeneic Instillate |
|---|---|---|
| 1 | 39.26 | 0 |
| 2 | 107.81 | 0 |
| 3 | 34.03 | 24.24 |
| 4 | 38.6 | 0 |
| 5 | 24.23 | 0 |

TNF-α levels in bronchoalveolar lavage (BAL) fluid of BALB/c mice that received four weekly instillations of 1.5 × 10$^5$ BAL cells from C57BL/6 mice (allogeneic instillate) or four weekly instillations of col(V) followed by four weekly instillations of 1.5 × 10$^5$ BAL cells from C57BL/6 mice. At the end of the experimental period recipient BALB/c mice underwent BAL and TNF-α levels were determined by ELISA (*p < 0.016 allogeneic instillate compared to col(V) + allogeneic instillate).

Figure 5:
FIG. 5. Instillation of allogeneic BAL cells induces apoptosis in recipient lungs. BALB/c mice received instillations of $1.5 \times 10^5$ allogeneic (C57BL/6) BAL cells into the lung weekly four weeks. At the completion of the experimental period, TUNEL assays were utilized to detect apoptotic cells in lung tissue sections. Apoptotic cells indicated by dark blue nuclei (see arrows) are present in airway epithelium and vascular endothelium. Tissue section representative of 10 recipient mice in this group (200× magnification).
Figure 6:
FIG. 6. Detection of apoptotic cells in lungs of mice that received col(V) prior to allogeneic BAL cells. BALB/c mice received 50 μg of col(V) into the lung weekly for four weeks followed by four weekly instillations of $1.5 \times 10^5$ allogeneic (C57BL/6) BAL cells. At the completion of the experimental period, TUNEL assays were utilized to detect apoptotic cells in lung tissue sections. In contrast to FIG. 5, in FIG. 6 no apoptotic cells were detectable in lungs of mice that received instillations of col(V) prior to instillations of allogeneic BAL cells. Tissue sections representative of 8 recipient mice (200× magnification).

Utilizing TUNEL assays which detect DNA strand scission, a commonly utilized method to identify apoptotic cells, the present inventors determined if apoptosis contributed to the airway pathology and vasculopathy induced by the instillation of allogeneic BAL cells into recipient lungs. FIG. 5 shows that instillation of C57BL/6 BAL cells into the lungs of BALB/c mice weekly for four weeks induced apoptosis in airway epithelium and vascular endothelium in recipient BALB/c mouse lungs. There were no apoptotic cells present in lungs of normal mice. To determine if col(V) down regulated rejection pathology by preventing apoptosis in response to allogeneic BAL cells, BALB/c mice received four weekly instillations of col(V) (50 μg) into the lung followed by four weekly instillations of C57BL/6 BAL cells. At the completion of the experimental period apoptosis was detected in tissue sections of recipient lungs by TUNEL assay. In contrast to mice that received allogeneic BAL cells, FIG. 6 shows that apoptotic cells were not detected in the lungs of mice that received instillations of col(V) prior to instillations of allogeneic cells.

Figure 7C:
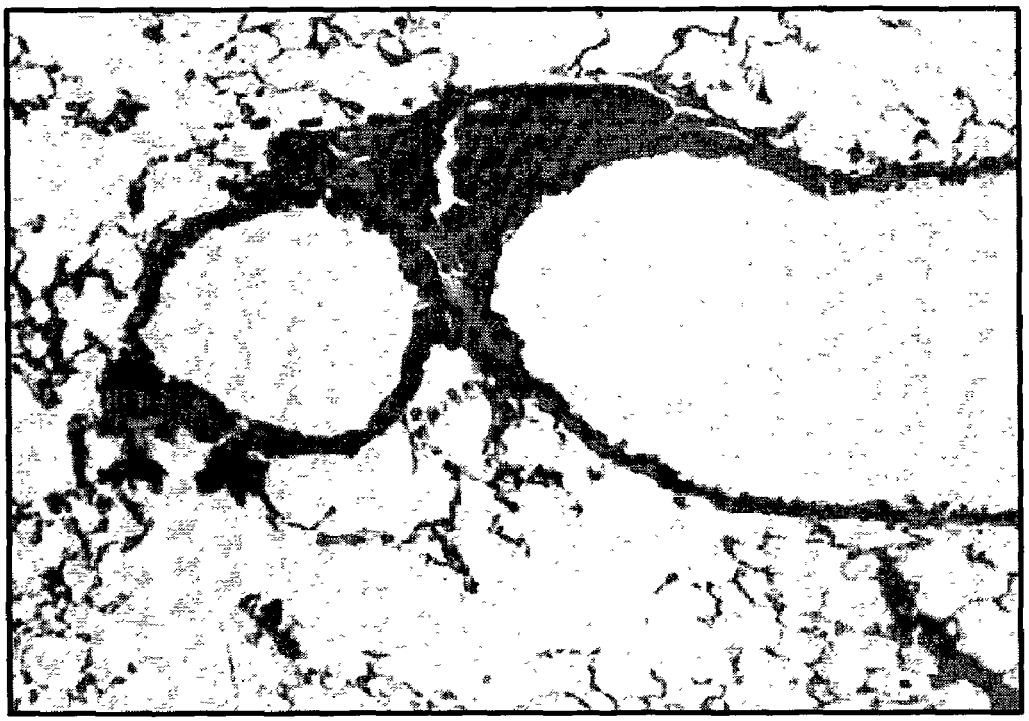
Figure 7B:
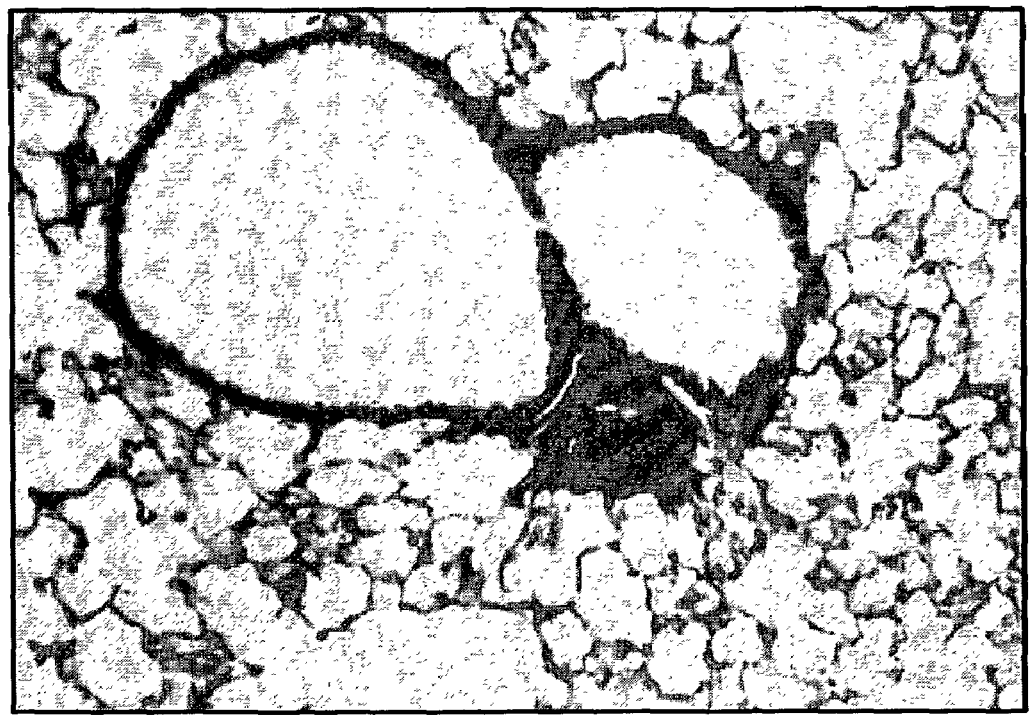
Figure 7D:
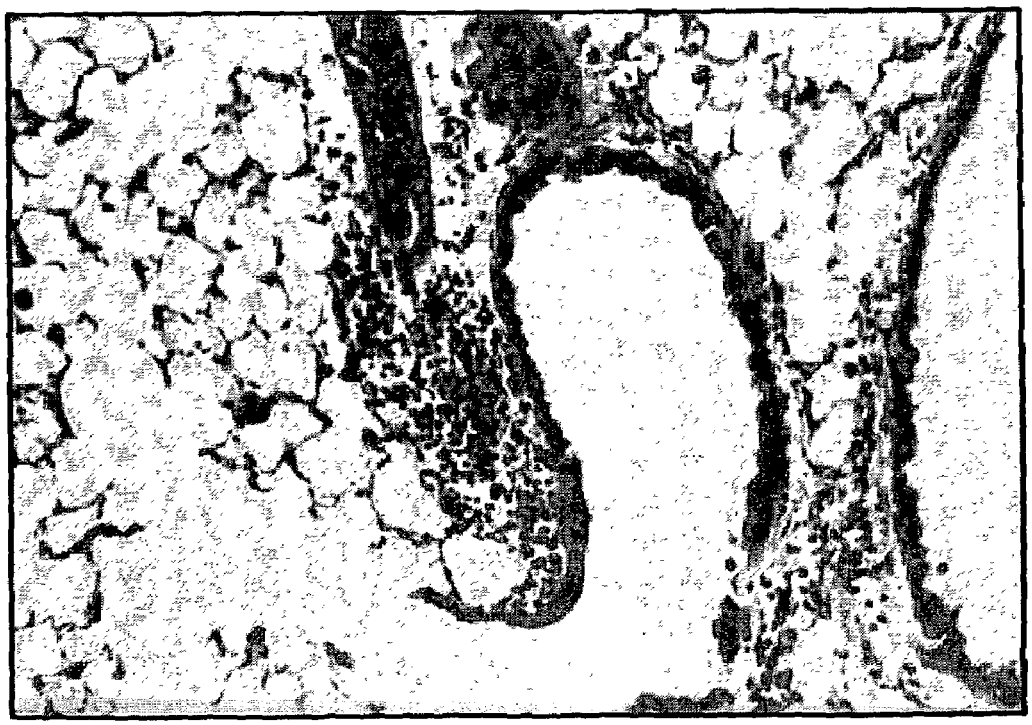

The inventors also determined if repeated instillations of col(II), col(XI), or col(V) in the lung would perpetuate the perivascular and peribronchiolar mononuclear cell infiltrates induced initially by instillations of allogeneic BAL cells. The inventors found that the vasculopathy and bronchitis induced by allogeneic BAL cells resolves completely within five weeks after the last instillation of cells. Therefore, BALB/c mice received instillations of 1.5×10$^5$ C57BL/6 BAL cells into the lung weekly for four weeks followed by a four week recovery period. At the completion of this eight week period, recipient mice did not receive any further interventions, or received four weekly intrapulmonary instillations of autologous BAL cells (BALB/c, 1.5×10$^5$) that had been pulsed with 100 μg of either col(II), col(XI), or col(V) as described above. At the completion of this 12 week experimental period, the lungs were harvested and examined for the development of rejection pathology and the results are shown in FIGS. 7A-D. Normal histology was seen in the lungs of mice that received allogeneic cells only in the initial four week period (FIG. 7A), and lungs of mice that received allogeneic cells followed by autologous BAL cells pulsed with col(II) (FIG. 7B), or col (XI) (FIG. 7C). In contrast, FIG. 7D shows that instillation of allogeneic BAL cells followed by autologous BAL cells pulsed with col(V) induced perivascular and peribronchiolar infiltrates analogous to grade 1-2 acute rejection in recipient lungs. Table 2 shows that three of 5 mice that received col(V)-pulsed autologous BAL cells developed pathologic lesions in the lung compared to absence of lesions in the lungs of mice that received col(II) or col(XI)-pulsed autologous cells (*p<0.048).

TABLE 2

Presence of Pathology Characteristic of Rejection in Lungs of Recipient Mice 12 Weeks After Instillation of Allogeneic BAL Cells Alone or Allogenic Cells Followed by Collagen-pushed Autologous BAL Cells.

| Mouse | Allo Instillate Alone | Allo Instillate + col(II)-Pulsed Autologous BAL Cells | Allo Instillate + col(XI)-Pulsed Autologous BAL Cells | *Allo Instillate + col(V)-Pulsed Autologous BAL Cells |
|---|---|---|---|---|
| 1 | Normal histology | Normal histology | Normal histology | Grade 1-2 rejection |
| 2 | Normal histology | Normal histology | Normal histology | Mild Inflammation |
| 3 | Normal histology | Normal histology | Normal histology | Grade 1 rejection |
| 4 | Normal histology | Normal histology | Normal histology | Grade 1 rejection |

TABLE 2-continued

Presence of Pathology Characteristic of Rejection
in Lungs of Recipient Mice 12 Weeks After Instillation
of Allogeneic BAL Cells Alone or Allogenic Cells
Followed by Collagen-pushed Autologous BAL Cells.

| Mouse | Allo Instillate Alone | Allo Instillate + col(II)-Pulsed Autologous BAL Cells | Allo Instillate + col(XI)-Pulsed Autologous BAL Cells | *Allo Instillate + col(V)-Pulsed Autologous BAL Cells |
|---|---|---|---|---|
| 5 | Normal histology | Normal histology | Normal histology | Mild Inflammation |

BALB/c mice received 1.5 × 10$^5$ BAL cells from C57BL/6 mice into the lung weekly for four weeks, alone (Allo Instillate, alone), or followed by a four week rest period with subsequent instillations of autologous BAL cells pulsed with either col(II), col(XI), or col (V) into the lung weekly for four weeks. At the completion of the 12 week experimental period the lungs were harvested from recipient mice in each group andgraded according to the presence of pathology characteristic of rejection (*p < 0.048 compared to all other groups).

Thus, utilizing the murine model that reproduces the histology and immunology of acute lung allograft rejection, data the inventors demonstrated previously that prior instillation of col(V), but not col(II) or col(XI), prevents development of rejection pathology in response to allogeneic BAL cells, down regulates proliferative responses of lung T-lymphocytes to donor alloantigens, inhibits development of apoptosis in the recipient lung, and abrogates TNF-α production locally. Furthermore, instillation of autologous BAL cells pulsed with col(V), but not col(II) or col(XI) perpetuates the rejection pathology induced by prior instillations of allogeneic BAL cells.

Col(V) is a minor collagen in the lung and is located the perivascular and peribronchiolar connective tissues (Madri and Furthmayr, 1980; Madri and Furthmayr, 1979; Konomi et al., 1984), which are the same sites of rejection activity. The inventors prior studies have shown the selective deposition of IgG2a antibodies in these same tissues of mice that have received weekly instillations of allogeneic BAL cells (Wilkes et al., 1995; Wilkes et al., 1999). Humoral responses during allograft rejection are directed against donor MHC antigens. However, since col(V) may be MHC-"like", the data described above indicates that molecular mimicry (Krensky and Clayberger, 1997) between MHC molecules and non-MHC proteins, such as col(V), may be active in the pathogenesis of lung allograft rejection.

Several cytokines have been implicated in the pathogenesis of lung allograft rejection (Trulock, 1997). Of these, only blockade of TNF-α has been shown to down-regulate lung allograft rejection (DeMeester et al., 1993). The mechanism of TNF-α induced allograft destruction likely includes enhanced alloimmune responses (Trulock, 1997; DeMeester et al., 1993), and induction of apoptosis in the allograft (Murphy et al., 1999). As the instillation of allogeneic BAL cells induced the vigorous production of TNF-α and apoptosis in recipient lungs showing that instillation of col(V) prevented pathologic lesions and apoptosis in recipient lungs may be due to col(V) induced down-regulation of local TNF-α production. The specific mechanism of TNF-α in stimulating lung allograft rejection remains to be determined.

In contrast, the IL-4 and/or IL-10 levels have been associated with induction of tolerance to antigens (Strober and Coffman, 1997). However, neither IL-4 nor IL-10 was detected by ELISA in BAL fluid from lungs of mice that received instillations of col(V) prior to instillations of allogeneic BAL cells.

The data showing that rejection pathology is perpetuated by instilling col(V)-pulsed autologous APC's into the lungs of mice primed previously with instillations of allogeneic BAL cells indicates that indirect allorecognition has role in the pathogenesis of lung allograft rejection. These data are similar to a very recent report by SivaSai et al., 1999, who showed that peripheral blood mononuclear cells from lung allograft recipients undergoing chronic rejection proliferated in response to donor-derived MHC class I peptides presented by host antigen presenting cells.

Example 3

Induction of Oral Tolerance a. Animals

Pathogen-free, MHC (RT1)-incompatible male rats utilized were: Fischer 344 (F344, RT1$^{1v1}$), Brown Norway (BN, RT1$^n$), and Wistar Kyoto (WKY, RT1$^1$) rats (250-300 g at the time of transplantation), purchased from Harlan Sprague Dawley (Indianapolis, Ind.) or Taconic (Germantown, N.Y.) and housed in the Laboratory Animal Resource Center at Indiana University School of Medicine (Indianapolis, Ind.) in accordance with institutional guidelines.

b. Preparation of Type V Collagen

Purified human type V collagen [col(V)] was diluted in 0.005M acetic acid (0.5 mg/ml) and stored at 4° C. until use. The quantity of col(V) was assessed by determination of the hydroxyproline content in the samples (Woessner, 1961).

c. Oral Administration of Type V Collagen

WKY male rats (180-200 g) were fed with either 10 μg or 50 μg of col(V), col(II) or col(XI) solution dissolved in 0.5 ml of saline by a gastric gavage utilizing a 16-gauge ball-point stainless steel animal feeding needle (Braintree Scientific, Braintree, Mass.) as previously described (Stark and Ostrow, 1990). Control animals were fed with diluent alone. Animals were fed every other day for either eight or four feedings. This dosage of collagen was chosen because of its effectiveness in oral tolerance induction in non-transplantation studies in rats (Yoshino et al. 1995). Seven days after the last feeding, these rats received F344 lung allografts by orthotopic transplantation. WKY lung grafts transplanted into WKY recipients (isografts) were controls.

d. Delayed-type Hypersensitivity (DTH) Response

DTH responses were determined by a modification of procedures described by Sayegh et al., 1992; Yoshino et al., 1995; and Yamagami et al., 1999. In brief, two weeks post-lung transplantation, control or col(V)-fed WKY rats received 10$^7$ irradiated (3000 rad) donor-derived F344 or third party (BN) splenocytes in 30 μl of PBS into the right pinnae by subcutaneous (s.c.) injection using a 26 gauge needle. The left pinnae received an equal volume of diluent to serve as the control site. A separate group of naïve or allograft recipient WKY rats were tested with 15 μg of col(V) in 30 μl volume injected into the right pinnae and diluent into the left. Naïve WKY rats were negative controls. The ear thickness was measured with a micrometer caliper (Mitutoyo, Field Tool Supply, Chicago, Ill.) in a blinded fashion immediately before and 24 hr after injection. Antigen-specific DTH response was calculated according to the following formula: specific ear swelling=(right ear thickness @ 24 hr−right ear thickness @ 0 hr)−(left ear thickness @

24 hr–left ear thickness @ 0 hr)×10$^{-3}$ mm (Yamagami et al., 1999). All data reported as the mean of triplicate measurements.

e. Transplantation Model

The orthotopic transplantation of left lung isografts (WKY- >WKY), or allografts (F344- >WKY) was performed as previously reported (Sekine et al., 1997), utilizing a procedure initially described by Marck et al., (1983) and Prop et al., (1985). Similar to the inventors prior report (Sekine et al., 1997), survival exceeded 90% in all transplantation groups. No immunosuppressive therapy was given at any time during the experimental period.

Transplanted lungs were monitored by serial chest radiographs on days 1, 6, and 13 post-transplantation. The radiographic changes were graded as follows: grade 1, normal; grade 2, mild infiltrates; grade 3, moderate infiltrates; and grade 4, severe infiltrates or complete opacification.

Five transplantation groups were studied: lungs from WKY rats transplanted into WKY recipients (WKY->WKY, control isografts); F344 lungs transplanted into diluent fed WKY recipients (F344->WKY, control allografts); F344 lungs transplanted into col(V)-fed WKY recipients (F344->col(V)-fed WKY, col(V)-fed allografts); F344 lungs transplanted into col(II)-fed WKY recipients (F344- >col(II)-fed WKY, col(II)-fed allografts); and F344 lungs transplanted into col(XI)-fed WKY recipients (F344- >col(XI)-fed WKY, col(XI)-fed allografts). Preliminary experiments showed that diluent feeding had no effect on development of allograft pathology, bronchoalveolar lavage (BAL) differential cell counts, or DTH responses compared to allografts transplanted into unfed WKY rats.

f. Collection of BAL

Collection of BAL fluid was performed in ketamine-anesthetized lung transplant recipients one and two weeks after transplantation (Sekine et al., 1997). In brief, BAL of native and transplanted lungs were performed by selective cannulation of right and left mainstem bronchi with a 16-gauge catheter secured by suture. While clamping the contralateral bronchus, 3 ml aliquots of sterile PBS (37° C.) were instilled into each main stem bronchus and aspirated. Cell-free BAL supernatants obtained from centrifuged specimens was stored at −70° C. until use. BAL fluid differential cell counts were performed utilizing light microscopy to count 300 cells/high power field on cytospin preparations to determine the quantity of macrophages, lymphocytes, and polymorphonuclear (PMN) cells.

g. Pathological Grading

Transplanted lungs from each group were harvested, fixed by an intratracheal instillation of 4% glutaraldehyde, sectioned, stained with hematoxylin and eosin, examined under light microscopy, and graded according to the histologic criteria established by the Lung Rejection Study Group (Yousem et al., 1990) in a blinded fashion without prior knowledge of the transplantation group as previously reported (Sekine et al., 1997).

h. Statistics

Analyses of PMN and lymphocyte counts in BAL fluid were performed initially by ANOVA to determine if differences were present amongst groups. If differences were found than a post hoc analysis utilizing a Student-Newman-Keuls test was performed to determine which group was different. P values<0.05 were determined to be significant. Since data for DTH in control allograft and naïve WKY rats challenged with different antigens was found to be non-normally distributed, a rank-sum two way ANOVA with interaction was utilized to determine differences amongst groups. P values<0.05 were determined to be significant. Differences in DTH responses to donor alloantigens between control allografts and col(V)-fed allografts were determined utilizing a Mann-Whitney U test. P values<0.05 were determined to be significant. Differences between airway and vascular pathologic scores were determined initially utilizing the Kruskal-Wallis test followed by a post hoc analysis utilizing the Mann-Whitney U test. P values<0.03 were determined to be significant.

i. Results

Figure 8:
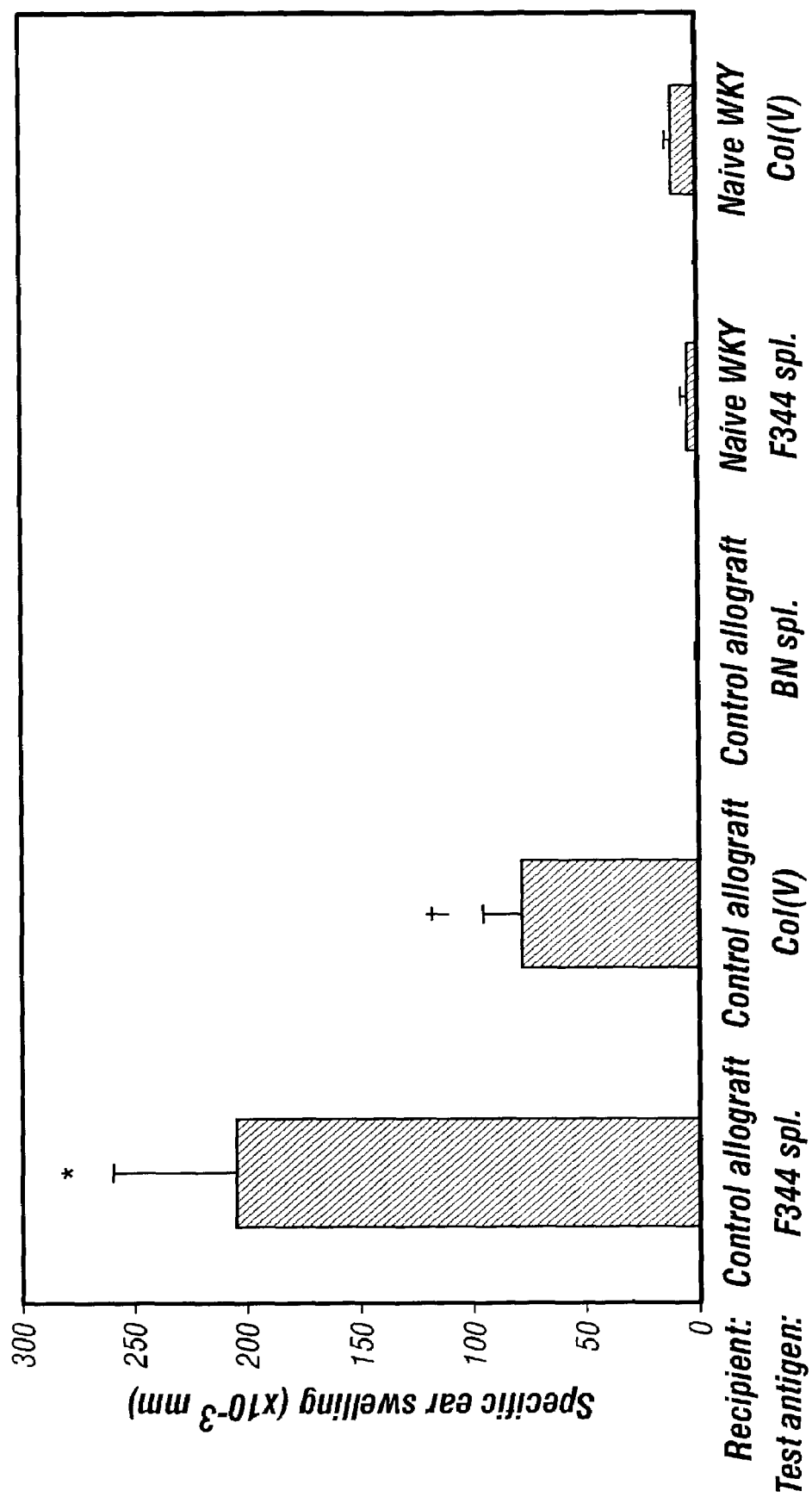
FIG. 8. Reduction of DTH responses to donor alloantigens, col(V), and third party alloantigens in control allograft recipients two weeks post-transplantation. Naïve WKY rats were controls. Animals received $10^7$ irradiated (3000 rad) donor-derived F344 splenocytes, third party (BN) splenocytes, or 15 μg of col(V) into the right pinnae and diluent into the left pinnae. The ear thickness was measured with a micrometer caliper (Mitutoyo, Field tool Supply, Chicago, Ill.) in a blinded fashion immediately before and 24 hr after injection and the specific ear swelling calculated as described in Methods. Data represent the mean±SEM of specific ear swelling in mm×$10^{-3}$ of four rats in each group. [*$p<0.0001$ compared to naïve WKY rats challenged with F344 splenocytes or col(V) and $^†p<0.0001$ compared to naïve WKY rats challenged with col(V) or F344 splenocytes]

The inventors have previously shown that col(V) is a target of the local immune response to lung alloantigens in mice. Therefore, in the present invention the inventors first demonstrated that col(V) is recognized as an antigen during lung allograft rejection. DTH responses have been reported to correlate with the extent of rejection in various rodent models of organ transplantation other than the lung (Van-Buskirk et al., 1998; Lowry et al., 1985; 1985; Joo et al., 1995). However, there are no prior reports of DTH responses in lung allograft recipients. As an in vivo test of the cellular immune response, the systemic DTH response to alloantigen was performed. The inventors examined the DTH responses to F344 splenocytes, col(V), and BN splenocytes (third party) in WKY rats two weeks after receiving F344 lung allografts and in naïve, non-transplanted WKY rats. FIG. 8 shows that WKY rats that received F344 allografts had significant DTH responses to F344 splenocytes [p<0.0001 compared to naïve WKY rats tested with either F344 splenocytes or col(V)]. WKY rats that received F344 allografts also had significant DTH responses to col(V) [p <0.0001 compared to naïve WKY rats tested with either F344 splenocytes or col(V)] (FIG. 1). Statistically, there were no differences between the DTH responses of control allografts to F344 splenocytes and col(V) (p>0.05). Data showing that WKY rats that received F344 lung allografts had no DTH response to third party alloantigens (BN splenocytes, RT1") demonstrates that the immune response to F344 allografts is allo-specific. In addition these data also show that col(V) is recognized as an antigen during lung allograft rejection.

Prior reports have shown that oral administration of antigens that are targets of the immune response during rejection of allografts, other than the lung, induces tolerance to the donor organ (Sayegh et al., Hancock et al., 1993; Ishido et al., 1999). To determine if oral administration of col(V) to lung allograft recipients prior to transplantation induces immunological tolerance to the donor lung, WKY recipients were fed col(V) prior to transplantation as described above. Preliminary experiments demonstrated that eight feedings of 10 μg of col(V) every other day (total dose of 80 μg) followed by left orthotopic lung transplantation seven days after the last feeding had the greatest effect on the BAL cell counts and rejection pathology in this model. Therefore, this feeding regimen was utilized for all subsequent studies. Col(V)-fed recipients underwent left lung transplantation and were harvested at the completion of the experimental period as described above.

Figure 9:
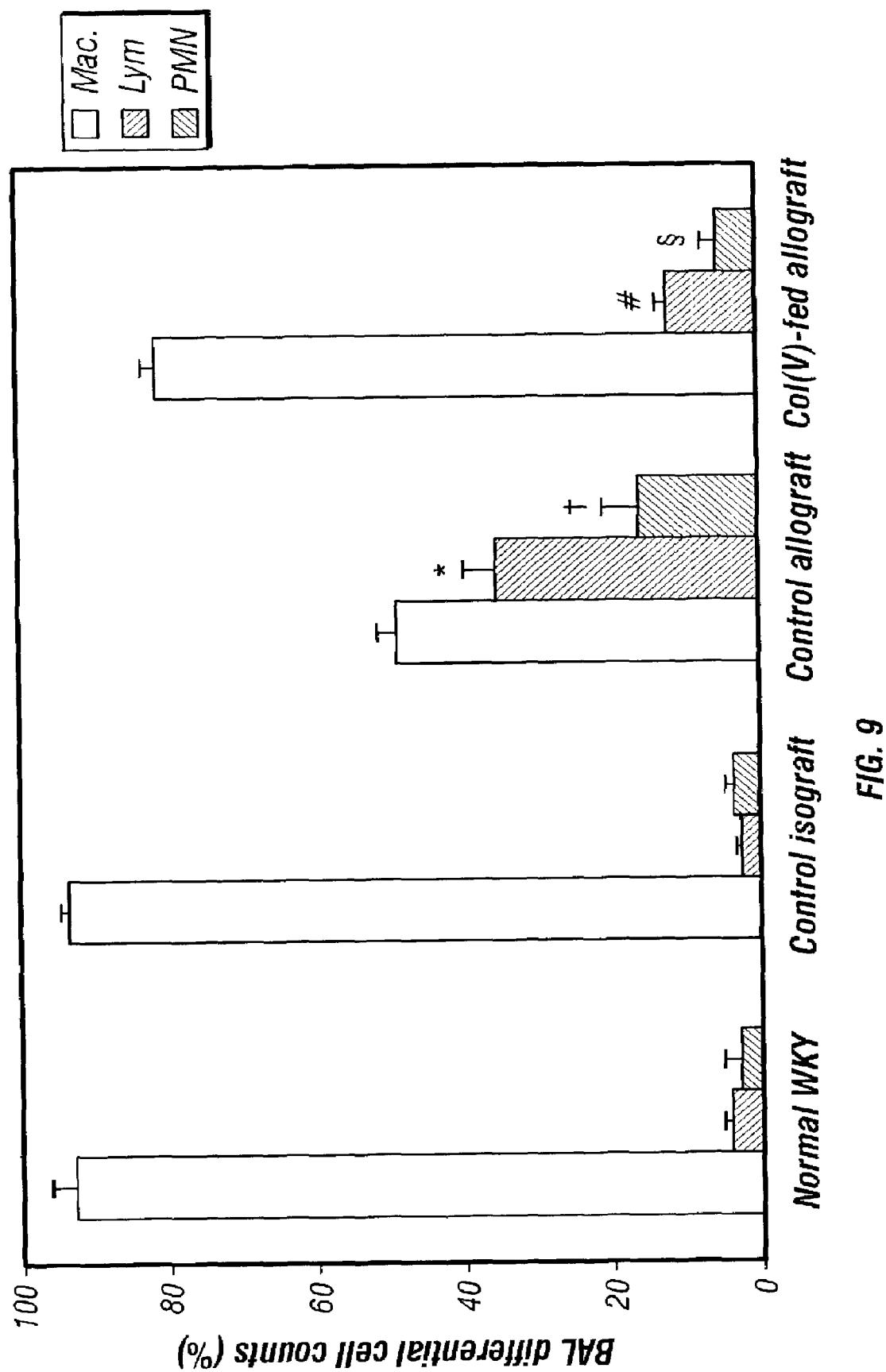
FIG. 9. BAL fluid differential cell counts in normal WKY lungs, control isograft lungs, control allograft lungs, and col(V)-fed allograft lungs. At two weeks post-transplantation, transplanted lungs underwent BAL, as described in Methods. Differential cell counts were determined by counting 300 cells/field on cytospin preparations utilizing light microscopy. Mac, macrophages; Lym, lymphocytes; PMN, polymorphonuclear cells. Data represent the mean±SEM of four normal WKY lungs, four control isografts, five control allografts, and five col(V)-fed allografts. (*$p<0.038$ for PMN's and $^†p<0.000001$ for lymphocytes compared to normal or isograft lungs, $^\#p<0.023$ for PMN's and $^§p<0.0001$ for lymphocytes compared to control allografts).

FIG. 9 shows the differential cell counts in BAL fluid from transplanted lungs of control WKY isograft recipients, control WKY allograft recipients, and col(V)-fed WKY allograft recipients two weeks post-transplant, and normal WKY rats. There were no differences in BAL differential cell counts in normal compared to isograft lungs. Similar to prior reports (Prop et al., 1985; Yagyu et al, 1990), PMN's and lymphocytes were significantly increased in control allograft BAL compared to normal or isograft lungs (p<0.039 for PMN's and p<0.00001 for lymphocytes ). In contrast, feeding col(V) prior to transplantation resulted in a significant reduction in BAL PMN's and lymphocytes compared to control allografts (p<0.023 for PMN's and p<0.0001 for lymphocytes). Acute allograft rejection is usually associated with an increase of total cell counts in allograft BAL fluid (Matsumura et al, 1995; Hirt et al., 1999). However, at two weeks post-transplant, the control WKY allograft lungs are usually undergoing severe rejection and due to destruction of the allograft, sufficient BAL could not be performed reliably to determine BAL total cell counts. In contrast, col(V)-fed allograft recipients showed less severe rejection which allows easier BAL resulting in higher cell counts. For these reasons, comparison of total cell counts between the groups could not be done. Collectively, these data demonstrate that oral immunization with col(V) is associated with fewer PMN's and lymphocytes in allograft BAL fluid during acute rejection.

To determine if col(V) feeding diminished DTH responses to alloantigens, control WKY allograft recipients and col(V)-fed WKY allograft recipients were challenged in the right pinnae with whole allogeneic (F344) splenocytes and PBS in the left pinnae. The DTH response was measured 24 hr later and the specific ear swelling was determined. As shown in FIG. 8, untreated control WKY allograft recipients undergoing severe acute rejection had a strong DTH response after challenge with donor antigen. In contrast, the col(V)-fed WKY allograft recipients that had less severe allograft rejection also had a significant reduction of the DTH response to donor antigens (FIG. 4, *p<0.02 compared to control WKY allograft).

The impaired immune response to alloantigen induced by col(V) could have been due to global immune hyporesponsiveness (Faria and Weiner 1999), and not tolerance. Therefore, to determine if col(V)-fed WKY rats could respond to other antigens, these rats received lipopolysaccharide (LPS) (Sigma, St. Louis, Mo.) either intratracheally (200 ug/kg to 1 mg/kg) or intravenously (1-5 mg/kg), which are doses known to induce severe inflammatory reactions in the lung and systemically 24 to 48 h after injection or instillation (O'Leary et al. 1997; Delclaux et al. 1997). Rats were challenged one week after last feeding of col(V). The disease induced is analogous to pneumonia and sepsis caused by gram-negative bacteria. Similar to normal WKY rats, instillation of LPS into lungs or injected I.V. into col(V)-fed WKY rats induced severe illness (ruffled fur and prostration) and inflammation in recipient lungs. These data show that feeding col(V) prior to transplantation prevented allograft rejection by inducing tolerance, and not global immune hyporesponsiveness, to donor antigens.

Collectively, these data show that col(V), but not col(II) or col(XI), down-regulates lung allograft rejection by induction of oral tolerance and not global immune hyporesponsiveness. Furthermore, oral tolerance induced by col(V) down-regulates DTH responses to donor alloantigens.

Diminished PMN and lymphocyte counts in allograft BAL fluid is associated with less severe radiographic and histologic lesions during acute lung allograft rejection. To determine the rate of progression of lung infiltrates, transplant recipients were monitored by serial chest radiographs on days 1, 6, and 13 post-transplantation and graded as described above. Control isografts did not have any pulmonary infiltrates at all monitored time points (FIG. 9A). In the control allografts serial x-rays revealed gradual development of infiltrates in the left lung at 6 days post-transplant which resulted in severe infiltrates and complete opacification of the allograft by the end of the second week (FIG. 9B). However in col(V)-fed allografts the development of infiltrates was much slower compared to controls. The x-rays were normal at day 6 and only mild infiltrates were present at two weeks post-transplantation (FIG. 9C).

The upper panels of FIG. 11 show the gross anatomy of the native and isograft WKY lungs, and the native and allograft lungs from control allograft and col(V)-fed allograft rats harvested at two weeks post-transplantation. FIG. 11A shows that the isograft (left-L) and the native lung (right-R) of WKY rat recipient are normal in appearance. In contrast, the left allograft lung in the control allograft group was dark brown in color, shrunken, and of a firm consistency compared to the native lung (FIG. 11B). As a result of inflammation and rejection, fusion of the parietal and visceral pleura was usually observed in control allograft lungs. The transplanted left lung in col(V)-fed allograft recipients (FIG. 11C) had the appearance of the native (normal) or isograft lung (FIG. 11A) and no pleural adhesions.

Figure 11A:
FIG. 11A, FIG. 11B, FIG. 11C, FIG. 11D, FIG. 11E, and FIG. 11F. Upper panel: Gross anatomy of control isograft lungs FIG. 11A, control allograft lungs FIG. 11B, and col(V)-fed allograft lungs FIG. 11C two weeks post-transplantation (posterior view). The left (L) lung is the transplanted lung and the right (R) is the native lung in each panel. The control allograft lung ("L" in panel b) was dark brown in color, shrunken, and of firm consistency compared to the native lung. However, the col(V)-fed allograft lung ("L" in panel c) had the appearance of the isograft lung ("L" in panel a). Control isograft lungs (FIG. 11A) show no pathologic lesions and are identical to normal WKY lungs. Photographs representative of five rats in each group. Lower panel: Histology of control isografts FIG. 11D, control allografts FIG. 11E, and col(V)-fed allografts FIG. 11F two weeks post-transplantation. Control isografts show normal airway and vascular structures (FIG. 11D). Control allografts show extensive perivascular, peribronchial, and alveolar mononuclear cell infiltrates consistent with severe rejection (FIG. 11E). In contrast, col(V)-fed allografts show only mild to moderate perivascular and peribronchial mononuclear cell infiltrates (FIG. 11F). Photomicrographs representative of five rats in each group (100× magnification).
Figure 11B:
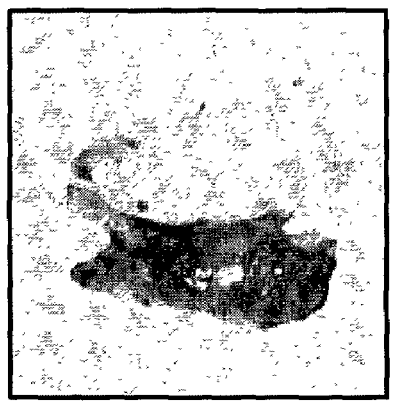
Figure 11C:
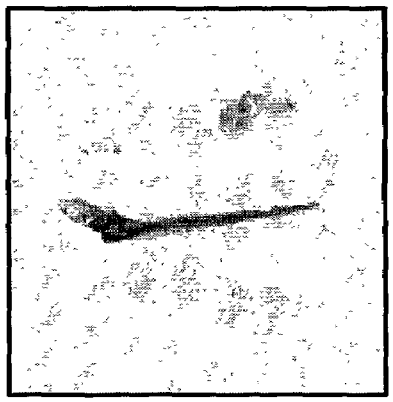
Figure 11D:
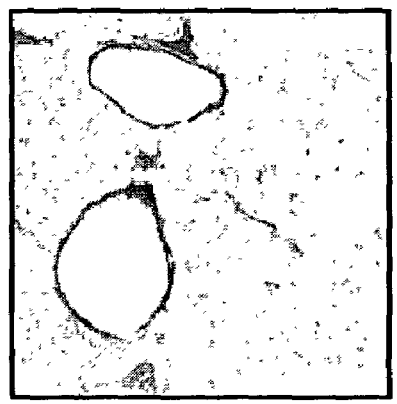
Figure 11E:
Figure 11F:
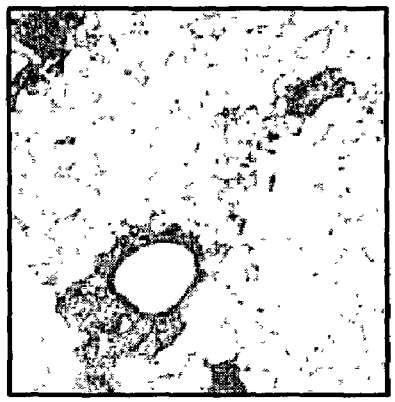

Fewer PMN's and lymphocytes in allograft BAL fluid, less severe infiltrates in the allografts on chest x-ray, and preserved gross anatomy suggested that feeding col(V) prior to transplantation down-regulated development of rejection pathology. The lower panels of FIG. 11 show the representative histology of control isografts, control allografts, and col(V)-fed allografts two weeks post-transplantation. Similar to prior reports (Joo et al., 1995; Prop et al., 1985), all control isograft lungs had normal histology without signs of rejection (FIG. 11D). Control allografts revealed extensive perivascular, peribronchial, and alveolar mononuclear cell infiltrates consistent with severe acute rejection (FIG. 11E). In contrast, only mild to moderate perivascular and peribronchial infiltration were detected in the col(V)-fed allograft lungs (FIG. 11F).

Fewer PMN's and lymphocytes in allograft BAL fluid, less severe infiltrates in the allografts o chest x-ray, and preserved gross anatomy suggested that feeding col(V) prior to transplantation down-regulated development of rejection pathology. The lower panels of FIG. 10 show the representative histology of control isografts, control allografts, and col(V)-fed allografts two weeks post-trasplantation. Similar to prior reports (Joo et al., 1995; Prop et al., 1985), all ocntrol isograft lungs had normal histology without signs of rejection (FIG. 1-D). Control allografts revealed extensive perivascular, peribronchial, and alveolar mononuclear cell infiltrates consistent wiht severe acute rejection (FIG. 10E). In contrast, only mild to moderate perivascular and peribronchial infiltration were detected in the col(V)-fed allograft lungs (FIG. 10F).

Table 3 shows the grading of rejection pathology at two weeks post-transplantation using standard criteria. Acute vascular rejection was graded in A0-A4 according to the presence and extent of perivascular mononuclear cell infiltrates, and acute airway rejection graded B0-B4 according to the extent and intensity of airway inflammation (Yousem et al. 1996). All isograft control lungs revealed normal structure of the lung (A0±0, B0±0). The control WKY allografts had severe vascular and airway rejection (A3.8±0.2, B4±0, respectively). In contrast, col(V)-fed WKY allografts showed mild to moderate vascular and airway rejection (A2.8±0.2, B2.6±0.2, respectively). Col(II) and col(XI) fed allografts had rejection pathology similar to untreated allografts (Table 3). These data show that col(V)-fed WKY allografts had less severe rejection pathology than all other allografts (p<0.028 for A scores and p<0.009 for B scores).

TABLE 3

Grading of Rejection Pathology

| Group | A (acute rejection) | B (airway inflammation) |
|---|---|---|
| Control WKY isograft | 0 ± 0 | 0 ± 0 |
| Control WKY allograft | 3.8 ± 0.2 | 4.0 ± 0 |
| Col(II)-fed WKY allograft | 3.9 ± 0.3 | 4.0 ± 0 |
| Col(XI)-fed WKY allograft | 3.9 ± 0.1 | 4.0 ± 0 |
| Col(V)-fed WKY allograft | 2.8 ± 0.2* | 2.6 ± 0.2† |

Grading of rejection pathology in control isografts, control allografts, and col(V)-fed allografts at two weeks post-transplantation. Acute rejection was graded in A0-A4 according to the presence and extent of perivascular and interstitial mononuclear infiltrates, and B0-B4 according to the extent and intensity of the airway inflammation. All control isografts lungs revealed normal structure of the lung. Col(V)-fedallografts had less severe rejection pathology compared to control allografts (*$p < 0.028$ for A scores and †$p < 0.009$ for B scores, col(V)-fed allografts compared to control allografts). Data represent the mean ± SEM of pathologic scores of five rats.

Data showing that feeding col(V) down-regulates lung allograft rejection indicates that orally tolerized lung allograft recipients should have a diminished DTH response after re-challenge with donor alloantigens. To determine if col(V) feeding diminished immune responses to alloantigens, control allograft recipients and col(V)-fed allograft recipients were challenged in the right pinnae with whole allogeneic F344 splenocytes and PBS in the left pinnae. The DTH response was measured 24 hr later and the specific ear swelling was determined. As shown in FIG. 11, untreated control allograft recipients undergoing severe acute rejection had a strong DTH response after challenge with donor antigen (same data for control allografts shown in FIG. 8). In contrast, the col(V)-fed allograft recipients had a significantly reduced DTH response to donor antigen ($p<0.02$ compared to control allograft). These data indicate that feeding col(V) prior to transplantation prevented allograft rejection by inducing tolerance to donor antigens.

Two weeks post-transplantation, the time of onset of severe rejection (grade 4), allograft lungs underwent BAL for determination of differential cell counts, and collection of serum. Native and transplant lungs were harvested en bloc, fixed, sectioned, stained, and graded for rejection pathology using standard criteria (Yousem et al. 1996). All interpretations and grading of rejection pathology were performed by Oscar W. Cummings, M.D., pulmonary pathologist, who was blinded to the treatment groups, as previously reported (Sekine et al. 1997; Mares et al. In Press; Wilkes et al. 1998). FIG. 11 shows the gross anatomy of isograft WKY lungs and the native and allograft lungs from control WKY allografts, and col(V)-fed WKY allograft recipients harvested at two weeks post-transplantation. In control WKY allograft animals, FIG. 11B shows that the transplanted (left) lung was dark brown in color, and shrunken compared to the native lung. In contrast, the transplanted left lung in col(V)-fed WKY allograft recipients (FIG. 11C) had the appearance of the native (normal) or isograft lung (FIG. 11A). The gross appearance of allografts lungs in WKY rats fed col(II), or col(XI) was similar to untreated allograft lungs. As expected, isograft lungs appeared normal (FIG. 11A).

FIG. 11 also shows histology of control WKY isografts, control WKY allografts, and col(V)-fed WKY allografts two weeks post-transplantation. WKY isograft lungs had normal histology (FIG. 11D). Control WKY allografts revealed extensive perivascular, peribronchial, and alveolar mononuclear cell infiltrates consistent with severe acute rejection (FIG. 11E). In contrast, only mild to moderate perivascular and peribronchial infiltration were detected in the col(V)-fed WKY allograft lungs (FIG. 11F). Allografts lungs in WKY rats fed col(II) or col(XI) had pathology similar to untreated allograft lungs (see Table 3).

Although, oral tolerance has been shown to be of benefit in down-regulating alloreactivity in organs other than the lung (Sayegh et al., 1992; Hancock et al., 1993; Ishido et al., 1999), oral tolerization in lung transplantation has not been reported previously. Utilizing a rat model of lung transplantation, data in the present invention show that oral administration of col(V) to lung allograft recipients prior to lung transplantation down-regulates rejection responses. Immunological, radiological, and histological analysis of col(V)-fed compared to control allograft recipients show that feeding col(V) is associated with diminished PMN and lymphocyte counts in allograft BAL fluid, less severe infiltrates in the allografts on chest x-ray, preservation of gross anatomy of the allograft, and reduction of rejection pathology. Finally, orally tolerized allograft recipients have diminished DTH responses to donor alloantigens.

The inventors have shown previously that col(V) is a target of the local immune response to alloantigens in mice. Col(V) is a minor type collagen present in the lung, located in the peribronchiolar connective tissues, alveolar interstitium, and capillary basement membrane. These tissues have been shown to be sites of pathologic lesions in response to alloantigens in the inventors murine model (Wilkes et al., 1995; Wilkes et al., 1999) and are sites of rejection activity in human lung allograft recipients (Trulock, 1997).

Oral administration of antigens is an effective method of inducing peripheral T-cell tolerance. This phenomenon, often referred to as oral tolerance, has been well studied in various models of autoimmune diseases in animals including encephalomyelitis, uveitis, diabetes, myasthenia gravis, and arthritis. However, the mechanisms for inducing tolerance are not completely understood. All of the known mechanisms for tolerance induction, including clonal anergy, clonal deletion, and regulation by IL-4, IL-10, or TGF-beta-mediated active suppression may have a role in oral tolerance (Faria and Weiner, 1999). Generally, higher doses of antigen are reported to induce anergy or clonal deletion (Chen et al., 1995; Whitacre et al., 1991), whereas low doses induce cytokine regulation and active suppression (Faria and Weiner, 1999; Chen et al., 1994). In the animal model of cardiac transplantation, oral administration of allogeneic splenocytes has been shown to be effective in tolerance induction by bypassing Th1 activation and selectively stimulating induction of Th-2 derived inhibitory cytokines such as IL-4 (Hancock et al., 1993; Ishido et al., 1999).

Inbred, pathogen-free, MHC (RT1)-incompatible male F344 (RT1$^{1v1}$) and WKY (RT1$^1$) rats (250-300 g) were utilized for transplantation surgery. All rats were purchased from Harlan Sprague Dawley (Indianapolis, Ind.). The orthotopic transplantation of left lung allografts was performed as previously reported (Sekine et al. 1997), and utilized a procedure described by Marck and colleagues (1983). No rats receive any immunosuppression. Rejection pathology was graded at various time points post-transplantation. The F344→WKY transplant model is associated with development of mild acute rejection (grade 1) by the end of the first week, moderate to severe rejection (grade 2-3) by the end of the 2$^{nd}$ week, and severe—grade 4 rejection by the end of the 3$^{rd}$ week post-transplantation (Matsumura et al. 1995; Zuo et al. 1995). In addition, the F344→WKY model is the only animal model of lung transplantation that develops bronchiolitis obliterans (BO) reproducibly (Hirt et al. 1999). Therefore, this model offers the unique opportunity to study the pathogenesis of acute and chronic rejection.

In the present invention, different feeding regimens were tested to observe any differences in the induction of oral tolerance. Data show that the multiple feedings of low dose of col(V) (10 μg) were more suppressive of rejection episodes compared to higher doses (50 μg). Thus, in the inventors model of oral tolerance, regulation by Th2 cytokines (IL-4, IL-10) or activated suppression mediated by TGF-beta may also play an important role in tolerance induction.

The induction of transplantation tolerance has become a major goal of transplant research, and over the years different techniques have been utilized to induce transplantation tolerance. Donor specific blood transfusion (Zheng et al., 1999), bone marrow transplantation (Huang et al., 2000), thymic injection of allogeneic cells (Garrovillo et al., 1999), or systemic immunization with donor MHC derived peptides (Sayegh and Krensky, 1996) have been shown to induce transplantation tolerance in various animal models. However, these techniques would have limited utility in the potential lung allograft recipient due to the fact that the donor cells utilized for tolerance induction would not be available in sufficient time to induce tolerance prior to transplantation. In experimental autoimmune models of low dose oral tolerance, regulatory cells following oral tolerization are triggered in an antigen-specific fashion but suppress in an antigen nonspecific fashion. Therefore, it may not be necessary to identify the target autoantigen itself, but it might suffice to orally administer a protein capable of inducing regulatory cells that secretes suppressive cytokines (Faria and Weiner, 1999). The inventors model of oral tolerance in lung transplantation shows that orally administered col(V), which is not donor-specific, is capable of suppressing alloreactivity and inducing transplantation tolerance. The inventors envision that the oral treatment of transplant recipients with col(V) prior to transplantation will provide therapy for preventing rejection in lung transplantation.

Example 4

Elucidation of Additional MHC-"like" Peptides and Collagens for Use to Prevent Allograft Rejection and to Tolerize Animals a. Animals Pathogen-free, MHC (RT1)-incompatible male rats were utilized for the study: Wistar Kyoto (WKY, RT1$^1$), Fischer 344 (F344, RT1$^{1v1}$), and Brown Norway (BN, RT1″) rats (250-300 g at the time of transplantation). All rats were purchased from Harlan Sprague Dawley (Indianapolis, Ind.) and housed in the Laboratory Animal Resource Center at Indiana University School of Medicine (Indianapolis, Ind.) in accordance with institutional guidelines.

b. Preparation of Collagens

Collagen type II [col(II)] was isolated from canine cartilage as previously reported (Mares et al. 2000; Smith et al. 1985), or purchased from Collaborative Biomedical Products, Bedford, Mass. Both preparations were solubilized in 0.005M acetic acid and dialyzed to yield a final concentration of 0.5 mg/ml.

Bovine collagen type XI [col(XI)] from fetal calf cartilage (Morris and Bachinger 1987) was purchased from Biogenesis, Sandown, N.H. and diluted in 0.005M acetic acid (0.5 mg/ml) and stored at 4° C. until use.

Human type V collagen [col(V)], extracted from human placenta and purified by differential NaCl precipitation (Mares et al. 2000), was a gift from Dr. Jerome Seyer (VA Hospital, Hampton, Va.). In brief, placental tissues were minced, washed, and suspended in 0.5 M acetic acid containing 0.5 M NaCl, and digested by pepsin at 4° C. Supernatants were aspirated from centrifuged specimens, the pellet collected and the extraction procedure repeated. The supernatants were combined from the two digests, and col(V) was purified from the supernatants by differential NaCl precipitation from 0.5 M acetic acid (Mares et al. 2000; Smith et al. 1985). The intact col(V) was diluted in 0.005M acetic acid (0.5 mg/ml) until use.

The quantity of collagens was assessed by determination of the hydroxyproline content in the samples as previously reported (Mares et al. 2000).

c. Oral Administration of Collagen

WKY rats were fed with 10 μg of col(II), col(V), or col(XI) dissolved in 0.5 ml of saline by a gastric gavage utilizing a 16-gauge ball-point stainless steel animal feeding needle (Braintree Scientific, Braintree, Mass.). Control animals were fed with diluent alone. Animals were fed every other day for eight feedings. This dose of collagen was chosen because of its effectiveness in oral tolerance induction in non-transplantation studies in rats (Yoshino et al. 1995). Seven days after the last feeding, these rats were utilized as recipients of lung allografts (described below).

d. Transplantation Model

The orthotopic transplantation of left lung isografts (WKY→WKY), or allografts (F344→WKY) was performed as previously reported (Sekine et al. 1997), utilizing a procedure initially described by Marck et al. (1983), and Prop et al. (1985). In brief, after the donor rats (F344 or WKY) were anesthetized with an i.m. injection of ketamine (40 mg/kg) and xylazine (5 mg/kg), the chest was shaved, sternotomy incision made, and the heart and lungs were removed en bloc. The left lung was than resected and heparinised Lactated Ringer's solution was infused into the pulmonary artery. The donor lung was wrapped in sterile gauze saturated with saline and placed on ice (4° C.) in a sterile beaker until transplantation.

The recipient rats were anesthetized with an s.c. injection of atropine (0.05 mg/kg), followed by an inhalation of 2% halothane. The airway was cannulated with a 14-gauge Teflon catheter and the rat was mechanically ventilated with a rodent ventilator (Analytical Specialties Co., St. Louis, Mo.) utilizing 100% oxygen, and the inhalation of 1.5-2% isoflurane for maintenance anesthesia. Once a thoracotomy incision was made in the left 4$^{th}$ intercostal space, and hemostats placed on the left pulmonary vessels and bronchus, the left lung was resected. The pulmonary vessels of the donor lung were anastomosed to the recipient by a plastic cuff and 7-0 silk sutures (Kono, Chiba, Japan). The donor and recipient bronchi were sutured together utilizing 8-0 Prolene sutures (Ethicon, Sommerville, N.J.). Immediately after completion of the anastomosis of the bronchus, the hemostat was removed and ventilation was restored. After the left thoracotomy incision was closed over a 16-gauge chest tube utilizing 3-0 silk suture (Ethicon), maintenance anesthesia was discontinued and the animal was allowed to recover. Once spontaneous respiration resumed, the cannula was removed from the airway, and the chest tube removed. The ischemic time of the donor lung was approximately 1 h and the total operating time for harvesting and transplanting the donor lung was approximately 2 h. All transplantation procedures were performed by K. Y. under a surgical microscope (Micro Tech, Colorado Springs, Colo.) under sterile conditions. The F344→WKY transplant model is associated with the development of mild acute rejection by the end of the first week and moderate to severe acute rejection by the end of the second week (Matsumura et al. 1995). Survival exceeded 90% in all transplantation groups. No immunosuppressive therapy was given at any time during the experimental period.

Transplanted lungs were monitored by serial chest radiographs on days 1, 6, and 13 post-transplantation. The radiographic changes were graded as follows: grade 1, normal; grade 2, mild infiltrates; grade 3, moderate infiltrates; and grade 4, severe infiltrates or complete opacification.

Five transplantation groups were studied: lungs from WKY rats transplanted into WKY recipients [control isografts]; F344 lungs transplanted into diluent fed WKY recipients [control allografts]; F344 lungs transplanted into col(V)-fed WKY recipients [col(V)-fed allografts]; F344 lungs transplanted into col(II)-fed WKY recipients [col(II)-fed allografts]; and F344 lungs transplanted into col(XI)-fed WKY recipients [col(XI)-fed allografts].

e. Collection of Bronchoalveolar Lavage (BAL) Fluid

Collection of bronchoalveolar lavage (BAL) fluid was performed in ketamine-anesthetized lung transplant recipients two weeks after transplantation as previously reported (Sekine et al. 1997). In brief, BAL of native and transplanted lungs were performed by selective cannulation of right and left mainstem bronchi with a 16-gauge catheter secured by suture. While clamping the contralateral bronchus, 3 ml aliquots of sterile PBS (37° C.) were instilled into each main stem bronchus and aspirated. Cell-free BAL supernatants obtained from centrifuged specimens was stored at −70° C. until use. BAL fluid differential cell counts were performed utilizing light microscopy to count 300 cells/high power field on cytospin preparations to determine the quantity of macrophages, lymphocytes, and polymorphonuclear (PMN) cells.

f. Delayed-Type Hypersensitivity (DTH) Response

DTH responses were determined by a modification of a procedure described by Yamagami et al. (1999). In brief, two weeks post-lung transplantation, control or col(V)-fed WKY rats received $10^7$ irradiated (3000 rad) donor-derived F344 or third party (BN) splenocytes in 30 µl of PBS into the right pinnae by s.c. injection using a 26 gauge needle. The left pinnae received an equal volume of diluent, and served as the control site. Naïve WKY rats were negative controls. A separate group of naïve or allograft recipient WKY rats were tested with 15 µg of col(II), col(V), or col(XI) in 30 µl volume injected into the right pinnae and diluent into the left. The ear thickness was measured with a micrometer caliper (Mitutoyo, Field Tool Supply, Chicago, Ill.) in a blinded fashion immediately before and 24 h after injection. Antigen-specific DTH response was calculated according to the following formula: Specific Ear Swelling=(right ear thickness @ 24 h—right ear thickness @ 0 h)–(left ear thickness @ 24 h–left ear thickness @ 0 h)×$10^{-3}$ mm (Yamagami et al. 1999). All data reported as the mean of triplicate measurements.

In separate experiments, naïve and col(V)-fed WKY rats were primed with 100 µg of low endotoxin bovine serum albumin (BSA) (Sigma, St. Louis) dissolved in 100 µl of an emulsion of adjuvant (Titermax, CytRx Corp., Norcross, Ga.). Each rat was primed s.c. with the emulsion at the base of the tail. Seven days later rats were challenged with 2% heat aggregated BSA solution into the right pinnae and diluent into the left (Henningsen et al. 1984). Unprimed rats were controls for these studies. The ear thickness was measured immediately before and 24 h after injection and the Specific Ear Swelling calculated as described above.

g. Neutralization of TGF-β, IL-4, and IL-10 in DTH Assays

Neutralization of TGF-β at the DTH site was performed by a modification of a procedure described by Bickerstaff et al. (2000). In brief, two weeks post-lung transplantation, col(V)-fed WKY rats received $10^7$ irradiated (3000 rad) donor-derived F344 splenocytes mixed with 5 µg of polyclonal chicken anti rat TGF-β Ab, or 5 µg of polyclonal goat anti rat IL-4 or IL-10 Ab (all R&D Systems, Minneapolis, Minn.) in 30 µl of PBS into the right pinnae by s.c. injection using a 26 gauge needle. The left pinnae received an equal volume of diluent, and served as the control site. For negative controls, a separate group of col(V)-fed allografts received $10^7$ irradiated (3000 rad) donor-derived F344 splenocytes mixed with 5 µg of control chicken immunoglobulins or control goat immunoglobulins (R&D Systems, Minneapolis, Minn.) into the right pinnae and diluent into the left. The Specific Ear Swelling was determined as described above. Control immunoglobulins had no effect on the DTH response.

h. Rat Model of Acute Lung Injury

Alveolar or intravenous instillation of lipopolysaccharide (LPS) (Sigma, St. Louis, Mo.) was performed by a modification of a procedure described by O'Leary et al. (1997). Briefly, normal WKY rats or col(V)-fed WKY rats, one week after last feeding, were anesthetized with a s.c. injection of atropine (0.05 mg/kg), followed by an inhalation of 2% halothane. The airway was cannulated with a 14-gauge Teflon catheter and the rat was mechanically ventilated with a rodent ventilator (Analytical Specialties Co., St. Louis, Mo.) utilizing 100% oxygen, and the inhalation of 1.5-2% isoflurane for maintenance anesthesia. After disappearance of spontaneous respiration, LPS (1 mg/kg at 1 mg/ml) was instilled into the airway and mechanically ventilated for 10 minutes. Maintenance anesthesia was discontinued and the animal was allowed to regain consciousness. Once spontaneous respiration resumed, the cannula was removed from the airway. In separate experiments, rats were injected intravenously into the tail veins with LPS (4 mg/kg at 1 mg/ml). 24 h after challenge, BAL was performed and the lungs were harvested for assessment of pathology.

i. Quantitation of Cytokines

TGF-β levels in serum of the experimental groups were quantitated by ELISA utilizing the TGF-$\beta_1$ immunoassay system (Promega, Madison, Wis.) per manufacture's protocol. IL-4 and IL-10 levels in serum were quantitated by ELISA utilizing Cytoscreen immunoassay kits (BioSource International, Camarillo, Calif.) per manufacture's protocol. The sensitivity of the TGF-β, IL-4, and IL-10 assays were 32, 2, and 5 pg/ml, respectively.

j. Pathological Grading

Native and transplanted lungs from each group were harvested, fixed, sectioned, stained, and graded for rejection pathology using standard criteria (Yousem et al. 1996) by a pathologist (O. W. C.) in a blinded fashion without prior knowledge of the transplantation group as previously reported (Sekine et al. 1997).

k. Statistics

Analyses of PMN and lymphocyte counts in BAL fluid were performed initially by ANOVA to determine if differences were present amongst groups. If differences were found than a post hoc analysis utilizing a Student-Newman-Keuls test was performed to determine which group was different. P values<0.05 were determined to be significant.

Since data for DTH in control allograft and naïve WKY rats challenged with different antigens was found to be non-normally distributed, a rank-sum two way ANOVA with interaction was utilized to determine differences amongst groups. P values<0.05 were determined to be significant. Differences in DTH responses to donor alloantigens between control allografts and col(V)-fed allografts were determined utilizing a Mann-Whitney U test. P values<0.05 were determined to be significant. Differences between airway and vascular pathologic scores were determined initially utilizing the Kruskal-Wallis test followed by a post hoc analysis utilizing the Mann-Whitney U test. P values<0.03 were determined to be significant. The Student's t test for multiple comparison was utilized for analysis of cytokines. P values<0.05 were determined to be significant.

l. Results

DTH responses to donor antigens, an in vivo test of cellular immunity, have been reported to correlate with the extent of rejection in various rodent models of organ transplantation other than the lung (VanBuskirk et al. 1998; Lowry et al. 1985). The present inventor has recently reported that col(V) is a target of the local immune response to lung alloantigens in mice (Mares et al. 2000). Therefore, it was determined that the systemic DTH response to alloantigen in naïve rats and lung allograft recipients to determine if col(V) is recognized as an antigen during lung allograft rejection. It was also determined whether lung allograft recipients develop a DTH response to col(V). DTH responses to F344 (donor) splenocytes and col(V) were examined in WKY rats two weeks after receiving F344 lung allografts, the time at which severe acute rejection begins to develop (Matsumura et al. 1995), and in naïve, non-transplanted WKY rats. To determine the specificity of the DTH response to alloantigens and col(V), DTH responses to col(II), col(XI), and third party antigens, BN splenocytes were determined. Col(II), a major component of the articular cartilage, is not present in the lung, and is not homologous to col(V) (Smith et al. 1985). In contrast col(XI) has homology to col(V) (Morris and Bachinger 1987), but similar to col(II), it is found in articular cartilage and is not present in the lung. For these reasons, col(II) and col(XI) served as controls for col(V).

Utilizing Specific Ear Swelling as a measurement of DTH responses, FIG. 8 shows that control allograft recipients developed significant DTH responses to F344 splenocytes and col(V) two weeks post-transplantation [*$p<0.0001$ compared to naïve WKY rats challenged with F344 splenocytes or col(V), and $^\dagger p<0.0001$ compared to naïve WKY rats challenged with col(V) or F344 splenocytes] (FIG. 8). In contrast, control allografts did not have DTH responses to third party (BN) antigens, col(II), or col(XI) (FIG. 8). Naïve WKY rats did not have DTH responses to col(II), or col(XI). These data confirm other studies showing that DTH responses are indicative of immune activation during allograft rejection, which is specific to donor, but not third party alloantigens (VanBuskirk et al. 1998). In addition, it confirms the present inventor's results in mice (Mares et al. 2000) that col(V), but not col(II) or col(XI), is a target of the immune response to lung alloantigens.

Prior reports have shown that oral administration of antigens that are targets of the immune response during rejection of allografts, other than the lung, induces tolerance to the donor organ (Sayegh et al. 1992; Ishido et al. 1999). To determine if oral administration of collagens to lung allograft recipients prior to transplantation induces immunological tolerance to the donor lung, WKY recipients were fed col(II), col(V), or col(XI) prior to transplantation as described above, followed by an assessment of serial chest x-rays, allograft BAL differential cell counts, pathologic grading, and DTH responses to donor antigens.

FIG. 9 shows the differential cell counts in BAL fluid from the experimental groups two weeks post-transplantation, the time of onset of severe acute rejection (Matsumura et al. 1995), and in normal WKY rats. There were no differences in BAL differential cell counts in normal compared to isograft lungs. Similar to prior reports (Prop et al. 1985; Yagyu et al. 1990), PMN's and lymphocytes were significantly increased in control allograft BAL compared to normal or isograft lungs (*$p<0.00001$ for lymphocytes and $^\dagger p<0.038$ for PMN's compared to normal or isograft lungs) (FIG. 9). In contrast, feeding col(V) prior to transplantation resulted in a significant reduction in BAL PMN's and lymphocytes compared to control allografts ($^\ddagger p<0.0001$ for lymphocytes and $^\S p<0.023$ for PMN's compared to control allografts) (FIG. 9).

Acute allograft rejection is usually associated with an increase of total cell counts in allograft BAL fluid (Matsumura et al. 1995). However, at two weeks post-transplant, the control WKY allograft lungs are usually undergoing severe rejection and due to destruction of the allograft, sufficient BAL could not be performed reliably to determine BAL total cell counts. In contrast, col(V)-fed allograft recipients show less severe rejection which allows easier BAL resulting in higher cell counts. For these reasons, comparison of total cell counts between the groups could not be done. Collectively, these data demonstrate that oral immunization with col(V) is associated with fewer PMN's and lymphocytes in allograft BAL fluid during acute rejection.

Figure 10C:
FIG. 10A, FIG. 10B, and FIG. 10C. Serial chest x-rays of transplant recipients two weeks post-transplantation. The short-white lines in the left lung field (arrowheads) represent the cuffs used for vascular anastomoses. Control isograft recipients show normal chest x-rays in FIG. 10A. X-rays of control allograft recipients revealed severe infiltrates and complete opacification of the allograft indicative of severe rejection in FIG. 10B. Col(V)-fed allograft recipients show only mild infiltrates at two weeks post-transplantation in FIG. 10C. Chest x-rays representative of five rats in each group.
Figure 10B:
Figure 10A:

Diminished PMN and lymphocyte counts in allograft BAL fluid is usually associated with less severe radiographic and histologic lesions during acute lung allograft rejection. To determine the rate of progression of lung infiltrates, transplant recipients were monitored by serial chest radiographs on days 1, 6, and 13 post-transplantation and graded as described above. As shown in FIG. 10, control isografts did not have any pulmonary infiltrates at all monitored time points (grade 1) (FIG. 10A). In the control allografts serial x-rays revealed gradual development of mild infiltrates (grade 2) in the left lung at 6 days post-transplant (data not shown), which resulted in severe infiltrates and complete opacification of the allograft (grade 4) by the end of the second week (FIG. 10B). However in col(V)-fed allografts, the development of infiltrates was much slower compared to controls. The x-rays were normal (grade 1) at day 6 and only mild infiltrates (grade 2) were present at two weeks post-transplantation (FIG. 10C).

The upper panels of FIG. 11 show the gross anatomy of the native and isograft WKY lungs, and the native and allograft lungs from control allograft and col(V)-fed allograft rats harvested at two weeks post-transplantation. The isograft (left-L) and the native lung (right-R) were normal in appearance (FIG. 11A). The transplanted lung in control allograft recipients was dark brown in color and shrunken compared to the native lung (FIG. 11B). In contrast, the transplanted left lung in col(V)-fed allograft recipients (FIG. 11C) had the appearance of the native (normal) or isograft lung (FIG. 11A).

Fewer PMN's and lymphocytes in allograft BAL fluid, less severe infiltrates in the allografts on chest x-ray, and preserved gross anatomy suggested that feeding col(V) prior to transplantation down-regulated development of rejection pathology. The lower panels of FIG. 11 show the representative histology of control isografts, control allografts, and col(V)-fed allografts two weeks post-transplantation. All control isograft lungs had normal histology without signs of rejection (FIG. 11D). Control allografts revealed extensive perivascular, peribronchial, and alveolar mononuclear cell infiltrates consistent with severe acute rejection (FIG. 11E). In contrast, only mild to moderate perivascular and peribronchial infiltration were detected in the col(V)-fed allograft lungs (FIG. 11F).

Table 3 shows the grading of rejection pathology at two weeks post-transplantation. Acute rejection was graded A0-A4 according to the presence and extent of perivascular and interstitial mononuclear cell infiltrates, and B0-B4 according to the extent and intensity of the airway inflammation (Yousem et al. 1990). All control isograft lungs revealed normal histology of the lung (A 0±0, B 0±0). The control allografts had severe vascular and airway rejection (A 3.8±0.2, B 4.0±0, respectively). In contrast, col(V)-fed allografts showed mild to moderate vascular and airway rejection (A 2.8±0.2, B 2.6±0.2, respectively) (*p<0.028 for A scores and †p<0.009 for B scores compared to control allografts) (Table 3). Experiments showed that feeding col (II) or col(XI) had no effect on development of allograft pathology compared to control allografts (Table 3). These data show that feeding col(V) down-regulated acute rejection pathology.

Figure 12:
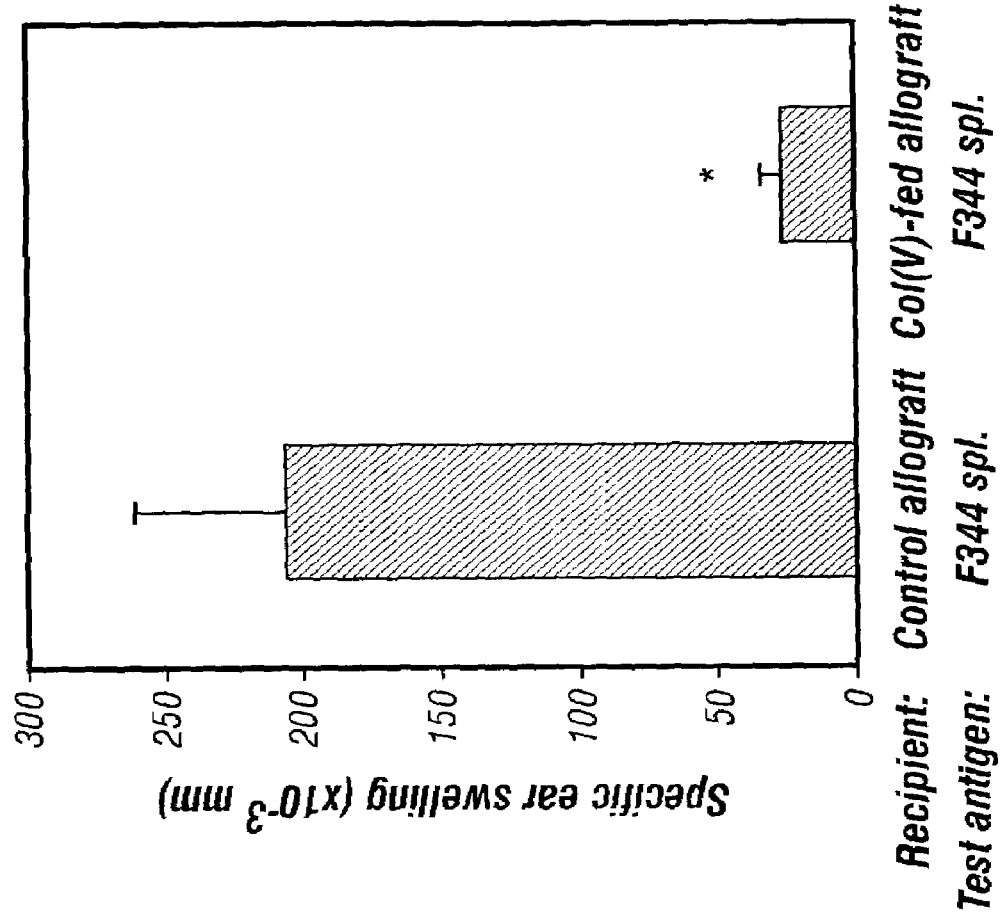
FIG. 12. Reduction of DTH responses to donor alloantigens by oral administration of col(V). Control allograft recipients and col(V)-fed allograft recipients two weeks post-transplantation were challenged in the right pinnae with $10^7$ irradiated (3000 rad) donor-derived F344 splenocytes, and diluent in the left pinnae. The ear thickness was measured with a micrometer caliper (Mitutoyo, Field tool Supply, Chicago, Ill.) in a blinded fashion immediately before and 24 hr after injection and the specific ear swelling calculated as described in Methods. Data represent the mean±SEM of specific ear swelling in mm×$10^{-3}$ of four rats in each group. (*$p<0.02$ compared to control allografts).

Data showing that feeding col(V) down-regulates lung allograft rejection suggested that orally tolerized lung allograft recipients should have diminished DTH responses to donor alloantigens. To determine if col(V) feeding diminished immune responses to alloantigens, control allograft recipients and col(V)-fed allograft recipients were challenged in the right pinnae with whole allogeneic F344 splenocytes and PBS in the left pinnae and DTH responses determined. As shown in FIG. 12 and previously shown in FIG. 8, untreated control allograft recipients had a strong DTH response after challenge with donor antigen. In contrast, compared to control allograft recipients, the DTH response to donor antigen was reduced significantly in col(V)-fed allograft recipients (*p<0.02) (FIG. 12).

The impaired immune response to alloantigen induced by col(V) could have been due to global immune hyporesponsiveness (Faria and Weiner 1999), and not immune tolerance. Therefore, to determine if col(V)-fed WKY rats could respond to other antigens, these rats received LPS either intratracheally (1 mg/kg) or intravenously (4 mg/kg) which are doses known to induce severe inflammatory reactions in the lung and systemically 24 hrs after challenge (O'Leary et al. 1997). The disease induced is analogous to pneumonia and sepsis caused by gram-negative bacteria. Similar to normal WKY rats, instillation of LPS into lungs or injected i.v. into col(V)-fed WKY rats induced severe illness (ruffled fur and prostration) and massive influx of PMN's and lymphocytes into the lung as observed in BAL differential cell counts and pathology (Data not shown).

Figure 19:
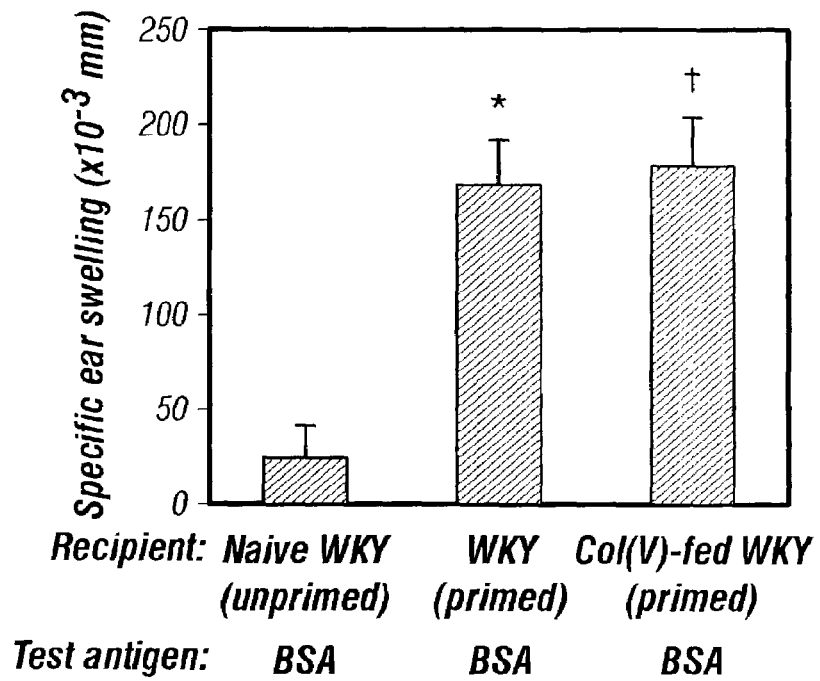
FIG. 19. DTH responses to BSA in naïve and col(V)-fed WKY rats. Naïve and col(V)-fed WKY rats were primed by s.c. injection of 100 μg of BSA in adjuvant and seven days later challenged with 2% heat aggregated BSA solution in the right pinnae and diluent in the left. The ear thickness was measured with a micrometer caliper in a blinded fashion immediately before and 24 h after injection and the spectific ear swelling calculated as described above. Unprimed WKY rats served as controls. Data represent the mean±SEM of specific ear swelling in mm×$10^{-3}$ of four rats in each group (*p<0.018 compared to unprimed naïve WKY rats and †p ? 0.05 compared to primed WKY rats.).

To investigate further if the impaired immune response induced by col(V) feeding was antigen-specific, we determined if feeding col(V) affected DTH responses to an unrelated nominal antigen, BSA, a T-lymphocyte-dependent antigen in rats (Henningsen et al. 1984). Naive and col(V)-fed WKY rats were primed by s.c. injection of 100 µg of BSA in adjuvant and seven days later challenged with 2% heat aggregated BSA solution in the right pinnae and diluent in the left. DTH responses were determined 24 h after injection. Unprimed WKY rats served as controls for these studies. As shown in FIG. 19, injection of BSA into the pinnae of unprimed rats did not induce significant ear swelling. In contrast, injecting BSA into unfed primed WKY rats induced significant ear swelling (*p<0.018 compared to unprimed naïve WKY rats) (FIG. 19). However col(V) feeding did not affect the DTH responses to BSA (†p>0.05 compared to primed WKY rats) (FIG. 19). Collectively, these data show that col(V)-induced suppression of lung allograft rejection is mediated by immune tolerance, and not global immune hyporesponsiveness.

Systemic production of TGF-β, IL-4, and IL-10 are cited frequently as cytokines responsible for suppressing immune responses in oral tolerance (Faria and Weiner 1999). Therefore, it was next determined if oral tolerance induced by col(V) is associated with up-regulated production of TGF-β, IL-4, and IL-10 during lung allograft rejection. Utilizing commercial ELISA's, TGF-β, IL-4, and IL-10 were quantitated in serum of the experimental groups. FIG. 17 shows the serum TGF-β levels in normal WKY rats, control allografts, and col(V)-fed allografts two weeks post-transplantation. As expected, low levels of TGF-β were present in the serum of normal WKY rats (Ying and Sanders 1998). There was a slight increase of TGF-β in control allografts. In contrast, TGF-β levels were up-regulated markedly in serum of col(V)-fed allografts (*p<0.05 compared to control allograft recipients) (FIG. 17). Neither IL-4 nor IL-10 was detectable in serum of the same rats (data not shown).

Figure 20:
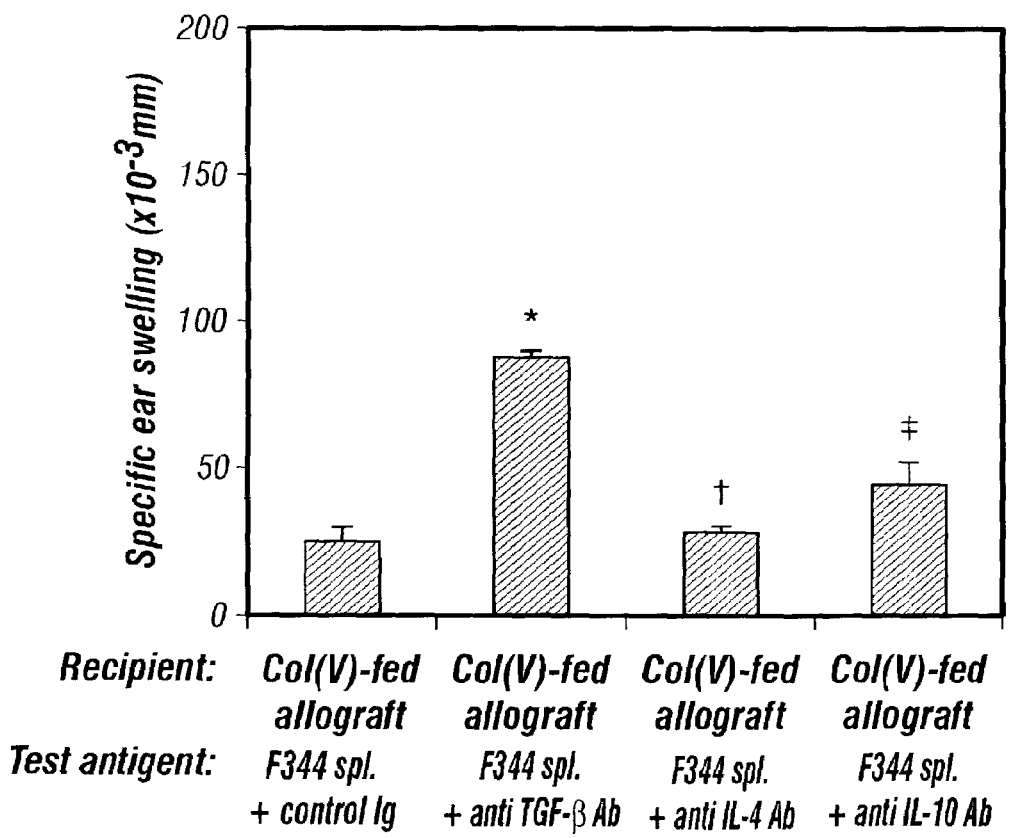
FIG. 20. Neutralization of TGF-β restores DTH responses to donor alloantigens in col(V)-fed allograft recipients. Col(V)-fed WKY rats were challenged in the right pinnae with $10^7$ irradiated (3000 rad) donor-derived F344 splenocytes mixed with either 5 μg of polyclonal anti-TGF-β Ab or anti-IL-4 or IL-10 Ab in PBS two weeks post-transplantation. The left pinnae received an equal volume of diluent plus splenocytes, and served as the control site. For negative controls, a separate group of col(V)-fed allografts received control immunoglobulins with splenocytes into the right pinnae and an equal volume of diluent plus splenocytes into the left pinnae. The ear thickness was measured with a micrometer caliper in a blinded fashion immediately before and 24 h after injection and the specific ear swelling calculated as described below. Spl, splenocytes. Data represent the mean±SEM of specific ear swelling in mm×$10^{-3}$ of four rats in each group [*p<0.03 and †, ‡p>0.05 compared to col(V)-fed allografts challenged with antigens mixed with control immunoglobulin.] The restoration of the dTH responses in col(V)-fed allografts with anti-TFG-β, anti-IL-4, and anti-IL-10 antibodies relative to control allografts was 75.7%, 24.3% and 39.9%, respectively.

Although IL-4 and IL-10 were not detected in the serum, this did not preclude their activity systemically in down-regulating cellular immune responses to donor alloantigens. To determine whether TGF-β, IL-4, or IL-10 had a role in suppression of immune responses to alloantigens, we utilized neutralizing antibodies to these cytokines in the DTH assay to donor antigens. Utilizing a modification of a procedure reported by Bickerstaff et al. (2000), two weeks post-lung transplantation, col(V)-fed WKY rats received $10^7$ irradiated (3000 rad) donor-derived F344 splenocytes mixed with 5 µg of polyclonal anti TGF-β, Ab or 5 µg of polyclonal anti IL-4 or IL-10 Ab in PBS into the right pinnae. The left pinnae received an equal volume of diluent plus splenocytes, and served as the control site. For negative controls, a separate group of col(V)-fed allografts received control immunoglobulins with splenocytes into the right pinnae and an equal volume of diluent plus splenocytes into the left pinnae. As shown in FIG. 20 and previously shown in FIG. 8 and FIG. 12, untreated control allograft recipients had a strong DTH response after challenge with donor antigen which was reduced significantly in col(V)-fed allograft recipients. However, col(V)-fed allografts significantly recovered DTH responses when anti-TGF-β antibodies were mixed with donor splenocytes and injected into the pinnae of the ears [*p<0.03 compared to col(V)-fed allografts challenged with antigens mixed with control immunoglobulin] (FIG. 20). In contrast, mixing donor splenocytes with neutralizing antibodies to IL-4 or IL-10 was less effective in restoring DTH responses to donor antigens [†,‡p>0.05 compared to col(V)-fed allografts challenged with antigens mixed with control immunoglobulin] (FIG. 20). The restoration of the DTH responses in col(V)-fed allografts with anti-TGF-β, anti-IL-4, and anti-IL-10 antibodies relative to control allografts was 75.7%, 24.3%, and 39.9%, respectively (FIG. 20).

Example 5

The Effect of Dose of Col(V) for Oral Tolerance on Development of Acute Lung Allograft Rejection a. Rat Lung Transplant Model F344 ($RT1^{1v1}$) and WKY ($RT1^1$) male rats (200-250 g) are purchased from Harlan Sprague Dawley (Indianapolis, Ind.). All left lung allografts (F344) or isografts (WKY) are transplanted orthotopically into WKY recipients as previously described (Yasufuku et al. Submitted; Sekine et al. 1997).

b. Isolation of Collagens

Type V collagen was isolated from either human placenta from normal births, or normal lung tissue specimens obtained at the time of lung cancer resection as reported (Mares et al. In Press). Gerald N. Smith Jr., Ph.D., with extensive expertise in collagen biochemistry (Smith et al. 1991; Smith et al. 1985), provided purified type V collagen for these studies.

C. Immunization Protocol

WKY rats are immunized with collagen prior to transplantation surgery using gastric gavage as reported in preliminary data and submitted manuscript. All rats are fed every other day for either 4 or 8 days as described in the table. Similar to preliminary data, after a one week recovery period post-feeding, the left lung of F344 rats (allografts) or WKY rats (isografts) is transplanted orthotopically into WKY recipients. No rats receive immunosuppression. Twenty rats are included in each feeding group for each collagen type.

| | Experimental Groups: | |
|---|---|---|
| Col(V)-fed Allograft (n = 20 for each dose and schedule) | Allograft- Control (n = 20) | Isograft (n = 20) |
| Donor: F344 rat lung (RT1$^{lv1}$) Recipient: WKY (RT1$^1$) rats - fed col(V) 10 µg, 20 µg, or 50 µg every other day for 4 or 8 days. | Donor: F344 rat lung (RT1$^{lv1}$) Recipient: WKY (RT1$^1$) rats - no feeding | Donor: WKY (RT1$^1$) rat lung Recipient: WKY (RT1$^1$) rats | d. Data Collection and Analysis

Twenty four hours prior to end of a two week period post-transplantation, which is the time for severe rejection to develop (Matsumura et al. 1995; Zuo et al. 1995), 10 recipient rats are tested for DTH responses to donor antigens, followed by harvesting thoracic organs. BAL is performed on the native and allograft lung by selectively cannulating the right and the left mainstem bronchi, respectively, and instilling a total of 5 ml of PBS at 37° C. (Yasufuku et al. Submitted; Sekine et al. 1997). Cell free BAL is obtained from centrifuged specimens and supernatants stored at −80° C. Blood is collected by vena cava and cardiac puncture, specimens centrifuged to separate serum, and stored at −80° C.

e. Delayed-Type Hypersensitivity (DTH) Responses

DTH studies are performed by injection of irradiated donor (F344) splenocytes into the right ear of WKY rats 24 hr prior to completion of the two week post-operative period as reported in preliminary data and manuscript (Yasufuku et al. Submitted). Data is reported as "specific ear swelling". Preliminary studies have confirmed other reports showing that the maximal DTH response occur 24 hour after ear injection (Sayegh et al. 1992b; Yoshino et al. 1995; Yamagami et al. 1999), and, therefore, all DTH measurements will be performed 24 h post-ear injection. Preliminary studies confirmed that DTH testing has no effect on systemic cellular or humoral responses. By comparing the DTH responses to donor antigens in isograft and allograft control recipients compared to collagen-fed WKY rats, it can be determined if different doses of col(V) have differential effects on DTH response to donor antigens.

f. Histologic Studies

After euthanasia, the thoracic organs are removed en bloc and fixed by intratracheal instillation of 4% glutaraldehyde, embedded in paraffin, sectioned at 5-7 µm, and stained with hematoxylin and eosin (H&E) for histologic studies by light microscopy. The histologic lesions are graded by standard histologic criteria for human lung allograft rejection (Yousem et al. 1996) in a blinded manner by Dr. Cummings (Yasufuku et al. Submitted; Sekine et al. 1997; Mares et al. In Press; Wilkes et al. 1998; Wilkes et al. 1995). Acute rejection is characterized by varying intensity of perivascular and peribronchiolar mononuclear cells infiltrates (Yousem et al. 1996). Since differences in cellular infiltrates between groups may be more subtle than accounted for in the accepted criteria of acute rejection, infiltrates will also be quantified by counting the perivascular and peribronchiolar mononuclear cells present on digitized H&E-stained tissue sections (cells/µm$^2$) utilizing Sigma Scan software (Jandel Scientific, Chicago, Ill.). The digitizing procedures are currently in use in our laboratories.

g. Determination of Cellular Cytotoxicity

Cytotoxic T-lymphocytes have key roles in the pathogenesis of lung allograft rejection (Trulock 1997), and impaired cellular cytotoxicity has been shown to be a key mechanism by which oral tolerance prevents disease activity (Faria and Weiner 1999; Mayer 2000; Garside and Mowat 1997). To determine whether diminished rejection activity in col(V) tolerized lung allograft recipients is associated with impaired anti-donor cellular cytotoxicity, peripheral lymph node cells are isolated from normal F344 (donor) rats, loaded with $^{51}$Cr (New England Nuclear, Boston, Mass.), and placed in 96 well flat bottom plates (target cells, 5×10$^3$/well) in complete media. Effector cells (splenic T-lymphocytes from recipient-WKY rats in each group) are incubated in varying ratios with targets (E/T ratios of 1:1, 5:1, 10:1. and 100:1) at 37° C. for 4 hours. Pure splenic T-cells (>95% pure) are isolated utilizing anti-CD3 magnetic beads (Dynal Corp, Lake Success, N.Y.), and confirmed by flow cytometry. Cytotoxicity is determined by specific $^{51}$Cr release induced by effector cells in each E/T ratio compared to release from loaded target cells, alone.

h. Detection of Apoptosis

Other investigators have confirmed that lung allograft rejection in rats and humans is associated with apoptosis in cells present in alveolar, vascular, and bronchiolar tissues, and that apoptosis is detected infrequently during allograft acceptance (Trulock 1997; Mares et al. In Press; Blankenberg et al. 2000). The present inventor has previously shown that the local immune response to alloantigens includes induction of apoptosis in vascular endothelium and bronchiolar epithelium in mice. In addition, immunization with col(V), which induces anergy to donor antigens, prevents alloantigen-induced apoptosis in this model (Mares et al. In Press).

To determine the ability of col(V)-induced oral tolerance to prevent apoptosis in lung allografts, TdT-mediated dUTP Nick End Labeling (TUNEL) assay kits (In Situ Cell Death Detection Kit, Boehringer Mannheim, Indianapolis, Ind.) are utilized to detect apoptosis in lung allograft tissue sections two weeks post transplantation. The quantity of apoptotic cells in perivascular and peribronchiolar tissues is quantitated on digitized eosin-counterstained tissue sections using (cells/µm$^2$) utilizing Sigma Scan software (Jandel Scientific, Chicago, Ill.).

i. Cytokine Profiles in Serum, Spleen, and Peripheral Lymph Nodes

To determine production of IL-4, IL-10, TGF-β, CTGF, and nitric oxide, all potential mediators of immune suppression induced by col(V), as well as time course of synthesis post-transplant, the dose of col(V) that is most effective in preventing rejection pathology is used to feed another group of rats. In brief, allograft control rats and col(V)-fed allograft recipients are sacrificed 2, 4, 6, 8, 10, 12, and 14 days post-transplantation, and serum levels of IL-4, IL-10, TGF-β quantitated by ELISA (R&D Systems, Minneapolis, Minn.) per manufacturer's protocol (n=5 five rats at each time point). RNase protections assays (Pharmingen, San Diego, Calif.)) are utilized to detect mRNA for these cytokines in peripheral lymph nodes and splenocytes. Controls are serum, lymph nodes and splenocytes from normal WKY rats.

CTGF levels in serum of control allografts, col(V) fed allografts, and normal rats are determined by ELISA by Dr. George Martin, Ph.D., Scientific Director of Fibrogen, San Francisco, Calif., the leading expert in the structure and function of CTFG. Northern blotting is utilized to detect mRNA for CTGF in peripheral lymph nodes, and spleen utilizing probes supplied by Dr. Martin. Protein and mRNA expression is assayed for at the same time points described for IL-4, IL-10, and TGF-β.

Nitric oxide levels in serum are detected at various time points described above in control allografts and col(V)-fed allografts at the various time points post-transplantation described above, as well as in normal WKY rats. Production of stable metabolic nitrites and nitrates in serum is determined by Greiss reaction utilizing spectrophotometric analysis of serum (Kallio et al. 1997).

Example 6

The Effect of Dose of Col(V) for Oral Tolerance on Development of Chronic Lung Allograft Rejection (Bronchiolitis Obliterans)

a. Animals

Pathogen-free, MHC (RT1)-incompatible male rats were utilized for the study: Fischer 344 (F344, $RT1^{1v1}$), Brown Norway (BN, $RT1^n$) and Wistar Kyoto (WKY, $RT1^1$) rats (250-300 g at the time of transplantation). All rats were purchased from Harlan Sprague Dawley (Indianapolis, Ind.) and housed in the Laboratory Animal Resource Center at Indiana University School of Medicine (Indianapolis, Ind.) in accordance with institutional guidelines.

b. Preparation of Collagens

Collagen type II [col(II)] was isolated from canine cartilage as previously reported. Purified human type V collagen [col(V)] and type XI collagen [col(XI)] was a gift from Dr. Jerome Seyer (VA Hospital, Hampton, Va.). Collagens were diluted in 0.005M acetic acid (0.5 mg/ml) and stored at 4° C. until use.

c. Oral Administration of Collagen

WKY rats were fed with 10 μg of col(V) dissolved in 0.5 ml of saline by a gastric gavage utilizing a 16-gauge ball-point stainless steel animal feeding needle (Braintree Scientific, Braintree, Mass.) as previously reported. Control animals were fed with diluent alone. Animals were fed every other day for eight feedings. Seven days after the last feeding, these rats were utilized as recipients of lung allografts.

d. Transplantation Model

The orthotopic transplantation of left lung isografts (WKY→WKY), or allografts (F344→WKY) was performed as previously reported, utilizing a procedure initially described by Marck et al. (1983), and Prop et al. (1985). The F344→WKY transplant model is associated with the development of severe acute rejection by the end of the second week. In addition, this model is the only animal model of lung transplantation that develops bronchiolitis obliterans (BO) reproducibly. Survival exceeded 90% in all transplantation groups. No immunosuppressive therapy was given at any time during the experimental period.

Three transplantation groups were studied: lungs from WKY rats transplanted into WKY recipients [control isografts]; F344 lungs transplanted into diluent fed WKY recipients [control allografts]; and F344 lungs transplanted into col(V)-fed WKY recipients [col(V)-fed allografts]. Recipients were sacrificed at two and 10 weeks post-transplantation.

e. Delayed-Type Hypersensitivity Response

DTH responses were determined as above, by a modification of a procedure initially described by Sayegh et al. (1994), and Yamagami et al. (1999). In brief, 10 weeks post-lung transplantation, control or col(V)-fed WKY rats received $10^7$ irradiated (3000 rad) donor-derived F344 or third party (BN) splenocytes in 30 μl of PBS into the right pinnae by s.c. injection using a 26 gauge needle. The left pinnae received an equal volume of diluent, and served as the control site. Naïve WKY rats were negative controls. A separate group of naïve or allograft recipient WKY rats were tested with 15 μg of col(II), col(V), or col(XI) in 30 μl volume injected into the right pinnae and diluent into the left. The ear thickness was measured with a micrometer caliper (Mitutoyo, Field Tool Supply, Chicago, Ill.) in a blinded fashion immediately before and 24 h after injection. The specific ear swelling was calculated according to the following formula: Specific Ear Swelling=(right ear thickness @ 24 h–right ear thickness @ 0 h)–(left ear thickness @ 24 h–left ear thickness @ 0 h)×$10^{-3}$ mm. All data reported as the mean of triplicate measurements.

f. Neutralization of TGF-β in DTH

Neutralization of TGF-β at the DTH site was performed as previously reported by a modification of a procedure described by Bickerstaff et al. (2000). In brief, 10 weeks post-lung transplantation, col(V)-fed WKY rats received $10^7$ irradiated (3000 rad) donor-derived F344 splenocytes mixed with 5 μg of polyclonal chicken anti rat TGF-β Ab (R&D Systems, Minneapolis, Minn.) in 30 μl of PBS into the right pinnae. The left pinnae received an equal volume of diluent, and served as the control site. For negative controls, a separate group of col(V)-fed allografts received $10^7$ irradiated (3000 rad) donor-derived F344 splenocytes mixed with 5 μg of control chicken immunoglobulins or control goat immunoglobulins (R&D Systems, Minneapolis, Minn.) into the right pinnae and diluent into the left. The Specific Ear Swelling was determined as described above. Control immunoglobulins had no effect on the DTH response.

g. Mixed Leukocyte Reaction

Mixed leukocyte reaction was performed by a modification of a procedure described previously. In brief, F344 splenocytes (stimulators) which were used as a source of antigen-presenting cells (APCs), were treated with mitomycin C (Sigma, St. Louis, Mo.) and cocultured in varying ratios with lymph node T lymphocytes (responders) from WKY rats ($3\times10^5$/well) in 200 μl of medium (RPMI, 2 mM L-Glutamine, $5\times10^{-5}$ M 2-mercaptoethanol, 100 U/ml penicillin, 100 μl/ml streptomycin, 10% heat-inactivated fetal calf serum) in 96-well, flat-bottom microtiter plates (Costar, Cambridge, Mass.). Eighteen hours before the completion of a 5 day incubation at 37° C. (5% $CO_2$), 1 μCi/ml of $^3H$ (Amersham Corp., Arlington Heights, Ill.) was added to each well. Cultures were harvested with an automated cell harvester (Brandel, Gaithersburg, Md.) and analyzed in a liquid scintillation counter (Beckman, Arlington Heights, Ill.). Cellular proliferation was determined as the mean of counts per minute of [$^3H$] thymidine incorporation in triplicate cultures and reported as stimulation index. In separate experiments the same assay was performed using splenocytes from WKY rats of the experimental group as the stimulator and lymph node T lymphocytes from F344 rats as responders.

h. Quantitation of Cytokines

TGF-β levels in serum of the experimental groups were quantitated by ELISA utilizing the TGF-$β_1$ immunoassay system (Promega, Madison, Wis.) per manufacture's protocol. IL-4 and IL-10 levels in serum were quantitated by ELISA utilizing Cytoscreen immunoassay kits (BioSource International, Camarillo, Calif.) per manufacture's protocol. The sensitivity of the TGF-β, IL-4, and IL-10 assays were 32, 2, and 5 pg/ml, respectively.

i. Pathological Grading

Native and transplanted lungs from each group were harvested, fixed, sectioned, stained, and graded for rejection pathology using standard criteria by a pathologist (O.W.C.) in a blinded fashion without prior knowledge of the transplantation group as previously reported.

j. Statistics

Since data for DTH in control allograft and naïve WKY rats challenged with different antigens was found to be non-normally distributed, a rank-sum two way ANOVA with interaction was utilized to determine differences amongst groups. Differences in DTH responses to donor alloantigens between control allografts and col(V)-fed allografts were determined utilizing a Mann-Whitney U test. The Student's t test for multiple comparison was utilized for analysis of MLR and cytokines. P values<0.05 were determined to be significant.

k. Results

Figure 21:
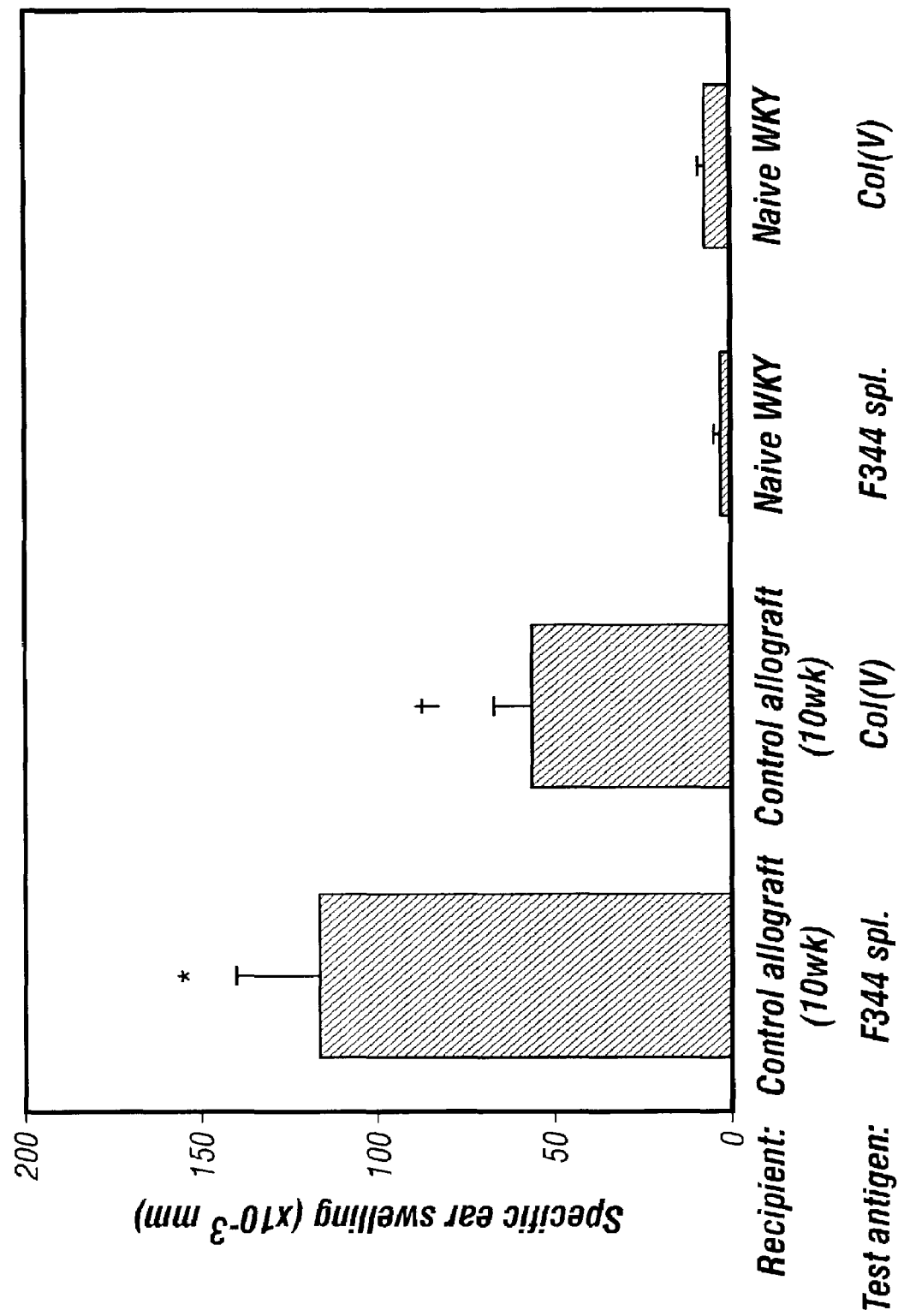
FIG. 21. DTH responses to donor alloantigens, col(II), col(V), col(XI), and third party alloantigens in control allograft recipients ten weeks post-transplantation. Animals received $10^7$ irradiated (3000 rad) donor-derived F344 splenocytes, third party (BN) splenocytes, or 15 μg of col(II), col(V), or col(XI) into the right pinnae and diluent into the left pinnae. The ear thickness was measured with a micrometer caliper in a blinded fashion immediately before and 24 h after injection. The specific ear swelling was calculated as described below. Spl, splenocytes. Data represent the mean±SEM of specific ear swelling in mm×$10^{-3}$ of three rats in each group [*p<0.05 compared to naïve WKY rats challenged with F344 splenocytes or col(V)].

The present inventor has shown that acute lung allograft rejection is associated with immune response to donor antigens as well as col(V). However, recent studies have suggested that immune responses to donor antigens may diminish over time. To determine if immune response to donor antigens and col(V) are present long term after lung transplantation, DTH responses to F344 (donor) splenocytes and col(V) were examined in WKY rats 10 weeks after transplantation of F344 lung allografts. FIG. 21 shows that control allograft recipients have significant DTH responses to donor antigens (F344 splenocytes) and col(V) compared to naïve WKY rats (*p<0.05). Significantly, the DTH responses to donor antigen and col(V) at 10 weeks was similar to that observed during acute rejection (two weeks post transplantation). Col(II) or col(XI) (controls) did not induce DTH responses in lung allograft recipients at either time point.

Figure 22:
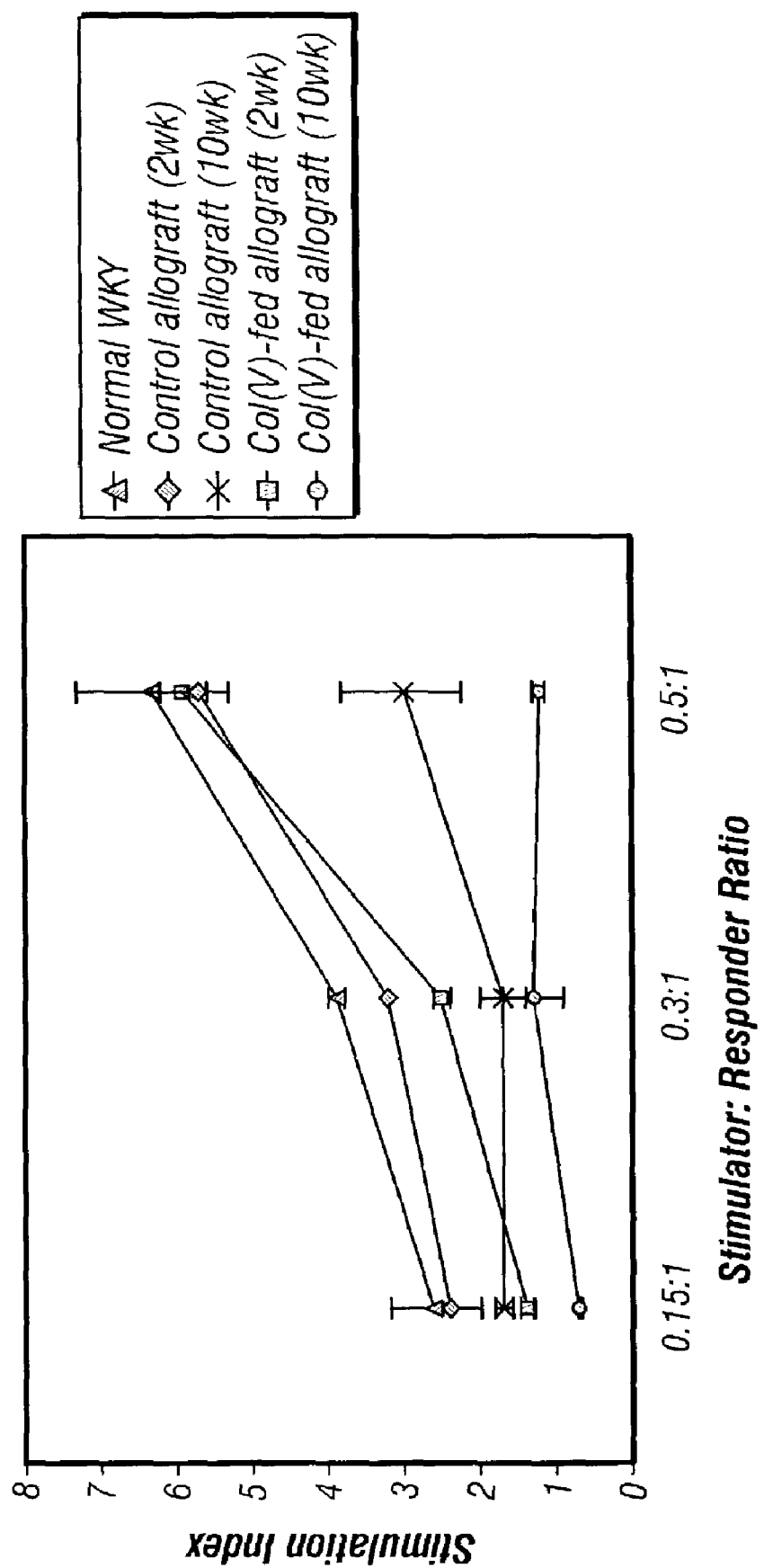
FIG. 22. Mixed leukocyte reaction. Varying ratios of mitomycin-C-treated F344 splenocytes (stimulators) were incubated with $3 \times 10^5$ lymph node T-lymphocytes (responders) from WKY rats (Normal), or WKY rats that were fed col(V). Eighteen hours prior to the completion of a 5 day incubation, the cells were pulsed with $^3$H and proliferation determined by counts/minute (cpm) of thymidine incorporation. Stimulation index equals the multiples of proliferation in lymph node lymphocytes induced by varying quantity of stimulator cells relative to proliferation of lymph node lymphocytes alone. Data representative of three experiments.
Figure 23:
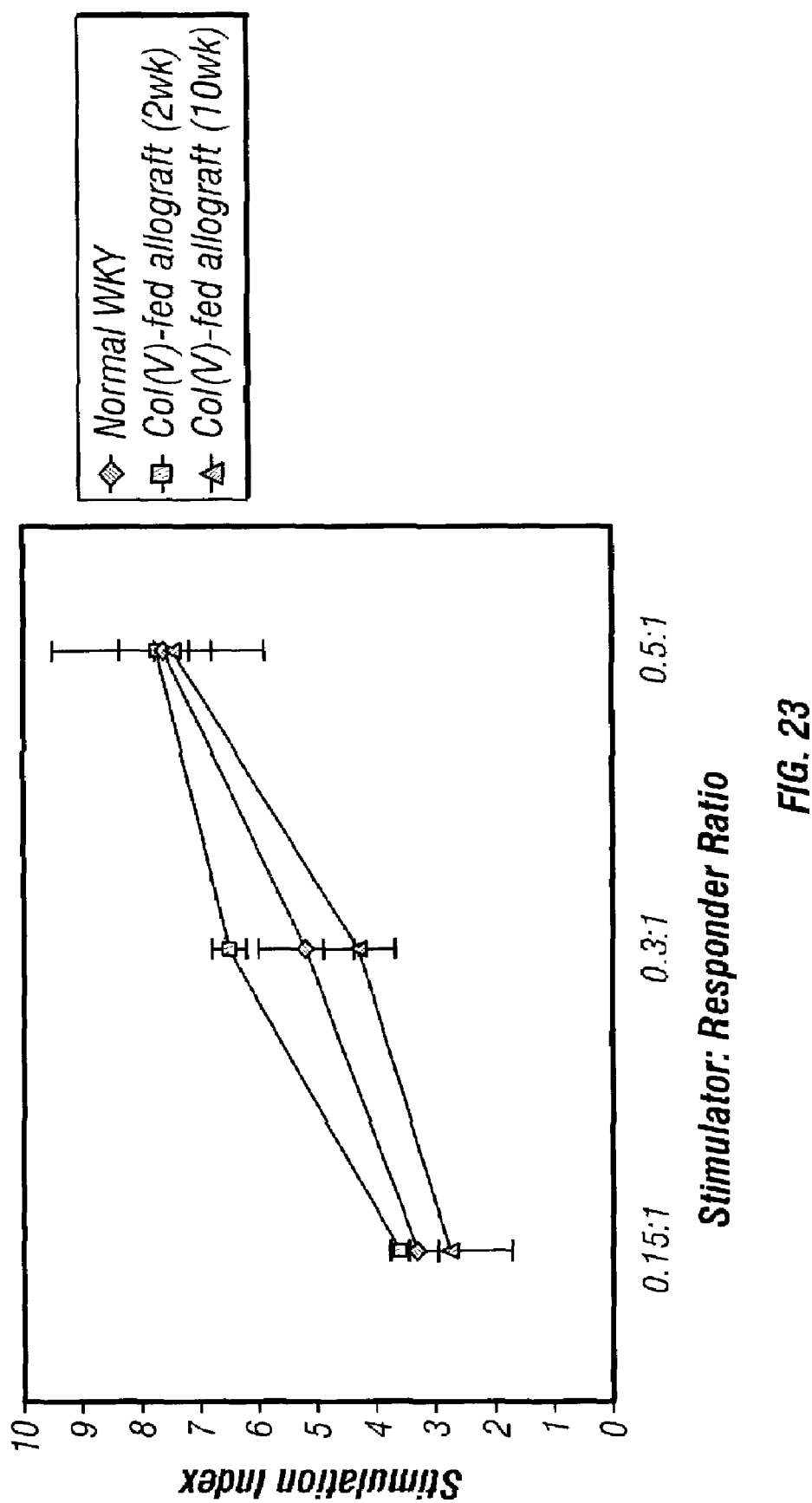
FIG. 23. Mixed leukocyte reaction. Mitomycin-C-treated normal WKY rat splenocytes or col(V)-fed allograft recipient rat splenocytes (stimulators) were incubated with $3 \times 10^5$ normal F344 rat lymph node T-lymphocytes (responders) at varying ratios. Eighteen hours prior to the completion of a 5-day incubation, the cells were pulsed with $^3$H-thymidine and proliferation determined by counts/minute (cpm) of thymidine incorporation in triplicate cultures. Stimulation index equals the multiples of proliferation in lymph node lymphocytes at varying stimulator:responder ratios relative to proliferation of lymph node lymphocytes alone. Data represent mean±SEM of three experiments (*p<0.05 compared to control).

Oral tolerance induction using donor derived antigen has been effective in suppressing cellular immune responses to donor antigens up to two weeks post-transplantation. In addition, deficient antigen presentation has been reported to be another mechanism by which tolerance can modulate immune responses. It was next determined if feeding col(V) down regulated cellular immune responses to donor antigens long term, and examined the effect of col(V)-induced oral tolerance affected antigen presentation. As described above, unfed and WKY rats that were fed col(V) received F344 lung allografts. Two weeks (time of acute rejection) and ten weeks (time of onset of BO) post-transplantation, rats were sacrificed, lymph node lymphocytes isolated and stimulated with donor antigens (F344 splenocytes). FIG. 21 shows that lymph node lymphocytes from normal WKY rats or lymphocytes isolated from WKY rats two or ten weeks post-transplantation of F344 lung allografts had comparable proliferative responses to donor antigens. In contrast, compared to normals or control allografts, col(V)-induced oral tolerance caused significant reductions in proliferative responses to donor antigens at both time points (* p<0.05). In addition, proliferative responses to lymphocytes from col(V)-fed lung allograft recipients were less at 10 weeks compared to two weeks (*p<0.05, FIG. 22).

We next determined if col(V)-induced oral tolerance affected antigen presentation. In brief, splenocytes (source of antigen presenting cells) were isolated from normal WKY rats, or col(V)-fed WKY rats two and 10 weeks post-transplantation of F344 lung allografts, and examined for their ability to induce F344 lymph node lymphocytes to proliferate in a MLR. FIG. 21 shows that splenocytes isolated from col(V)-fed allograft recipients at two and ten weeks induced proliferation comparable to splenocytes isolated from normal WKY rats.

Figure 24A:
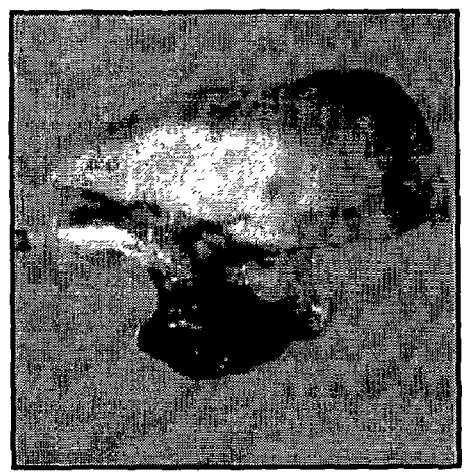
FIG. 24A, FIG. 24B, FIG. 24C, and FIG. 24D. Upper panel: Gross anatomy of control allograft lungs FIG. 24A, and col(V)-fed allograft lungs FIG. 24B ten weeks post-transplantation. The left (L) lung is the transplanted lung and the right Ⓡ is the native lung in each panel. The control allograft lung was dark brown in color, shrunken, and of firm consistency compared to the native lung. However, the col(V)-fed allograft lung had a nearly normal appearance with only slight discoloration. Lower panel: Histology of control allografts FIG. 24C and col(V)-fed allografts FIG. 24D ten weeks post-transplantation. Control allografts developed extensive interstitial nomonuclear cell infiltrates, fibrosis, and obliteration of small airways by granulation tissue which are pathologic lesions of BO. In contrast, col(V)-fed allografts only had mild alveolar infiltrates, without interstitial inflammation which describes the pathology of mild acute rejection (grade A2). Photomicrographs representative of five rats in each group.
Figure 24B:
Figure 24C:
Figure 24D:
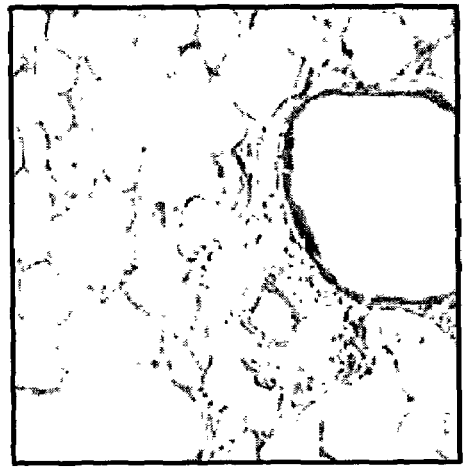

DTH responses to donor antigens have been reported to correlate with rejection activity in various rodent models of organ transplantation. Therefore, data showing diminished DTH responses to donor antigens in col(V)-fed lung allograft recipients at ten weeks suggested reduced rejection pathology in the allografts. FIG. 24 shows the gross anatomy and histology of lung allografts harvested from WKY rats that received F344 lung allografts (control allografts), and col(V)-fed WKY rats that received F344 lung allografts 10 weeks post-transplantation. Control allografts were dark brown, shrunken, and firm (FIG. 24A). In contrast, allografts from col(V)-fed WKY rats had a nearly normal appearance with only slight discoloration (FIG. 24B). At 10 weeks post-transplantation, all control allografts developed extensive interstitial mononuclear cell infiltrates, fibrosis, and obliteration of small airways by granulation tissue which are pathologic lesions of BO (n=5, FIG. 24C). In contrast, allografts harvested from col(V)-fed rats only had mild alveolar infiltrates, without interstitial inflammation which describes the pathology of mild acute rejection (grade A2, n=5, FIG. 24D).

Figure 25:
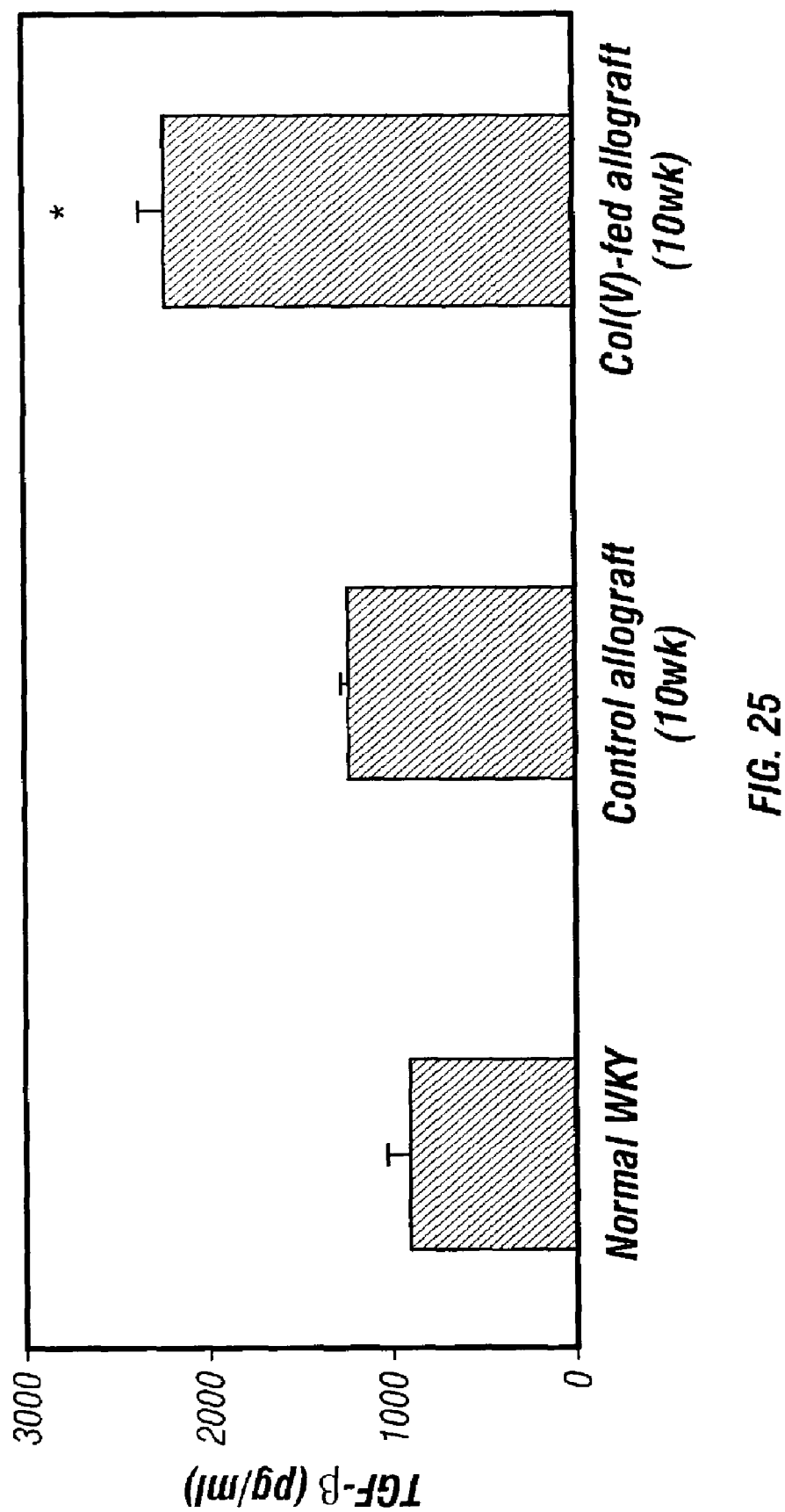
FIG. 25. TFG-β levels in serum of normal WKY rats, control allograft recipients, and col(V)-fed allograft recipients ten weeks after transplantation. Levels of TFG-β in serum were determined by ELISA. Data represent mean±SEM of three rats in each group. (*p<0.05 compared to control allografts).

Systemic production of IL-4, IL-10, or TGF-β has been reported commonly as the mechanism of oral tolerance-induced immune suppression. Serum levels of TGF-β in the three experimental groups 10 weeks after transplantation are shown in FIG. 25. Normal WKY rats have low levels of TGF-β in serum, and a slight, but not significant, increased TGF-β levels in WKY rats that received F344 lung allografts (control allografts—FIG. 25). However, feeding col(V) prior to lung transplantation resulted in significantly increased serum levels of TGF-β (FIG. 25, *p<0.05). Feeding col(V), alone, without lung transplantation did not increase serum TGF-β levels (data not shown). Neither IL-4 nor IL-10 was detected in serum of any group.

Figure 26:
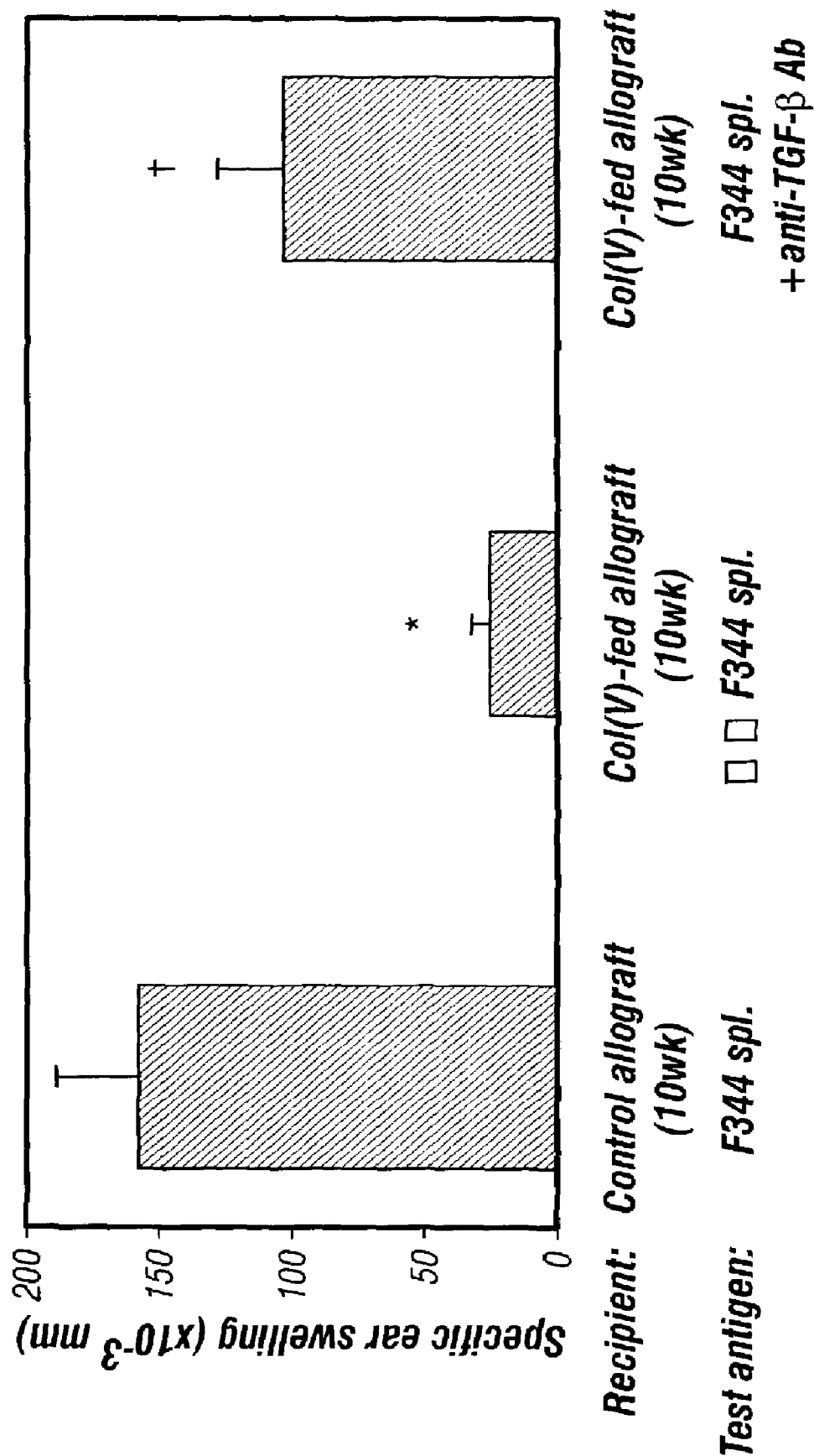
FIG. 26. Neutralization of TGF-β in DTH Response. Col(V)-fed WKY rats received $10^7$ irradiated (3000 rad) donor-derived F344 splenocytes mixed with 5 μg of polyclonal chicken anti-rat TFG-β Ab in to the right pinnae and diluent into the left pinnae. For negative controls, a separate group of col(V)-fed allografts received $10^7$ irradiated (3000 rad) donor-derived F344 splenocytes mixed with 5 μg of control chicken immunoglobulins or control goat immunoglobulins into the right pinnae and diluent into the left. The Specific Ear Swelling was determined as described.

Data showing down-regulation of lymphocyte responses to alloantigen and intact presentation of alloantigens in vitro, suggests that col(V)-induced oral tolerance should also be associated with suppressed DTH responses to donor antigens in vivo. As expected, FIG. 26 shows that control allograft recipients have strong DTH responses to donor antigens. However, feeding col(V) prior to transplantation results in significantly diminished DTH responses to donor antigens (FIG. 26, *p<0.05). To determine if increased serum levels of TGF-β was contributing to col(V)-induced oral tolerance, the DTH response to donor antigens was repeated using neutralizing antibodies to TGF-β as reported previously. FIG. 26 shows that neutralizing TGF-β resulted in a significant recovery of DTH responses to donor antigens (*p<0.05, and 75% of DTH response observed in control allografts).

Example 7

The Determination of Whether Oral Tolerance Induced by Col(V) is MHC Restricted
Experimental Groups:

| Col(V)-fed Allograft (n = 10) | RT1 (MHC) | Allograft Control - (not fed) (n = 10) | Days to Severe Rejection in Allograft-Control |
|---|---|---|---|
| Donor: BN Recipient: LEW | $RT1^l$ $RT1^1$ | Donor: BN Recipient: LEW | 7 |
| Donor: F344 Recipient: LEW | $RT1^{lv1}$ $RT1^1$ | Donor: F344 Recipient: LEW | 14 |
| Donor: PVG Recipient: ACI | $RT1^c$ $RT1^a$ | Donor: PVG Recipient: ACI | 10 | a. Description of Rats

All rats are male, 200-250 gram, and purchased Harlan Sprague Dawley (Indianapolis, Ind.) and donor recipient pairs are MHC (RT1) incompatible. The time for the development of severe rejection has been established for each rat strain combination (Wildevuur and Nieuwenhuis 1985). All allografts (left lung of the donor) are transplanted orthotopically into recipients as described for the F344→WKY transplant model (Yasufuku et al. Submitted).

b. Immunization Protocol

Studies performed in Example 5, above determine the optimal dose and feeding schedule of col(V) to induce tolerance, and that dose and schedule is used to feed recipient rats in this Example. Similar to preliminary data, immunized rats have a one-week recovery period between the completion of immunization and transplantation. No rats receive immunosuppression.

c. Data Collection and Analysis.

Twenty four hours prior to end of the post-transplant period, which is the time for severe rejection to develop in each group (Wildevuur and Nieuwenhuis 1985), recipient rats are tested for DTH responses to donor antigens, followed by harvesting thoracic organs.

d. Delayed-Type Hypersensitivity (DTH) Responses

DTH responses to donor splenocytes are performed for each rat stain pair as described in preliminary data using appropriate donor splenocytes as the source of antigen.

e. Histologic Studies

After euthanasia, the thoracic organs are removed en bloc and examined for rejection pathology as described (Sekine et al. 1997).

By comparing the DTH responses to donor antigens in allograft control recipients compared to collagen-fed recipients, and pathologic lesions in allograft controls compared to collagen-fed recipients, whether col(V)-induced oral tolerance is non-MHC-restricted is determined.

Example 8

The Determination of Whether Oral Tolerance Induction Prevents Onset of Bronchiolitis Obliterans, and Down-Regulates Established Acute Rejection
Experimental Groups:

| Group A: To evaluate prevention of bronchiolitis obliterans | |
|---|---|
| Col(V)-fed Allograft (n = 20) | Allograft Control (n = 20) |
| Donor: F344 ($RT1^{lv1}$) Recipient: WKY ($RT1^1$) fed col(V) | Donor: F344 ($RT1^{lv1}$) Recipient: WKY ($RT1^1$), no feeding |

| Group B: To evaluate prevention of established rejection | |
|---|---|
| Col(V)-fed Allograft (n = 10 recipients at each time point) | Allograft Control |
| Donor: F344 ($RT1^{lv1}$) Recipient: WKY ($RT1^1$) fed col(V) starting day 1 post-op, or week 2, 6, 8, or 10 post transplantation | Donor: F344 ($RT1^{lv1}$) Recipient: WKY ($RT1^1$) (n = 50), no feeding | a. Description of Rats and Transplant Model

The donor (F344) and recipient (WKY) rats are identical to those described in Example 5. All allografts (left lung of the donor) are transplanted orthotopically into recipients as previously described. No rats receive immunosuppression.

b. Immunization Protocol

WKY rats in Group "A" are fed col(V) in a dose and schedule determined optimal to prevent acute rejection in the prior section. No WKY rats in Group "B" receive col(V) prior to transplantation. The present inventor has confirmed that moderate to severe acute rejection occurs by the end of the $2^{nd}$ week, severe acute rejection is established by the $4^{th}$ week, which progresses to bronchiolitis obliterans (chronic rejection) at approximately the $14^{th}$ week (about 100 days) post transplantation (Hirt et al. 1999). At each time point post transplant in Group "B", one group of 10 WKY rats is fed col(V) by gastric gavage using the regimen determined to prevent rejection episodes. Allograft control animals are not be fed col(V).

Data Collection and Analysis

Group A: Fourteen weeks post-transplantation, to time to onset of bronchiolitis obliterans, thoracic organs are harvested from col(V)-fed and allograft control rats as described above. Group B: Two weeks after the completion of each feeding regimen, thoracic organs from col(V)-fed WKY rats are harvested. Therefore, thoracic organs from col(V)-fed WKY rats in Group "B" are harvested at approximately 4, 6, 10, 12, and 14 weeks post transplantation, and are paired with thoracic organs harvested at the same time points in allograft control animals.

c. Histologic Studies

After euthanasia, the thoracic organs are harvested, fixed, sectioned, stained, and histologic lesions graded by standard histologic criteria for human lung allograft rejection as described in Example 5. Pathologic lesions in allografts of col(V)-fed recipients in Group "A" are compared to histology of allograft control lungs which will have developed bronchiolitis obliterans. The pathologic lesions in allografts from col(V)-fed WKY rats in Group "B" are compared to the pathologic lesions in allograft controls harvested at the same time points.

Interpretation

In addition to establishing the ability of col(V) to induce oral tolerance to lung allografts, these studies determine the dose response of the tolerizing effects of col(V), MHC restriction of this process, and the ability of col(V) to down-regulate established acute rejection and BO. These studies also determine whether oral tolerance down-regulates the cellular immunity of acute lung allograft rejection.

Oral tolerance induction by col(V) at all doses may only partially prevent the onset of the rejection responses or partially down-regulate established acute and chronic rejection. Typically, high doses of potent immunosuppressive agents, such as cyclosporine, are effective in suppressing lung allograft rejection in rats (Marck et al. 1983). However, no immunosuppressive drugs are used. If feeding col(V) at all doses only partially, and not completely, prevents rejection responses then it may be due to less than optimal tolerance induction. Therefore, to determine if rejection responses could be completely abrogated, these studies will be repeated by treating col(V)-tolerized animals with low doses of cyclosporine prior to lung transplantation.

Example 9 cytes in spleen and lymph nodes is determined by analysis of cell populations by flow cytometry. These antibodies have been reported to deplete up to 80% of CD8+ or CD4+ T-lymphocytes beginning seven days post-injection and persisting for 10 to 14 days (Barone et al. 1995; Sedgwick 1988; Huang et al. 1999; Sayegh et al. 1989; Hoffmann et al. 1997). Since the experimental period lasts beyond the length of cell depletion induced by the antibodies (total length about 30 days including immunization with col(V) and lung transplantation), animals receive injections of each or both antibodies at the appropriate intervals after the initial injections to maintain cell depletion. Controls for the injection experiments are WKY rats that receive injections of PBS or isotype/species matched control antibodies (Accurate Chemical, Westbury, N.Y.; and Pharmingen). Repeated injections of murine antibodies into rats could potentially induce anti-murine antibody production in vivo, and, therefore, inactivate the anti-T-lymphocyte antibodies. However, studies using these antibodies for repeated injection, for the time periods proposed and at similar doses, have shown that anti-murine antibodies do not develop as a result of repeated injections (Sayegh et al. 1989).

The Determination of the Requirement for CD4+ and CD8+ T-lymphocytes in the Induction of Oral Tolerance by Col(V)
Experimental Groups:

| Allograft Control (n = 10) no feeding | Collagen(V)-fed (n = 10) | Collagen(V)-fed CD4 depleted (n = 10) | Collagen(V)-fed CD8 depleted (n = 10) | Collagen(V)-fed, control antibody treated (n = 10) |
|---|---|---|---|---|
| Donor: F344 rat lung ($RT1^{lv1}$) Recipient: WKY ($RT1^l$) rats | Donor: F344 rat lung ($RT1^{lv1}$) Recipient: WKY ($RT1^l$) rats - fed col(V) | Donor: F344 rat lung ($RT1^{lv1}$) Recipient: CD4-depleted WKY ($RT1^l$) rats - fed col(V) | Donor: F344 rat lung ($RT1^{lv1}$) Recipient: CD8-depleted WKY ($RT1^l$) rats - fed col(V) | Donor: F344 rat lung ($RT1^{lv1}$) Recipient: control antibody-treated WKY ($RT1^l$) rats - fed col(V) | a. Description of Rats and Transplant Model

The donor (F344) and recipient (WKY) rats are identical to those described in Example 5. No immunosuppression is used.

b. Depletion of CD4+ and CD8+ T-lymphocytes

Mouse anti-rat CD8 antibodies (OX-8 antibodies) will be obtained from an OX-8 hybridoma cell line (American Type Culture Collection-ATCC, Rockville, Md.) (Barone et al 1995; Sedgwick 1988; Huang et al. 1999). This antibody has been utilized in several studies to deplete CD8+ T-lymphocytes in various rat strains (Sayegh et al. 1989; Hoffmann et al. 1997). Mouse anti-rat CD4 antibodies (W3/25) in ascites fluid are obtained from Accurate Chemical and Scientific, Westbury, N.Y. Affinity chromatography is utilized to purify anti-CD8 and anti-CD4 antibodies from culture supernatants and ascites fluid, respectively, quantified by spectrophotometry, and diluted in PBS.

Preliminary experiments determine the optimal doses and time of injection required to deplete CD8+ and CD4+ T-lymphocytes. In brief, WKY rats are treated with either antibody or both (0.2 mg to 1.0 mg injections, i.p.). Four, seven, and 10 days post-injection, rats are euthanized, peripheral lymph nodes and spleens harvested, mechanically and enzymatically digested to yield individual cells (Sekine et al. 1997). Depletion of CD8+ and/or CD4+ T-lymphoc. Immunization Protocol Studies performed in Example 5 will have determined the optimal dose and feeding schedule of col(V) to induce tolerance, and that dose and schedule is used to feed recipient rats in this Example. Feeding col(V) begins at the time point of maximal depletion of CD4+ and/or CD8+ T-lymphocytes as determined in the section above. Similar to preliminary data, immunized rats have a one-week recovery period between the completion of immunization and transplantation.

Data Collection and Analysis

Similar to Example 5, recipient rats are tested for DTH responses to donor (F344) antigens, followed by obtaining BAL fluid from native and allograft lungs. Cell free BAL is obtained from centrifuged specimens and supernatants stored at −80° C. Thoracic organs are harvested en bloc. Blood is collected by vena cava and cardiac puncture, specimens centrifuged to separate serum, and stored at −80° C.

d. Delayed-Type Hypersensitivity (DTH) Responses

To determine the contribution of CD4+ and CD8+ T-lymphocytes to the induction and maintenance of oral tolerance, DTH responses to donor (F344) antigens is performed in recipient rats in each group using the same methods described in Example 5.

e. Histologic Studies

To determine the requirement for CD4 and/or CD8+ T-lymphocytes for the induction and maintenance of tolerance induced by col(V), and prevention of rejection pathology, lung allografts will be graded for the rejection response as described in Example 5.

f. Determination of Cellular Cytotoxicity

Both CD4+ and CD8+ T-lymphocytes have been reported to induce cytotoxic activity in diseases other than lung allograft rejection, and these cells may function independently or provide help for each other to induce cytotoxicity (Lederman and Siciu-Foca 1999). The present inventor has shown that splenic lymphocytes, isolated from WKY rats two weeks post-transplantation of F344 lung allografts, induce cytotoxicity in F344 lymph node lymphocytes. Preliminary experiments, as above, will determine the role of CD4+ and CD8+ T-lymphocytes to induce cytotoxic T-lymphocytes responses during lung allograft rejection. In brief, peripheral lymph node cells are isolated from normal F344 (donor) rats, loaded with $^{51}$Cr (Amersham, Arlington Heights, Ill.), placed in 96 well flat bottom plates (target cells, $5\times10^3$/well) in complete media as described in Example 5. Pure splenic T-lymphocytes (>95% CD3+, isolated by magnetic beads—Dynal) or pure CD4+ or CD8+ splenic T-lymphocytes (effector cells, >95% pure) are obtained from WKY rats that received F344 lung allografts (allograft control group), and incubated in varying ratios with targets (E/T ratios of 1:1, 5:1, 10:1. and 100:1) at 37° C. for 4 hours. Cytotoxicity will be determined by specific $^{51}$Cr release induced by effector cells in each E/T ratio compared to release from loaded target cells, alone. By comparing cytotoxicity induced by unseparated T-lymphocytes compared to that induced by pure CD4+ or CD8+ T-lymphocytes, the role of CD4+ and CD8+ T-lymphocytes in cytotoxicity against cells expressing donor antigens can be determined.

The effect of col(V)-induced tolerance on the roles of CD4+ and CD8+ T-lymphocytes in anti-donor cytotoxicity in lung allograft rejection is determined by isolating pure CD4+ or CD8+ splenic lymphocytes (effector cells) from col(V)-fed WKY allograft recipients and utilizing them for cytotoxic lymphocytes studies as described above. To determine the requirement for CD4+ T-lymphocytes in CD8+ T-lymphocyte-induced cytotoxicity in tolerant recipients, CD8+ T-lymphocytes are isolated from CD4-depleted col (V)-fed allograft recipients and tested for cytotoxicity. To determine the requirement for CD8+ T-lymphocytes in CD4+ T-lymphocyte-induced cytotoxicity, CD4+ T-lymphocytes are isolated from CD8-depleted col(V)-fed allograft recipients and tested for cytotoxicity. Cytotoxicity is determined as specific $^{51}$Cr release from donor (F344) lymphocytes as described in Example 5.

Example 10

The Determination of Which Lymphocyte Subset is Able to Transfer Oral Tolerance
Experimental Groups:

| Transfer of naïve CD4+ and/or CD+ T-lymphocytes, n = 10 for each | Transfer of tolerant CD4+ T-lymphocytes n = 10 | Transfer of tolerant CD8+ T-lymphocytes n = 10 | Transfer of tolerant CD4+ plus CD8+ T-lymphocytes n = 10 |
|---|---|---|---|
| Donor: F344 rat lung (RT1$^{lv1}$) | Donor: F344 rat lung (RT1$^{lv1}$) | Donor: F344 rat lung (RT1$^{lv1}$) | Donor: F344 rat lung (RT1$^{lv1}$) |
| Recipient: WKY (RT1$^1$) rats - no feeding | Recipient: WKY (RT1$^1$) rats - no feeding | Recipient: WKY (RT1$^1$) rats - no feeding | Recipient: WKY (RT1$^1$) rats - no feeding | a. Description of Rats and Transplant Model

The donor (F344) and recipient (WKY) rats are identical to those described in Example 5. No immunosuppression is used.

b. Adoptive Transfer

CD4+ and CD8+ T-lymphocytes are isolated from spleen of normal WKY rats (naïve CD4 and CD8 T-lymphocytes) by mechanical and enzymatic digestion, followed by magnetic bead separation using anti-rat CD4+ and anti-rat CD8+ magnetic beads (Dynal) and beads removed before cells are used (Detachabead—Dynal). "Tolerant" CD4+ and CD8+ T-lymphocytes are isolated from spleens of col(V)-tolerized WKY rats that were recipients of F344 allografts. In brief, WKY rats are fed col(V) by protocol determined in Example 5, and F344 lung allografts are transplanted into the col(V)-fed rats one week after the last feeding. Two weeks post-transplantation, spleens are harvested and CD4+ and CD8+ T-lymphocytes isolated by magnetic bead separation as above ("tolerant" CD4+ and CD8+ T-lymphocytes). Flow cytometry is utilized to confirm >95% purity of cells isolated.

Twenty four hours prior to transplantation of F344 lung allografts, WKY rats are $10\times10^8$ purified "naïve" CD4+ or CD8+ T-lymphocytes, $10\times10^8$ purified CD4+ or CD8+ "tolerant" T-lymphocytes, or $5\times10^8$ CD4+ mixed with $5\times10^8$ CD8+ "tolerant" T-lymphocytes in 1 ml of PBS via by tail vein injection as described preliminary data. This quantity of cells was shown to effective in transferring tolerance to naïve allograft recipients in preliminary data.

Data Collection and Analysis

Similar to Example 5, recipient rats are tested for DTH responses to donor (F344) antigens, followed by obtaining BAL fluid from native and allograft lungs. Cell free BAL is obtained from centrifuged specimens and supernatants stored at −80° C. Thoracic organs are harvested en bloc. Blood is collected by vena cava and cardiac puncture, specimens centrifuged to separate serum, and stored at −80° C.

c. Delayed-Type Hypersensitivity (DTH) Responses

To determine if adoptive transfer of "tolerant" CD4+ and/or CD8+ T-lymphocytes results in diminished DTH responses to donor alloantigens in naïve lung allograft recipients, DTH responses to donor F344 antigens are performed in recipient rats in each group using the same methods described in Example 5.

d. Histologic Studies

Preliminary data showed that adoptive transfer of "tolerant" T-lymphocytes to naïve lung allograft recipients down-regulated the rejection response. To determine if prevention of lung allograft rejection by adoptive transfer of splenic T-lymphocytes is dependent on transfer of "tolerant" CD4 and/or CD8+ T-lymphocytes, lung allografts from each group are harvested and graded for rejection pathology as described in Example 5.

e. Cytokine Profiles Produced by "Tolerant" T-lymphocytes and Role in Alloimmune Responses A portion of spleens utilized as a source "tolerant" T-lymphocytes is mechanically digested to yield cell suspensions, passed over nylon columns to yield splenic lymphocytes, and T-lymphocytes (>95% pure) obtained using anti-rat CD3 magnetic bead (Dynal). Fluorescent mouse anti-rat antibodies are utilized to determine surface expression of CD4 or CD8, and presence of cytokines within the cells determined by fluorescent intracellular cytokine staining and examination by three color flow cytometry. In brief, CD4+ and CD8+ T-lymphocytes are stained for intracellular IL-4 and IL-10 for Th2 cells, TGF-β and IL-10 for Th3 cells or Tr1cells. High expression of TGF-β and low or absent expression of IL-10 identifies Th3 T-lymphocytes (Faria and Weiner 1999; Mayer 2000). High expression of IL-10 and low expression of TGF-β identifies Tr1 T-lymphocytes, and expression of IL-4 and IL-10 will identify Th2 T-lymphocytes. Antibodies and controls for staining are Pharmingen, except anti-TGF-β is obtained from R&D systems. Similarly stained CD4+ and CD8+ T-lymphocytes isolated from allograft control rats and normal WKY rats are controls.

f. Studies to Determine the Contribution of Active Suppression and Anergy to Induction of Oral Tolerance by Col(V)

If adoptive transfer of CD4+ or CD8+ T-lymphocytes from tolerant rats suppresses lung allograft rejection when adoptively transferred to naïve rats then the most likely mechanism is "active suppression" of alloimmmune responses. Utilizing transwell cell culture systems, the present inventor examined directly if CD4+ or CD8+ T-lymphocytes from col(V)-fed allograft recipients (tolerant rats) suppress the ability of T-lymphocytes from normal rats to respond to allogeneic stimulation. In brief, $3 \times 10^5$ lymph node T-lymphocytes (>95% CD3+) from normal WKY rats are cultured alone, or with $0.9 \times 10^5$ adherent splenocytes (APC's ) from normal F344 rats (stimulator: responder ratio, 0.3:1) in the bottom wells of transwell culture plates (Costar) in complete media. $3 \times 10^5$ pure CD4+ or CD8+ lymph node T-lymphocytes (WKY) from col(V)-fed allograft recipients (tolerant rats) are placed in the upper well alone, or in the presence of varying ratios of adherent splenocytes (APC's ) from normal F344 rats in ratios of 0:1, 0.15.1, 0.3:1, and 0.5:1. After a 5-day incubation, proliferation of lymphocytes in the bottom wells is determined by $^3$H-thymidine incorporation. This determines if alloantigen stimulation induces tolerant CD4+ or CD8+ T-lymphocytes (upper wells) to produce mediators that suppress the ability of normal T-lymphocytes to respond to allogeneic stimulation. Prior studies have shown that production of soluble mediators induced by antigenic stimulation occurs in a dose dependent manner (Taams et al. 1998). Therefore, by using varying ratios of stimulator cells (adherent splenocytes) in culture with tolerant T-lymphocytes from tolerant rats in the upper wells, these methods also determine if active suppression is dose dependent.

Failure of adoptive transfer experiments to fully suppress the rejection response could be due to the fact that anergy has occurred in these T-lymphocytes which are, therefore, unable to respond to antigenic stimulation (Faria and Weiner 1999; Taams et al. 1998; Taams et al. 1999). To determine if T-lymphocytes from tolerant lung allograft recipients are anergic, proliferative responses of T-lymphocytes from allograft control recipients and col(V)-fed allograft recipients are compared in a MLR. In brief, magnetic beads are utilized to purify CD4+ and CD8+ T-lymphocytes from lymph nodes of col(V)-fed allograft recipients and untreated allograft recipients (allograft control). $3 \times 10^5$ purified CD4+ or CD8+ T-lymphocytes from each group are cultured in varying ratios with adherent splenocytes (source of APC's ) from normal F344 rats (ratios of 0:1, 0.15:1, 0.3:1, and 0.5:1). After a 5-day incubation $^3$H-thymidine incorporation is utilized to determine proliferation in the two groups.

T-lymphocyte activation is dependent on expression of CD28 and CD40L (Lederman and Siciu-Foca 1999). In contrast to CD28, which is expressed constitutively, expression of CD40L is inducible in response to engagement of the T-cell receptor by MHC molecules on the APC. Since binding of CD40L to CD40 on APC's is necessary to complete T-lymphocyte activation, then oral tolerance-induced down-regulation of CD40L could explain anergy in T-lymphocytes isolated from tolerant lung allograft recipients. CD40L expression on CD4+ and CD8+ lymph node T-lymphocytes from WKY rats in untreated allografts (allograft control group), col(V)-fed allograft group, and normal rats are determined by flow cytometry (antibodies from Research Diagnostic Antibodies, Berkeley, Calif.). If CD40L expression is down-regulated on T-lymphocytes from the col(V)-fed allograft group compared to T-lymphocytes from untreated allograft recipients then further experiments are performed to determine the functional significance of the data (Liu et al. 1999) In brief, the $3 \times 10^5$ CD4 or CD8+ T-lymphocytes deficient in CD40L expression from tolerant WKY rats are incubated with varying ratios of adherent F344 splenocytes (0:1, 0.15:1, 0.3:1, and 0.5:1) in microtiter plates coated with mouse anti-rat CD40 antibodies or control antibodies (1-5 µg/ml) (Research Diagnostics). This technique induces crosslinking of CD40 on the APC's , and therefore, reproduces engagement by CD40L expressed on T-lymphocytes, which should correct the defect due to decreased CD40L expression on tolerant T-lymphocytes. After a 5-day incubation, proliferation is determined as reported in preliminary data. Controls for these experiments utilize species/isotype matched antibodies of an irrelevant specificity (Pharmingen).

Example 11

The Effect of Oral Tolerance on Phenotype and Function of APC's in Tolerized Recipients
Experimental Groups:

| Control Allograft (n = 20) | Col(V)-fed Allograft (n = 20) | CD4+ and CD8+ T-lymphocyte-depleted Col(V)-fed allograft (n = 20) |
|---|---|---|
| Donor: F344 rat lung (RT1$^{lv1}$) Recipient: WKY (RT1$^1$) rats - no feedings | Donor: F344 rat lung (RT1$^{lv1}$) Recipient: WKY (RT1$^1$) rats - fed col(V) | Donor: F344 rat lung (RT1$^{lv1}$) Recipient: T-lymphocyte depleted WKY (RT1$^1$) rats -fed col(V) | a. Description of Rats and Transplant Model

The donor (F344) and recipient (WKY) rats are identical to those described in Example 5. No immunosuppression is be used.

b. Depletion of T-lymphocytes

Experiments performed in the prior section will determine the optimal regimen for depleting CD4+ plus CD8+ T-lymphocytes prior to tolerance induction and transplantation.

Examining macrophages from CD4+/CD8+-lymphocyte-depleted recipients will determine the direct effect of col(V) on APC phenotype and function.

c. Immunization Protocol

Studies performed in Example 5 will have determined the optimal dose and feeding schedule of col(V) to induce tolerance, and that dose and schedule is used to feed recipient rats in this section. Feeding col(V) begins at the time point of maximal depletion of CD4+ and CD8+ T-lymphocytes as determined in the section above. Similar to preliminary data, immunized rats have a one week recovery period between the completion of immunization and transplantation.

Data Collection and Analysis

Two weeks post-transplantation, the recipient rats are euthanized, and spleens harvested.

d. Isolation of Macrophages and Analysis of Phenotype

As reported in preliminary data, spleens of recipient rats are mechanically and enzymatically digested to yield individual cells. Purified macrophages are obtained from splenocytes using anti-rat ED2 antibodies coupled to magnetic beads (Dynal) followed by magnetic bead separation. Macrophages isolated from normal WKY rats are >90% pure as determined by expression of high levels of ED2 and ED1, low expression of OX-6 (MHC class II), and CD86 by flow cytometry. All antibodies, as well as controls for these studies are from Serotec, Raleigh, N.C.

By comparing expression of these cell surface markers on macrophages from normal rats, unfed-WKY allograft recipients, and both groups of col(V)-fed allograft recipients, the effect of col(V)-induced oral tolerance on phenotype of macrophages, as well as the role of CD4+ and CD8+ T-lymphocytes in this process can be determined.

e. Isolation of Dendritic Cells and Analysis of Phenotype

Dendritic cells are enriched from splenocytes by single step density separation and magnetic bead isolation as described by Huang, et al (2000). In brief, splenocytes are washed, overlaid over NycoPrep solutions (NP 1.068, NycoMed, Oslo, Norway) per manufacturer's instruction and centrifuged at 400 g for 20 min at room temperature. The cells are removed from the interface, labeled with a cocktail of anti-lymphocyte mAbs: OX52 (pan-T cell), OX19 (CD5), OX8 (CD8), OX12 (Ig L chain), and OX33 (B cell CD45) (all Serotec) and separated using magnetic beads (MACS; Miltenyi Biotec) coated with goat anti-mouse Ig according to the manufacturer's instructions. To avoid maturing the dendritic cells, which affects their phenotype and function, no overnight adherence steps are utilized for purification. Dendritic cells from normal WKY rats isolated by this method are also be examined by flow cytometry to confirm >90% purity as defined by expression of OX62, CD11c, OX6, CD80, CD86, and CD40 (Serotec, and Research Diagnostics).

Expression of these cell surface markers on dendritic cells from normal rats and unfed-WKY allograft recipients are compared to expression of these same markers on dendritic cells isolated from both groups of col(V)-fed allograft recipients. In addition, examination of dendritic cell phenotype from col(V)-fed and T-lymphocyte-depleted col(V)-fed allograft recipients determines the effect of recipient CD4+ and CD8+ T-lymphocytes on dendritic cell phenotype in the tolerized recipient.

f. Mixed Leukocyte Reactions

The function of the purified macrophages and dendritic cells are determined by their ability to induce proliferation in allogeneic T-lymphocytes in a MLR. In brief, T-lymphocytes (>95% CD3+) are purified from peripheral lymph node from normal F344 rats as described above. $3 \times 10^5$ T-lymphocytes are co-cultured with purified mitomycin-C-treated macrophages or dendritic cells (isolated above) in varying ratios (0:1, 0.1:1, 0.3:1, and 0.5:1) in complete media, in 96 well flat bottom plates and (Costar). After pulsing with $^3$H-thymidinine, proliferation will be determined as reported in preliminary data.

Inability of APC's from tolerized recipients to stimulate T-lymphocytes could be due to decreased expression of the co-stimulatory molecules, CD80 or CD86 (Li et al. 1999; Lederman and Siciu-Foca 1999; Wu et al. 1998). Lack of lymphocyte proliferation due to diminished expression of these co-stimulatory molecules could be overcome by cross-linking the receptor for CD80 and CD86, which is CD28, expressed on the responding T-lymphocytes. Therefore, if APC's from tolerized recipients express low CD80 or CD86 and are poor stimulators of MLR's compared to normal APC's, then to determine the functional significance of low expression of these molecules, the MLR's are repeated in microtiter plates previously coated with murine-anti-rat CD28 antibodies (1-5 µg/ml) (Pharmingen). Controls for these experiments utilize species/isotype matched antibodies of an irrelevant specificity (Pharmingen).

Alternatively, macrophages and dendritic cells could down-regulate T-lymphocyte proliferation by producing different soluble suppressive mediators such as IL-10, nitric oxide, or TGF-β (39-41, 76-79). Specifically, IL-10 and nitric oxide are produced by macrophages and dendritic cells, and TGF-β is produced by macrophages (Medot-Pirenne et al. 1999; Vodovotz et al. 1998; Vodovitz et al. 1999; Yamamoto et al. 1998; Kawabe et al. 1992; Bonham et al. YEAR?; Bingisser et al. 1998).

To determine if macrophages and dendritic cells from tolerant rats produce factors that suppress alloimmmune reactions, MLR's are performed with and without addition of culture supernatants from "tolerant" macrophages and dendritic cells. In brief, purified macrophages or dendritic cells from tolerant lung allograft recipients are cultured in serum free media ($1 \times 10^6$ cells/ml). After a 24 h incubation the supernatants are harvested and stored at −80° C. until use. Mitomycin-C treated adherent splenocytes from normal WKY rats (stimulators) are co-cultured with purified F344 T-lymphocytes ($3 \times 10^5$) (responders) in 96 well culture plates (Costar) in ratios of 0:1 and 0.3:1 in 200 ul of complete media. Varying dilutions of macrophage or dendritic cell-conditioned culture supernatants from tolerant rats are added to each well (supernatant dilutions of 1:1, 1:5, and 1:10) to yield a final total volume 200 ul/well). Twenty four hours prior to the completion of a 5-day culture period, the wells are pulsed with $^3$H-thymidine and lymphocyte proliferation determined as described above.

If lymphocyte proliferation is suppressed in the presence of the supernatants then the following experiments will determine if macrophage or dendritic cell-derived IL-10, TGF-β, or nitric oxide from tolerized rats suppressed MLR's. EL-10 and TGF-β are assayed in culture supernatants by ELISA (R&D Systems) per manufacturer's protocol. Production of stable metabolic nitrites and nitrates in culture supernatants is determined by spectrophotometric analysis of culture supernatants by Greiss reaction (Kallio et al. 1997; Yamamoto et al. 1998; Kawabe et al. 1992).

If lymphocyte proliferation is suppressed in the presence of supernatants from macrophages or dendritic cells from tolerized rats, and these APC's produced IL-10, TGF-β, or nitric oxide, then the studies are repeated to determine if these mediators contributed to inhibition of lymphocyte proliferation. The studies above determine the dilution of culture supernatants that achieves maximal suppression of T-lymphocyte proliferation. Therefore, the MLR's are repeated adding this quantity of supernatants to the wells of the MLR with and without varying quantities of anti-rat IL-10 or anti-rat TGF-β antibodies, or appropriate control antibodies (0.1, 1.0, and 5 μg/ml) (R&D Systems) at the initiation of culture followed by assessment of lymphocyte proliferation at the completion of a 5-day culture.

A modification of these procedures is used to determine if nitric oxide contributed to suppression of MLR's. In brief, macrophages and dendritic cells isolated from tolerant rats, above, are cultured in serum free media ($1\times10^6$/ml) for three days plus or minus $N^g$-monomethyl-L-arginine (0.5 mM) (NGMA, Sigma), a potent inhibitor of inducible and constitutive nitric oxide production. Diminished or absent nitric oxide production in the supernatants will be determined by the Greiss reaction (Kallio et al. 1997; Yamamoto et al. 1998; Kawabe et al. 1992). MLR's are repeated as above plus addition of varying dilutions of this culture supernatant to the wells at the initiation of culture followed by determination of lymphocyte proliferation after a 5 day incubation.

Interpretation

Since tolerance induction may be dependent on interactions between CD4+ and CD8+ T-lymphocytes, then studies examining tolerance induction in rats depleted of either cell type will also determine if interactions between these cells are necessary for col(V)-induced tolerance. In addition, the presence of Th2, Th3, and Tr1 cells during tolerance induction to lung allografts are established, as well as the effects of oral tolerance on the phenotype and function of APC's in the recipient.

Clonal deletion, identified by the presence of apoptotic antigen-specific cells in lymphoid tissues of tolerant hosts, has been reported infrequently to contribute to tolerance induction (Chen et al. 1995). Determination of clonal deletion in the current studies would require identification of antigen specific clones, characterization of the V-beta regions of their T-cell receptors, then raising antibodies to these specific V-beta regions (Chen et al. 1995; Gagne et al. 2000). These antibodies are then utilized to identify presence of apoptotic antigen specific cells or absence of these cells by immunohistochemistry or flow cytometry analysis of lymphoid tissues. However, it is unlikely that clonal deletion contributed to col(V)-induced oral tolerance in the present model since very high doses of antigen (far in excess of 1 mg) are required to cause clonal deletion (Chen et al. 1995). In addition, preliminary studies utilizing TUNEL assays did not detect apoptotic cells in spleens or lymph nodes of tolerant lung allograft recipients and suggests that clonal deletion was not involved in tolerance in the present model. However, if anergy or active suppression does not fully account for the mechanism of col(V)-induced tolerance to lung allografts then studies of clonal deletion are performed.

If macrophages and/or dendritic cells from tolerant rats suppress T-lymphocyte stimulation in vitro, then to determine the functional significance in vivo, these "tolerant" macrophages and/or dendritic cells are adoptively transferred to naïve lung allograft recipients prior to transplantation followed by an assessment of the immunology and pathology of the rejection response.

Oral tolerance may be induced by col(V) affects both T-lymphocytes and APC's. Since lung allograft rejection is initiated by donor lung APC's stimulating recipient T-lymphocytes, then an additional strategy to prevent rejection episodes may be to induce tolerance by feeding col(V) to the donor, as well as the recipient prior to transplantation.

Example 12

| The Determination of Whether Peptides Present in Cyanogen Bromide Digests of α-chains of Col(V) Prevent the Development of Acute Rejection Experimental Groups: | | | |
|---|---|---|---|
| Allograft Control (n = 10) | Intact col(V)-fed (n = 20) | 1(V)-fed (n = 20) | 2(V)-fed (n = 20) |
| Donor: F344 rat lung (RT1$^{lv1}$) Recipient: WKY (RT1$^{l}$) rats - unfed | Donor: F344 rat lung (RT1$^{lv1}$) Recipient: WKY (RT1$^{l}$) rats - fed intact col(V) | Donor: F344 rat lung (RT1$^{lv1}$) Recipient: WKY (RT1$^{l}$) rats - fed 1(V) peptides | Donor: F344 rat lung (RT1$^{lv1}$) Recipient: WKY (RT1$^{l}$) rats - fed 2(V) peptides | a. Preparation of Type V Collagen from Human Lung

Type V collagen is isolated from human lungs obtained at autopsy. After lung tissues are minced, washed, and suspended in 0.5 M acetic acid containing 0.2 M NaCl, and digested by pepsin, supernatants are aspirated from centrifuged specimens, the pellet collected and the extraction procedure repeated. The supernatants are combined from the two digests, and stored at −70° C. Type V collagen is purified from the supernatants by differential NaCl precipitation from 0.5 M acetic acid (Piez et al. 1963; Woodbury et al. 1989). The cycle of solubilization in acetic acid and NaCl precipitation is repeated until a type V preparation with an α-chain ratio $\alpha1(V)/\alpha2(V)$ of approximately 2 is obtained as determined by SDS-polyacrylamide gel electrophoresis (Woodbury et al. 1989; Burgeson et al. 1976; Chiang et al. 1980). Separation of $\alpha1(V)$ from $\alpha2(V)$ is achieved by chromatography on DEAE-cellulose (Chiang et al 1980). The $\alpha1(V)$ and $\alpha2(V)$ chains are eluted from the column, and quantified by determination of the hydroxyproline content in the effluent.

b. Preparation of Cyanogen Bromide Peptides

The α-chains of collagen type V are further fractionated by digestion with cyanogen bromide, which cleaves the collagen at methionine residues (Miller et al. 1971). On completion of digestion, the samples are diluted 50 fold and lyophilized to remove the cyanogen bromide. The extent of digestion is screened on polyacrylamide gels. Individual peptides are isolated by a combination of ion exchange and molecular sieve chromatography.

Twenty WKY rats receive intact col(V), or pooled peptides from $\alpha1(V)$, or $\alpha2(V)$ by gastric gavage. The dosage and feeding regimen for intact col(V) or peptides in this Example are the same as determined for intact col(V) in Example 5. Two weeks post-transplantation, the rats in each group are sacrificed and lung harvested.

Data Collection and analysis c. Histologic Studies

The lung allografts from rats that received peptides, intact col(V), or no feeding (allograft control) are sectioned, fixed, stained, and analyzed as proposed in Examples 5-10 to detect the pathologic changes characteristic of acute lung allograft rejection. The α-chain digests that prevented rejection pathology are further studied in Example 12.

Example 13

Specific Peptides of α1(V) or α2(V) that Prevent the Devlopment of Acute Lung Allograft Rejection Experiments in Example 11 will have determined if the cyanogen bromide digests of α1(V) or α2(V) contained peptides that induced oral tolerance and prevented lung allograft rejection. Although pre-transplant immunizations by gastric gavage with the antigenic peptides of α1(V) or α2(V) prevent transplant rejection, non-antigenic peptides may also be highly effective in modulating the rejection response. The studies in Example 12 will determine not only the specific peptides recognized as antigens during rejection, but also the ability of non-antigenic and antigenic peptides to modulate the rejection response.

a. Selection of Antigenic and Non-Antigenic Peptides

Lymphocytes propagated from human lung allografts undergoing rejection proliferate in response to type V collagen (Wilkes et al. Submitted). The current studies will utilize similar techniques to determine the specific antigenic peptides within the cyanogen bromide digests of the collagen α-chains. These studies include only those α-chain digests that prevented the rejection response induced by induction of oral tolerance. Lymphocytes are propagated from lung allografts from the "allograft control" during rejection. Individual α-chain peptides are separated from the cyanogen bromide digests by a combination of ion-exchange and molecular sieve chromatography. Individual peptides (0-50 ug/ml) are co-cultured in 96-well flat bottom plates in complete media with propagated lung lymphocytes at 37° C. in 5% $CO_2$. Irradiated autologous (WKY) splenocytes added to the cultures serve as a source of APC's. Eighteen hours prior to the completion of a 3-day incubation, the cells are pulsed with $^3$H-thymidine and cell proliferation determined as the counts per minute of $^3$H-thymidine incorporation in triplicate cultures as reported in preliminary data. Antigenic peptides are identified as those collagen peptides that induce proliferation, and non-antigenic peptides identified as those that do not induce proliferation in propagated lung lymphocytes.

WKY rats mice receive antigenic or non-antigenic peptide by gastric gavage at a dose and schedule determined for intact col(V) in Examples 5-7.

Data Collection/Analysis

At the completion of the four week period, the thoracic organs, BAL, and serum are obtained from the recipient WKY rats as described in aims Examples 5-11.

b. DTH Responses to Donor Antigens

DTH responses to donor antigens are determined as described in Examples 5-7 c. Cytokine Profiles

Production of IL-4, IL-10, and TGF-β in serum and spleens are determined as described in Examples 5-7.

d. Cellular Cytotoxicity

The ability of alloantigen-specific lymphocytes to induce cytotoxicity in cells expressing donor antigens is determined as described in Examples 5-7.

Collectively, the above described studies determine the specific antigenic and/or non-antigenic peptides of col(V) that modulate rejection. In addition, these studies determine if modulation of the rejection response is dependent on immunization with antigenic peptides or if non-antigenic peptides are also able to modulate rejection activity.

Interpretation and Potential Difficulties

One potential difficulty in determining the specific peptides of col(V) that down-regulate acute rejection episodesis is that the α1(V) or α2(V) cyanogen bromide digests may not induce oral tolerance and prevent lung allograft rejection. This could be explained by the possibility that the tolerogenic region may have been the site of cyanogen bromide-induced cleavage. If this occurs, then other protein digestion techniques will be utilized to create collagen fragments for study.

Instead of inducing tolerance, feeding antigenic or non-antigenic peptides may accelerate or exacerbate lung allograft rejection. If this occurs, then either higher or lower doses of the peptides are utilized of immunization by gastric gavage. Indeed, even tolerogenic peptides may have variable effects on the immune response during induction of oral tolerance (Faria and Weiner 1999; Mayer 2000; Garside and Mowat 1997). Ultimately, the goal is to sequence the tolerogenic peptides so that synthetic peptides can be produced for pre-transplant immunization of patients on waiting lists for lung transplantation.

Example 14

The Role of Soluble Mediators in Oral Tolerance Induced by Col(V)

a. Rat Transplant Model and Immunization Protocol

Experiments performed in Examples 5-7 will have determined the optimal dose and feeding schedule of col(V) to induce oral tolerance to F344 lung allografts. Three groups are studied: F344 lung allografts transplanted into untreated WKY recipients-allograft control, col(V)-fed WKY rats that receive F344 lung allografts—col(V)-fed allografts, and cytokine-neutralized col(V)-fed allografts.

b. Detection of Systemic Cytokine Production

Production of IL-4, IL-10, CTGF, TGF-β, and nitric oxide in response to tolerance induced by col(V) is determined in Examples 5-7.

c. Neutralization of Cytokines and Nitric Oxide in vivo

Studies in the prior section determine if IL-4, IL-10, TGF-β, CTGF, and nitric oxide are produced systemically in response to tolerance induced by col(V). By neutralizing the cytokines, or inhibiting production of nitric oxide in vivo, experiments in this section determine the role of these mediators in col(V)-induced tolerance to lung allografts.

Goat anti-rat IL-4 and IL-10 are purchased from R&D Systems, and preliminary experiments determine the optimal dose of each antibody and duration of neutralization in col(V)-fed allograft recipients. Controls for these experiments utilize isotype and species matched antibodies R&D systems for injection. Anti-TGF-β antibodies are isolated for culture supernatants from a anti-murine-TGF-β antibody producing hybridoma supplied by Dr. Krees Melief (Joslen et al. 1998). This antibody has been utilized successfully to neutralize TGF-β activity in rats. Control antibodies for anti-TGF-β are murine IgG purchased from R&D systems. Anti-CTGF and control antibodies for anti-CTGF are supplied by Dr. George Martin. It is anticipated that two to three injections of the anti-cytokine antibodies will be required, one injection intraperitoneally immediately prior to transplantation and one or two injections during the two week post-transplantation period. Neutralization of IL-4 and IL-10 functional activity in serum are confirmed by CT.4S cell proliferation assay (Xu et al. 1995), and cytokine-synthesis inhibition assay (Fiorentino et al. ), respectively. Neutralization of TGF-β in serum is determined using the thymocyte proliferation assay (Wahl et al. ), and neutralization of CTGF by fibroblast proliferation assay (Mori et al. 1999; Grotendorst 1997). Col(V)-fed allograft recipients are treated with anti-cytokine or control antibodies as determined by preliminary experiments.

Inhibition of inducible nitric oxide production in col(V)-fed allograft recipients is achieved by aminoguanidine administration. In brief, col(V)-fed rats receive aminoguanidine hemisulfate (Sigma) by tail vein injection (400) mg/kg/d i.v. in three divided doses in 0.9% NaCl in a concentration of 100 mg/ml. Injections begin the day of transplantation surgery and continue until the completion of the two week study period. This regimen has been shown previously to decrease serum nitric oxide concentrations to 30% of normal in rats and will be confirmed in preliminary studies (Kallio et al. 1997).

Data Collection and Analysis d. Delayed-Type Hypersensitivity (DTH) Responses

Col(V)-induced tolerance to lung allografts results in diminished DTH responses to donor alloantigens (Yasufuku et al. Submitted). DTH responses are indicators of systemic immune responses to antigens (Faria and Weiner 1999; Mayer 2000; Garside and Mowat 1997). Neutralizing antibodies to IL-4, IL-10, TGF-β, and CTGF, as well as inhibition of nitric oxide production should have systemic effects on immune responses. Therefore, if involved in col(V)-induced immune suppression, then neutralizing these mediators should recover DTH responses to donor (F344) alloantigens. DTH responses to donor alloantigens (F344 splenocytes) in untreated col(V)-fed allograft recipients, and cytokine and nitric oxide-neutralized col(V)-fed allograft recipients are performed as described in Examples 5-7.

In addition to neutralizing immunosuppressants systemically, recent studies of tolerance show that adding anti-TGF-β antibodies to donor antigens injected into the pinnae of the tolerized rat recovers DTH responses to donor antigens (Bickerstaff et al. 2000). Importantly, recovery of DTH responses with local injection of anti-TGF-β antibodies was comparable to recovery of DTH response as the result of systemic neutralization of TGF-β. Therefore, DTH studies are also be done in a separate group of col(V)-fed allograft recipients using donor antigens (F344 splenocytes) mixed with neutralizing antibodies to these cytokines. In brief, splenocytes from normal F344 rats are suspended in PBS in the presence of the anti-cytokine antibody (1-5 µg/$10^7$ splenocytes). Twenty four hours after injection into the pinnae of WKY col(V)-fed allograft recipients, the specific ear swelling is measured as reported in preliminary data. Controls for these experiments are a separate group of col(V)-fed allograft recipients injected with F344 cells mixed with isotype/species-matched IgG antibodies (all R&D Systems, and control for CTGF from Dr. Martin from Fibrogen). Since antibodies do not neutralize nitric oxide activity, then comparable DTH studies cannot be performed for nitric oxide.

e. Histologic Studies

Histologic studies determine if systemic neutralization of IL-4, IL-10, TGF-β, CTGF, or nitric oxide abrogates the protective effect of col(V)-induced tolerance on lung allograft pathology. Grading of rejection pathology is performed as described in Examples 5-7.

f. Determination of Cellular Cytotoxicity

To determine if systemic production of IL-4, IL-10, TGF-β, CTGF, or nitric oxide suppresses anti-donor cytotoxic responses, cellular cytotoxicity to donor antigens are determined in col(V)-fed lung allograft recipients in which the activity of these mediators have been neutralized. These experiments are performed as described in Examples 5-7.

g. Detection of Apoptosis

Studies described in Examples 5-7 determine if col(V)-induced oral tolerance prevents apoptosis in lung allografts. Studies in this section determine if production of TGF-β, CTGF, nitric oxide, IL-4, or IL-10 contribute to prevention of apoptosis in lung allografts transplanted into tolerance recipients. Detection of apoptosis is performed by TUNEL assays as described in Examples 5-7. The groups to be studied are col(V)-fed allograft recipients and col(V)-fed allograft recipients in which TGF-β, CTGF, or nitric oxide was neutralized two weeks post-transplantation.

Interpretation

Significantly, studies in this Example and those in Examples 8-10 begin to identify if CTGF production affects immune responses, which has not been reported previously. A potential problem with these studies is that multiple cytokines, notably, IL-4, IL-10, and TGF-β, could be involved in tolerance to lung allografts. Indeed, Th2, Th3, and Tr1 T-lymphocytes implicated in suppression of immune responses during oral tolerance all produce more than one of these cytokines (Faria and Weiner 1999; Mayer 2000; Garside and Mowat 1997). Therefore, neutralization of an individual cytokine, such as IL-4, IL-10, or TGF-β may not abrogate the tolerant state induced by col(V). An alternate approach to determine the contribution of these cytokines to tolerance is to clone Th2, Th3, and Tr1 T-lymphocytes from tolerant lung allograft recipients for adoptive transfer to naïve lung allograft recipients followed by an assessment of the immunology and pathology of the rejection response.

Example 15

Treatment of Human Subjects in Need of Transplant

The data presented herein suggest that the methods of the present invention will be effective to prevent or diminish acute or chronic rejection episodes in human transplant recipients. It is contemplated that when a human subject is placed on a list to receive a transplant, the subject will begin receiving effective doses of a molecule that suppresses alloimmune responses, such as collagen compounds as described herein. The subject will receive the compounds by oral administration, preferably either by oral feeding or intrapulmonary instillation into the recipient.

The dosage will be determined by a number of factors that will be know to the skilled artisan. The subject will receive at least three doses of the compounds per month from the time the subject is placed on the transplant list until the time of transplantation. In some cases, the dosages will be administered every alternate day for four days in order to receive at least three doses of the compound per month. In other cases, the dosages will be administered every alternate day for eight days, for a total dosage of five times per month prior to transplant. In other cases, the subject will receive the compounds at least once per week from the time the subject is placed on the transplant list until the time of transplantation. Depending on the subject, the compounds may be administered at least twice per week from the time the subject is place on the transplant list until the time of transplantation.

Example 16

Treatment of Human Subjects After Transplant

It is further contemplated that treatment of a human subject who has received a transplant with a molecule that suppresses alloimmune responses, preferably a collagen compound, will prevent or diminish the onset of acute or chronic rejection episodes in the subject. In this case, the subject may or may not have received treatment with the compounds prior to the receipt of the transplant. As above, administration of the compounds will be orally, preferably either by oral feeding or by intrapulmonary instillation into the recipient.

Again, the dosage amounts will be determined by the skilled artisan based upon a number of factors known to the artisan. Whether the recipient has received treatment with the compounds prior to the transplant or not, the transplant subject will receive at least three doses of the compounds per month for at least two months following the transplant. These dosages may take the form of one dose every alternate day for four days, as above, for the three doses for the month. The following month, the transplant subject will receive another round of one dose every alternate day for four days. This procedure can be repeated as needed as determined by the skilled artisan. Alternatively, the subject may receive one dose every alternate day for eight days, for a total of five doses for the month, during the months, as needed, following the transplant. In other aspects, the subject may receive the dosages in weekly increments or two times per week, etc., as determined by the skilled artisan.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Chen, Inobe, Marks, Gonnella, Kuchroo, Weiner, "Peripheral deletion of antigen-reactive T cells in oral tolerance," *Nature*, 376:177-180, 1995.

Chen, Kuchroo, Inobe, Hafler, Weiner, "Regulatory T-cell clones induced by oral tolerance: suppression of autoimmune encephalomyelitis," *Science*, 265:1237-1240, 1994.

Chiang, Mainardi, Seyer, "Type V(A-B) collagen induces platelet aggregation," *J. Lab. Clin. Med.*, 95:99-107, 1980.

Cremer, Ye, Terato, Owens, Seyer, Kang, "Type XI collagen-induced arthritis in the Lewis rat: characterization of cellular and humoral immune responses to native types XI, V, and II collagen and constituent α-chains," *J. Immunol.* 153:824-832, 1994.

Danzer, Kirchner, Rink, "Cytokine interactions in human mixed lymphocyte culture," *Transplantation*, 57(11): 1638-1642, 1994.

DeMeester, Rolfe, Kunkel, Swiderski, Lincoln, Deeb, Strieter, "The bimodal expression of tumor necrosis factor-α in association with rat lung reimplantation and allograft rejection," *J. Immunol.*, 150(6):2494-2505, 1993.

Faria and Weiner, "Oral tolerance: mechanisms and therapeutic applications," *Adv. Immunol.*, 73:153-264, 1999.

Fedoseyeva, Zhang, Orr, Levin, Buncke, Benichou, "De novo autoimmunity to cardiac myosin after heart transplantation and its contribution to the rejection process," *J. Immunol.*, 162:6836-42, 1999.

Garrovillo, Ali, Oluwole, "Indirect allorecognition in acquired thymic tolerance: induction of donor-specific tolerance to rat cardiac allografts by allopeptide-pulsed host dendritic cells," *Transplantation*, 68:1827-1834, 1999.

Hancock, Sayegh, Kwok, Weiner, Carpenter, "Oral, but not intravenous, alloantigen prevents accelerated allograft rejection by selective intragraft Th2 cell activation," *Transplantation*, 55:1112-1118, 1993.

Hanson, Gorman, Oui, Cheah, Solomon, Trowsdale, "The human α2(XI) collagen gene (COL11A2) maps to the centromeric of the major histocompatibility complex on chromosome 6," *Genomics*, 5:925-931, 1989.

Hirt, You, Möller, Boeke, Starke, Spranger, Wottge, "Development of obliterative bronchiolitis after allogeneic rat lung transplantation: Implication of acute rejection and the time point of treatment," *J. Heart Lung Transplant.*, 18:542-548, 1999.

Huang, Fuchimoto, Scheier-Dolberg, Murphy, Neville, Sachs, *J. Clin. Invest.*, 105:173-181, 2000.

Ishido, Matsuoka, Matsuno, Nakagawa, Tanaka, "Induction of donor-specific hyporesponsiveness and prolongation of cardiac allograft survival by jejunal administration of donor splenocytes," *Transplantation*, 68:1377-1382, 1999.

Iyer, Woo, Cornejo, Gao, McCoubrey, Maines, Buelow, "Characterization and biologic significance of immunosuppressive peptide D2702.75-84(E α V) binding protein," *J. Bio. Chem.*, 273(5):2692-2697, 1998.

Joo, Pepose, Stuart, "T-cell mediated responses in a murine model of orthotopic corneal transplantation," *Invest. Ophthalmol. Vis. Sci.*, 36:1530-1540, 1995.

Konomi, Hayashi, Nakayasu, Arima, "Localization of type V collagen and type IV collagen in human cornea, lung, and skin," *Am. J. Pathol.*, 116:417-426, 1984.

Krensky and Clayberger, "HLA-derived peptides as novel immunosuppressives," *Nephrol. Dial. Transplant.*, 12:865-878, 1997.

Lowry, Marghesco, Blackburn, "Immune mechanisms in organ allograft rejection. VI. Delayed-type hypersensitivity and lymphotoxin in experimental renal allograft rejection," *Transplantation.*, 40:183-188, 1985.

Madri and Furthmayr, "Collagen polymorphism in the lung," *Human Pathology*, 11:353-366, 1980.

Madri and Furthmayr, "Isolation and tissue localization of type AB2 collagen from normal lung parenchyma," *Am. J. Pathol.*, 94:323-332, 1979.

Marck, Prop, Widevuur, "Lung transplantation in the rat. III. Functional studies in iso- and allografts," *J. Surgical Res.*, 35:149-158, 1983.

Matsumura, Marchevsky, Zuo, Kass, Matloff, Jordan, "Assessment of pathological changes associated with chronic allograft rejection and tolerance in two experimental models of rat lung transplantation," *Transplantation.*, 59:1509-1517, 1995.

Morris and Bachinger, "Type XI collagen is a heterotrimer with the composition (1α,2α, 3α) retaining non-triple helical domains. *J. Biological Chem.*, 262:11345-11350, 1987.

Murphy, Magee, Alexander, Waaga, Snoeck, Vella, Carpenter, Sayagh, "Inhibition of allorecognition by a human class II MHC-derived peptide through the induction of apoptosis," *J. Clin. Invest.*, 103:859-867, 1999.

Nösner, Goldberg, Naftzger, Lyu, Clayberger, Krensky, "HLA-derived peptides which inhibit T cell function bind to members of the heat-shock protein 70 family," *J. Exp. Med.*, 183:339-348, 1996.

Oluwole, Chowdhury, Jin, Hardy, "Induction of transplantation intolerance to rat cardiac allografts by intrathymic inoculation of allogeneic soluble peptides," *Transplantation*, 56(6):1523-1527, 1993.

Prop, Nieuwenhuis, Wildevuur, "Lung allograft rejection in the rat. I. Accelerated rejection caused by graft lymphocytes," *Transplantation*, 40:25-30, 1985.

Prop, Wildevuur, Nieuwenhuis, "Lung allograft rejection in the rat. II. Specific immunological properties of lung grafts," *Transplantation*, 40:126-131, 1985.

Sayagh, Watschinger, Carpenter, "Mechanisms of T cell recognition of alloantigen," *Transplantation*, 57:(9)1295-1302, 1994.

Sayegh and Krensky, "Novel immunotherapeutic strategies using MHC derived peptides," *Kidney Int. Suppl.* 53:S13-20, 1996.

Sayegh, Khoury, Hancock, Weiner, Carpenter, "Induction of immunity and oral tolerance with polymorphic class II major histocompatibility complex allopeptides in the rat," *Proc. Natl. Acad. Sci.*, 89: 7762-7766, 1992.

Sayegh, Zhang, Hancock, Kwok, Carpenter, Weiner, "Down-regulation of the immune response to histocompatibility antigens and prevention of sensitization by skin allografts by orally administered alloantigen," *Transplantation*, 53:163-166, 1992.

Sekine, Nowen, Heidler, Van Rooijen, Brown, Cummings, Wilkes, "Role of passenger leukocytes in allograft rejection—Effect of depletion donor alveolar Macrophages on the local production of TNF-alpha, T helper 1/Thelper 2 cytokines, IgG subclasses, and pathology in a rat model of lung transplantation," *J. Immunol*, 159:4084-4093, 1997.

Seyer and Kang, "Covalent structure of collagen: amino acid sequence of three cyanogen bromide-derived peptides from human alpha 1(V) collagen chain. *Arch. Biochem. Biophys.* 271(1): 120-129, 1989.

SivaSai, Smith, Poindexter, Sundaresan, Trulock, Lynch, Cooper, Patterson, Mohanakumar, "Indirect recognition of donor HLA class I peptides in lung transplant recipients with bronchiolitis obliterans syndrome," *Transplantation.* 67(8):1094-1098, 1999.

Smith Jr, Williams, Brandt, "Interaction of proteoglycans with pericellular (1 alpha, 2 alpha, 3 alpha) collagens of cartilage," *J. Biol. Chem.*, 260:10761-10767, 1985.

Stark and Ostrow, *Training Manual Series, Laboratory Animal Technician*, American Association for Laboratory Animal Science, 181-182, 1990.

Strober and Coffman, "Tolerance and immunity in the mucosal immune system," *Res. Immunol.*, 148:489-599, 1997.

Trulock, "Lung transplantation," *Am. J. Respir. Crit. Care Med.*, 155:789-818, 1997.

VanBuskirk, Wakely, Sirak, Orosz, "Patterns of allosensitization in allograft recipients: long-term allograft acceptance is associated with active alloantibody production in conjunction with active inhibition of alloreactive delayed-type hypersensitivity," *Transplantation.*, 65:1115-1123, 1998.

Westra, Prop, Kuijpers, "A paradox in heart and lung rejection," *Transplantation*, 49:826-828, 1990.

Whitacre, Gienapp, Orosz, Bitar, "Oral tolerance in experimental autoimmune encephalomyelitis. III. Evidence for clonal anergy," *J. Immunol.*, 147:2155-2163, 1991.

Wilkes, Bowman, Cummings, Heidler, "Allogeneic bronchoalveolar lavage cells induce the histology and immunology of lung allograft rejection in recipient murine lungs. Role of ICAM-1 on donor cells," *Transplantation*, 67(6):890-896, 1999.

Wilkes, Heidler, Bowen, Quinlan, Doyle, Cummings, Doerschuk, "Allogeneic bronchoalveolar lavage cells induce the histology of acute lung allograft rejection, and deposition of IGg2a in recipient murine lungs," *J. Immunol.*, 155:2775-2783, 1995.

Wilkes, Thompson, Cummings, Bragg, Heidler, "Instillation of allogeneic lung macrophages and dendritic cells cause differential effects on local IFY-γ production, lymphocytic bronchitis, and vasculitis in recipient murine lungs," *J. Leukoc. Biol.* 64:578-586, 1998.

Wilson, Ebringer, Ahmadi, Wrigglesworth, Tiwana, Fielder, Binder, Ettelaie, Cunningham, Joannou, Bansal," "Shared amino acid sequences between major histocompatibility complex class II glycoproteins, type XI collagen and Proteus mirabilis in rheumatoid arthritis," *Ann. Rheum. Dis.,"* 54:216-220, 1995.

Woessner Jr., "The determination of hydroxyproline in tissue and protein samples containing small proportions of this immino acid," *Arch. Biochem. Biophys.* 93:440-447, 1961.

Yagyu, Steinhoff, Schäfers, Dammenhayn, Haverich, Borst, "Comparison of mononuclear cell populations in brochoalveolar lavage fluid in acute rejection after lung transplantation and Mycoplasma infection in rats," *J. Heart Transplant.*, 9:516-525, 1990.

Yamagami, Tsuru, Ohkawa, Endo, Isobe, "Suppression of allograft rejection with anti-alpha beta T cell receptor antibody in rat corneal transplantation," *Transplantation*, 67:600-604, 1999.

Yoshino, Quattrocchi, Weiner, "Suppression of antigen-induced arthritis in Lewis rats by oral administration of type II collagen," *Arthritis Rheum.* 38: 1092-1096, 1995.

Yousem, Berry, Cagle, Chamberlain, Husain, Hruban, Marchevsky, Ohori, Ritter, Stewart, Tazelaar," "Revision of the 1990 working formulation for the classification of pulmonary allograft rejection: Lung rejection study group," *J. Heart Lung Transplant*, 15:1-15, 1996.

Zheng, Markees, Hancock, Li, Greine, Li, Mordes, Sayegh, Rossini, Strom, "CTLA4 signals are required to optimally induce allograft tolerance with combined donor-specific transfusion and anti-CD154 monoclonal antibody treatment," *J. Immunol.*, 162:4983-4990, 1999.

The invention claimed is:

1. A method for suppressing an alloimmune response to a lung allograft comprising administering collagen type V to a lung transplant recipient, wherein the collagen type V is administered prior to receipt of the lung allograft and suppresses an alloimmune response in the recipient.

2. The method of claim 1, wherein said administering is by intrapulmonary instillation into the recipient.

3. The method of claim 1, wherein said administering is by oral feeding.

4. A method for suppressing the induction of an immune rejection response against a transplanted lung allograft comprising administering collagen type V to a lung transplant recipient, wherein the collagen type V is administered prior to receipt of the lung allograft.

5. The method of claim 4, wherein said administering is by intrapulmonary instillation into the recipient.

6. The method of claim 4, wherein said administering is by oral feeding.

7. A method for suppressing proliferative responses of lung T-lymphocytes to donor alloantigens in a transplant recipient following transplantation of a lung allograft comprising administering collagen type V to said recipient. wherein the collagen type V is administered prior to receipt of the lung allograft.

8. The method of claim 7, wherein said administering is by intrapulmonary instillation into the recipient.

9. The method of claim 7, wherein said administering is by oral feeding.

10. A method for suppressing apoptosis in a lung transplant recipient following transplantation of a lung allograft comprising administering collagen type V to said recipient, wherein the collagen type V is administered prior to receipt of the lung allograft.

11. The method of claim 10, wherein said administering is by intrapulmonary instillation into the recipient.

12. The method of claim 10, wherein said administering is by oral feeding.

13. A method for reducing the rejection of a transplanted lung allograft in a human patient comprising administering collagen type V to the patient, wherein the collagen type V is administered prior to receipt of the lung allograft.

14. The method of claim 13, wherein said administering is by intrapulmonary instillation into the recipient.

15. The method of claim 13, wherein said administering is by oral feeding.

* * * * *

UNITED STATES PATENT AND TRADEMARK OFFICE
CERTIFICATE OF CORRECTION

PATENT NO. : 7,348,005 B2  Page 1 of 1
APPLICATION NO. : 10/243797
DATED : March 25, 2008
INVENTOR(S) : David Wilkes It is certified that error appears in the above-identified patent and that said Letters Patent is hereby corrected as shown below:

In Title page, Item (54) Title, please delete "COLLAGEN" and insert --COLLAGEN TYPE V-- therefor.

In Claim 7, Column 71, Line 15, please delete "." and insert --,-- therefor.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,348,005 B2 Page 1 of 1
APPLICATION NO. : 10/243797
DATED : March 25, 2008
INVENTOR(S) : David Wilkes It is certified that error appears in the above-identified patent and that said Letters Patent is hereby corrected as shown below:

In Title Page, Item (73) Assignee, please delete "Advanced Research and Technology Institute" and insert --Indiana University Research and Technology Corporation-- therefor.

Signed and Sealed this

First Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,348,005 B2
APPLICATION NO. : 10/243797
DATED : March 25, 2008
INVENTOR(S) : David Wilkes Page 1 of 1

It is certified that error appears in the above-identified patent and that said Letters Patent is hereby corrected as shown below:

In Title page, Item (54) Title, please delete "COLLAGEN" and insert --COLLAGEN TYPE V-- therefor.

In Claim 7, Column 71, Line 15, please delete "." and insert --,-- therefor.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO.       : 7,348,005 B2  
APPLICATION NO.  : 10/243797  
DATED            : March 25, 2008  
INVENTOR(S)      : David Wilkes Page 1 of 1

It is certified that error appears in the above-identified patent and that said Letters Patent is hereby corrected as shown below:

In Title page, Item (54) and Column 1, line 2, Title, please delete "COLLAGEN" and insert --COLLAGEN TYPE V-- therefor.

In Claim 7, Column 71, Line 15, please delete "." and insert --,-- therefor.

This certificate supersedes the Certificate of Correction issued November 11, 2008.

Signed and Sealed this

Ninth Day of December, 2008

JON W. DUDAS  
*Director of the United States Patent and Trademark Office*